US011253653B2

(12) United States Patent
Hostettler et al.

(10) Patent No.: US 11,253,653 B2
(45) Date of Patent: Feb. 22, 2022

(54) SEGMENTED PISTON ROD FOR A MEDICATION DELIVERY DEVICE

(71) Applicant: Ypsomed AG, Burgdorf (CH)

(72) Inventors: Patrick Hostettler, Hasle (CH); Jürg Hirschel, Bern (CH); Simon Scheurer, Bern (CH)

(73) Assignee: Ypsomed AG, Burgdorf (CH)

( * ) Notice: Subject to any disclaimer, the term of this patent is extended or adjusted under 35 U.S.C. 154(b) by 104 days.

(21) Appl. No.: 16/229,794

(22) PCT Filed: May 24, 2017

(86) PCT No.: PCT/CH2017/000052
§ 371 (c)(1),
(2) Date: Dec. 21, 2018

(87) PCT Pub. No.: WO2017/219156
PCT Pub. Date: Dec. 28, 2017

(65) Prior Publication Data
US 2019/0240417 A1 Aug. 8, 2019

(30) Foreign Application Priority Data

Jun. 23, 2016 (EP) .................................... 16175898

(51) Int. Cl.
*A61M 5/315* (2006.01)
*A61M 5/145* (2006.01)
(Continued)

(52) U.S. Cl.
CPC ...... *A61M 5/31511* (2013.01); *A61M 5/1452* (2013.01); *A61M 5/14248* (2013.01);
(Continued)

(58) Field of Classification Search
CPC ........... A61M 2005/31518; A61M 2005/3152; A61M 5/31511; A61M 5/31528;
(Continued)

(56) References Cited

U.S. PATENT DOCUMENTS 5,957,889 A * 9/1999 Poulsen ............ A61M 5/14566
604/131
6,474,219 B2 11/2002 Klitmose et al.
(Continued)

FOREIGN PATENT DOCUMENTS

DE 102004059491 A1 7/2006
WO 9509021 A1 4/1995
(Continued)

OTHER PUBLICATIONS

International Preliminary Report on Patentability for International Application No. PCT/CH2017/000052, dated Dec. 25, 2018 (10 pages).

*Primary Examiner* — Jason E Flick
*Assistant Examiner* — Anna E Goldberg-Richmeier
(74) *Attorney, Agent, or Firm* — Dorsey & Whitney LLP

(57) ABSTRACT

A segmented piston rod for an injection device includes multiple segments joined together via a hinge located on one side of each segment. The piston rod can be bent in one direction by articulating subsequent hinges while an axial force can be transmitted by the segmented piston rod to the stopper when the subsequent hinges are closed and the segments abut each other opposite to the one side of the hinge. The segmented piston rod is secured against rotation relative to the housing around the longitudinal axis of the segmented piston rod. The segmented piston rod has a last element which abuts the stopper in the reservoir and a first segment which is opposite to the last segment. The first segment is includes an internal thread matching an external (Continued)

thread of a drive sleeve and rotation of the drive sleeve advances the piston rod towards the stopper of the reservoir.

14 Claims, 39 Drawing Sheets

(51) Int. Cl.
*A61M 5/142* (2006.01)
*A61M 5/32* (2006.01)

(52) U.S. Cl.
CPC ....... *A61M 5/3232* (2013.01); *A61M 5/31576* (2013.01); *A61M 5/31583* (2013.01); *A61M 5/3234* (2013.01); *A61M 2005/14284* (2013.01)

(58) Field of Classification Search
CPC .. A61M 5/14248; A61M 5/20; A61M 5/1452; A61M 5/31513; A61M 5/31515; A61M 5/31583; B05C 17/0113; F04B 9/02
See application file for complete search history.

(56) References Cited

U.S. PATENT DOCUMENTS

| | | | |
|---|---|---|---|
| 9,107,999 B2 | 8/2015 | Moberg et al. | |
| 2001/0034502 A1* | 10/2001 | Moberg | A61M 5/16831 604/154 |
| 2005/0188166 A1 | 8/2005 | Fujibayashi et al. | |
| 2005/0251097 A1* | 11/2005 | Mernoe | A61M 5/14244 604/221 |
| 2014/0358113 A1* | 12/2014 | Mernoe | A61M 5/14566 604/500 |

FOREIGN PATENT DOCUMENTS

| | | | | |
|---|---|---|---|---|
| WO | 9810814 A1 | 3/1998 | | |
| WO | 9857688 A1 | 12/1998 | | |
| WO | 0178812 A1 | 10/2001 | | |
| WO | 0183008 A1 | 11/2001 | | |
| WO | 0240083 A2 | 5/2002 | | |
| WO | 2004056411 A3 | 8/2004 | | |
| WO | 2005002649 A1 | 1/2005 | | |
| WO | 2007038059 A3 | 6/2007 | | |
| WO | 2010029054 A1 | 3/2010 | | |
| WO | 2011012465 A1 | 2/2011 | | |
| WO | 2011046950 A1 | 4/2011 | | |
| WO | 2013140395 A1 | 9/2013 | | |
| WO | 2015032747 A1 | 3/2015 | | |
| WO | 2016091841 A1 | 6/2016 | | |
| WO | WO-2016091841 A1 * | 6/2016 | | A61M 5/24 |

* cited by examiner

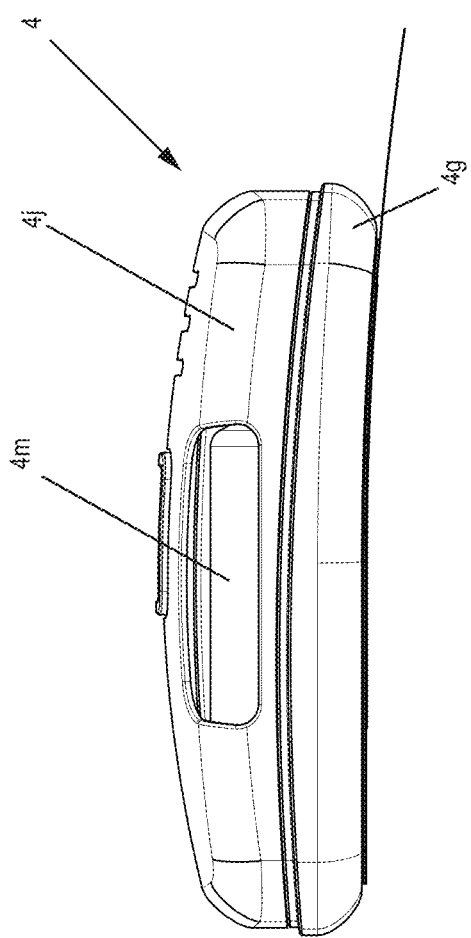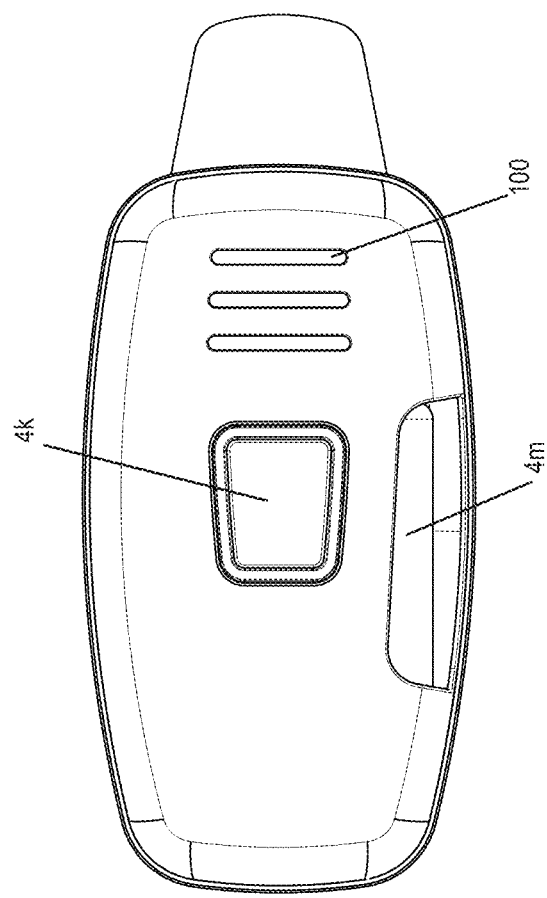

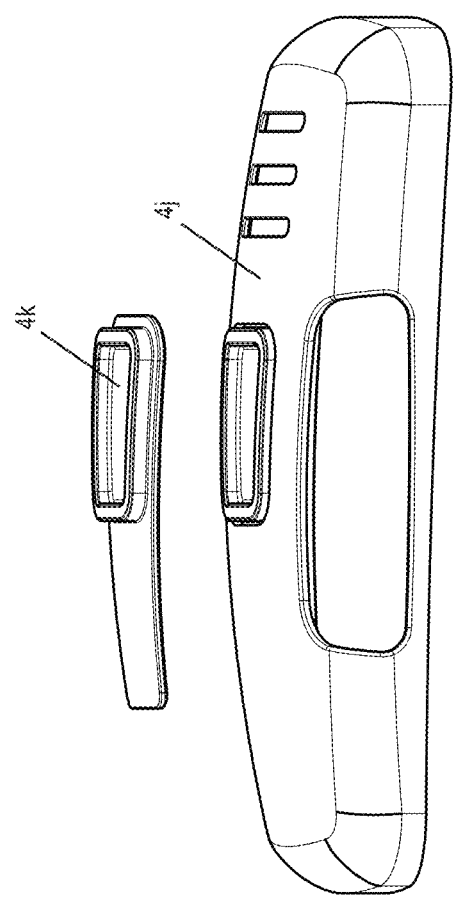
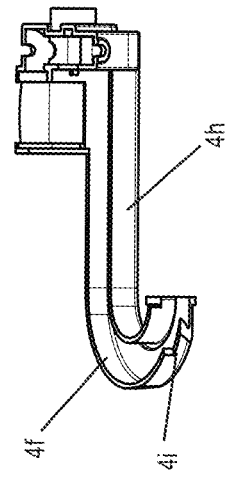
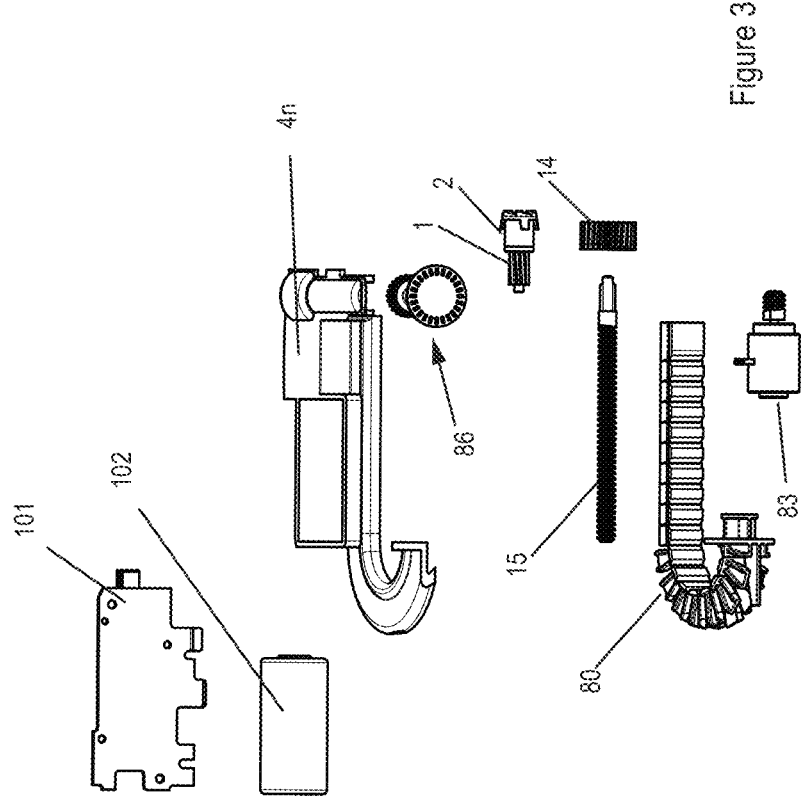

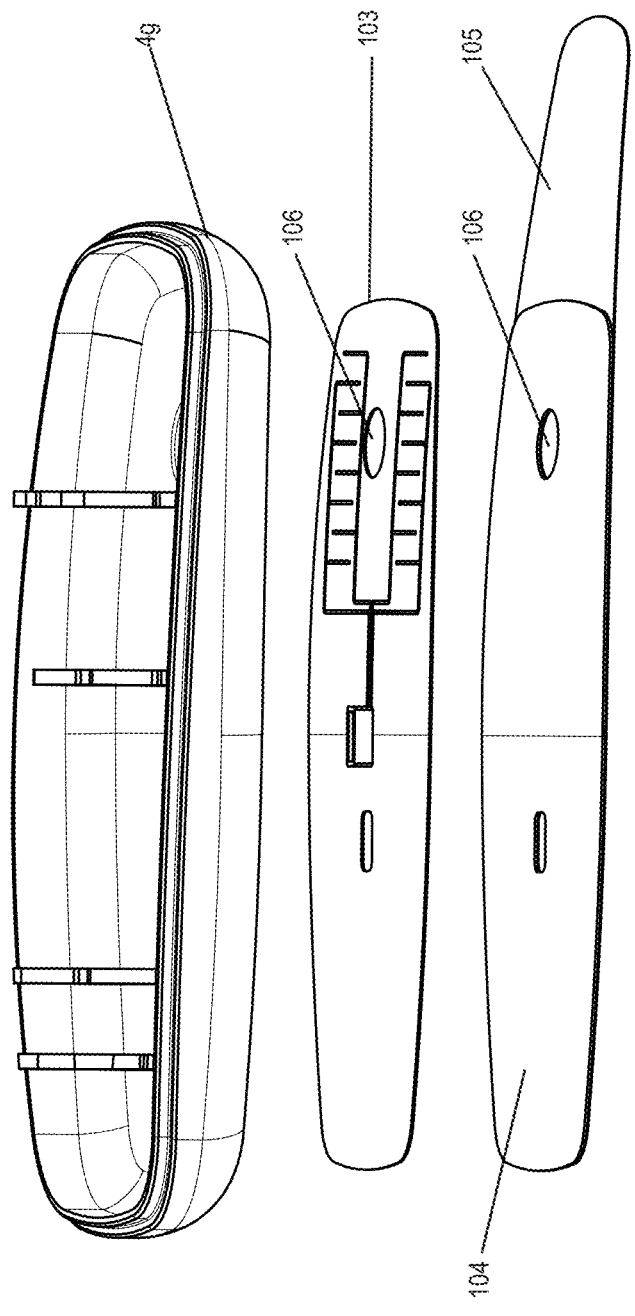
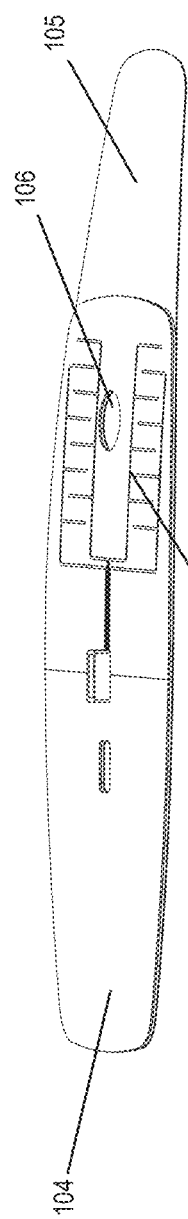

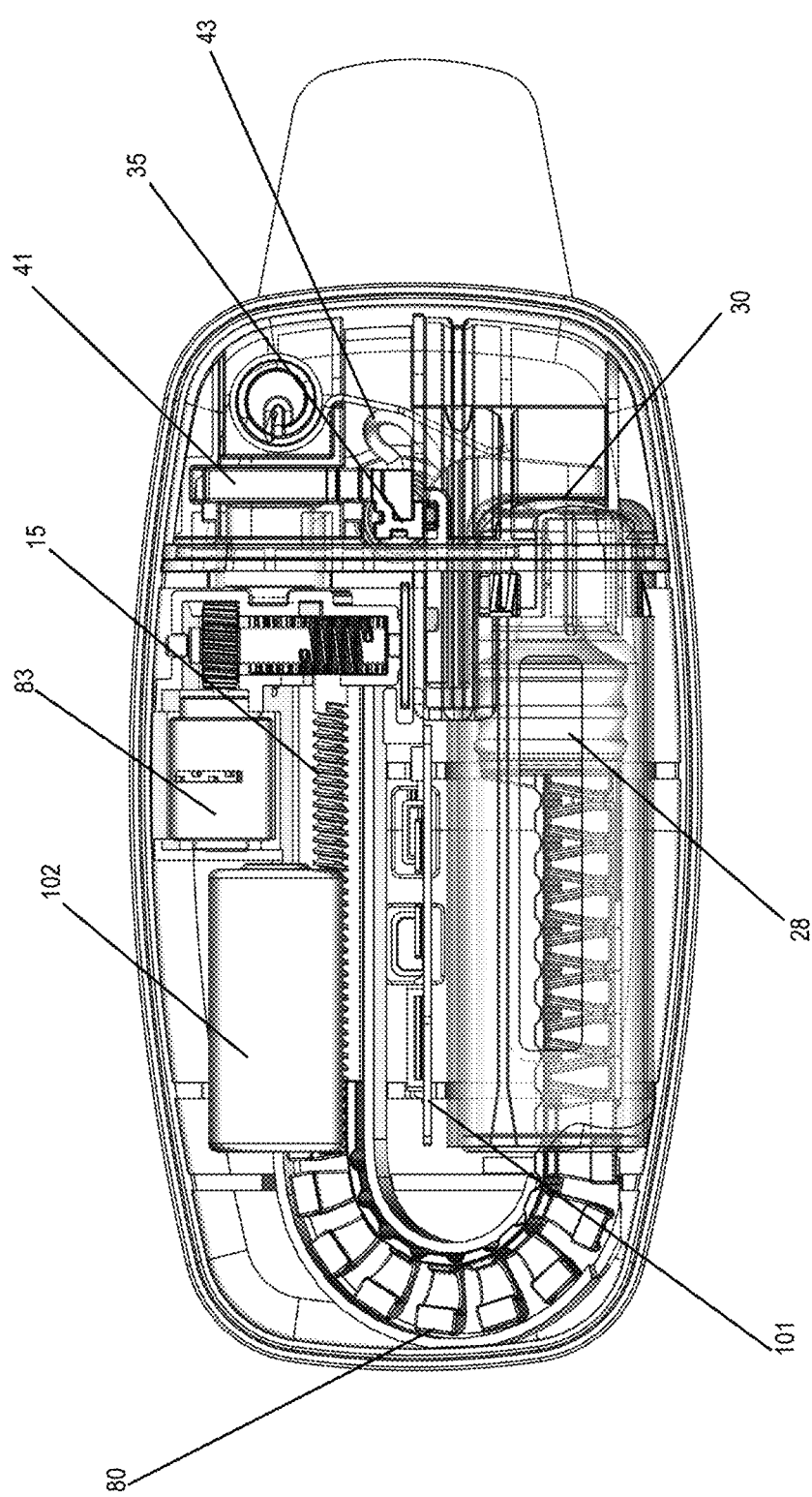

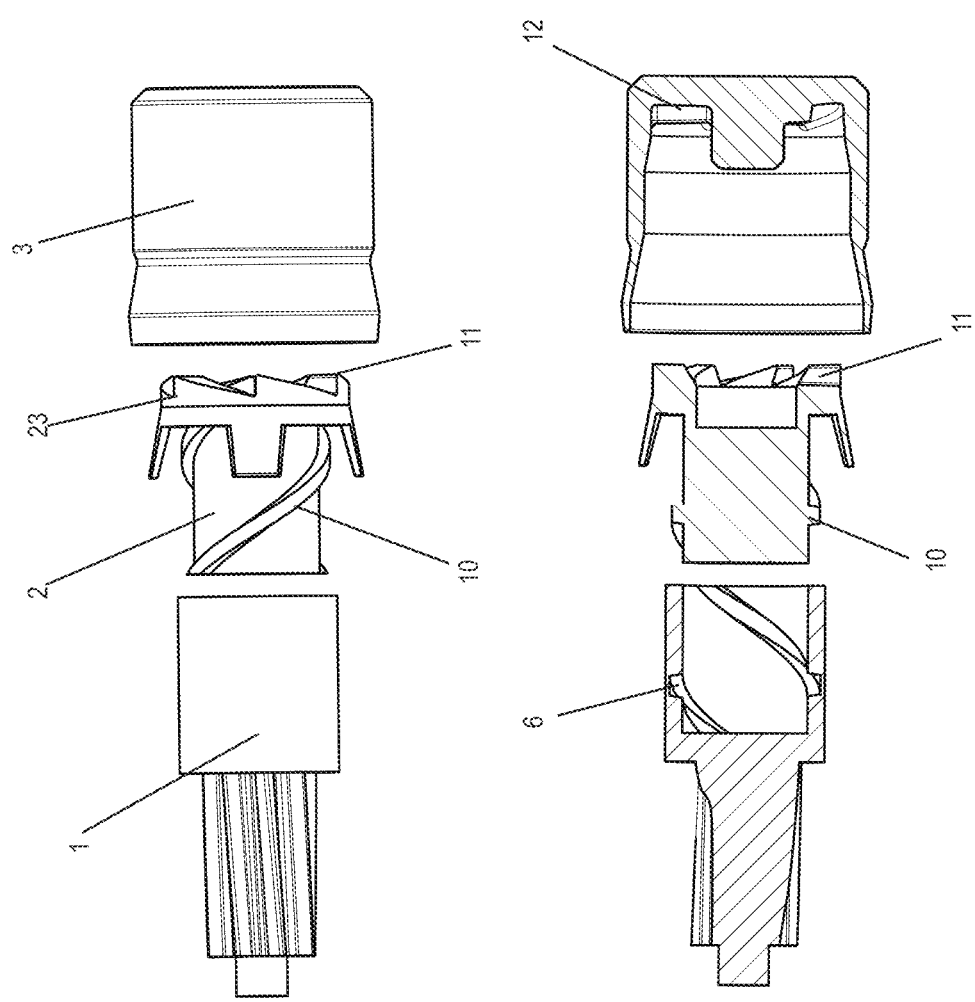

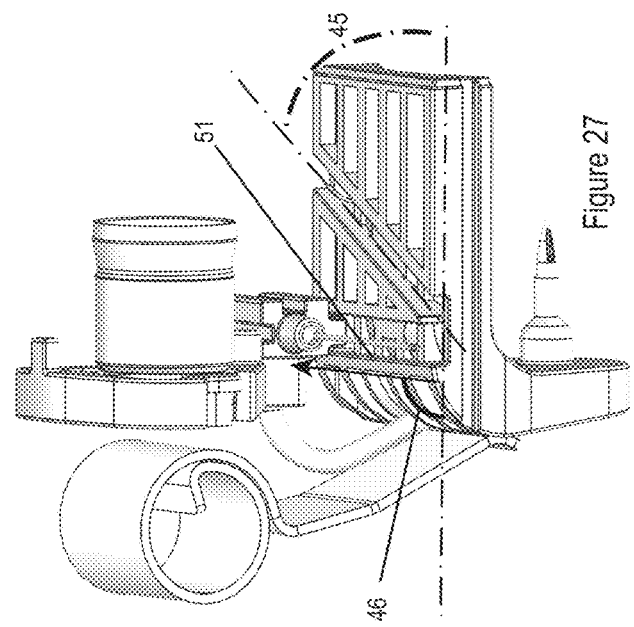
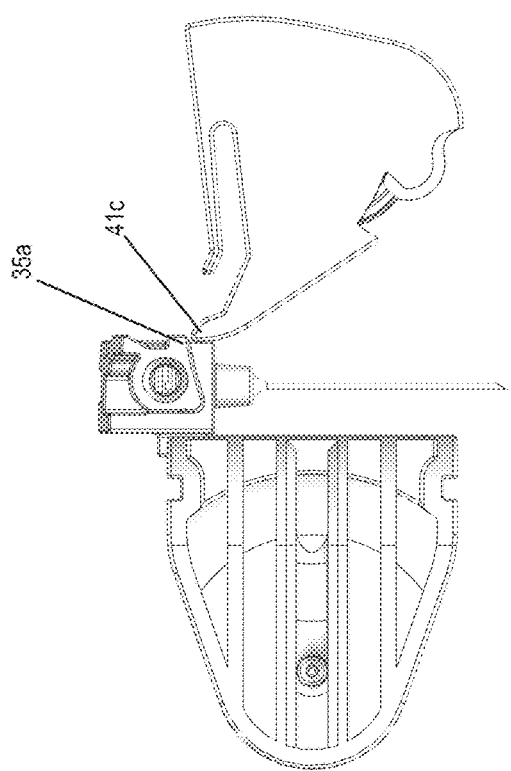

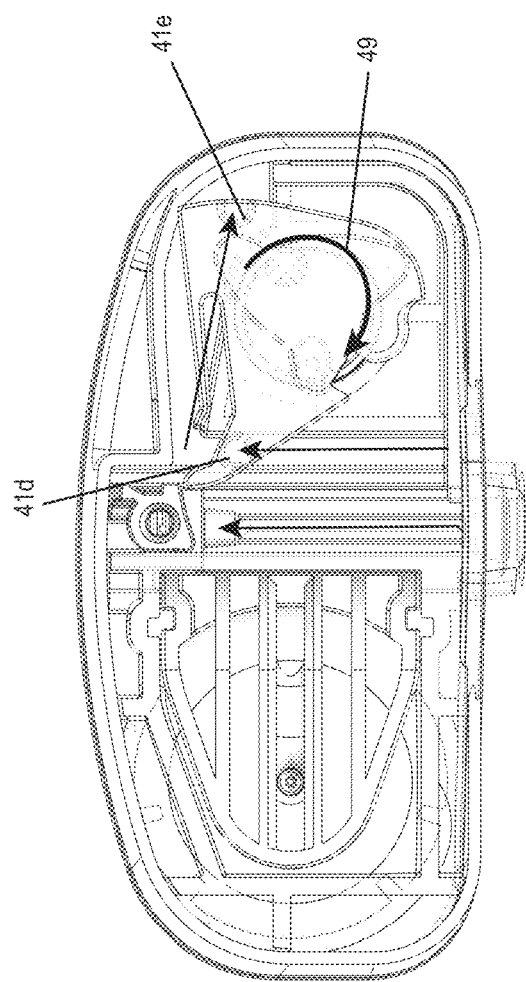

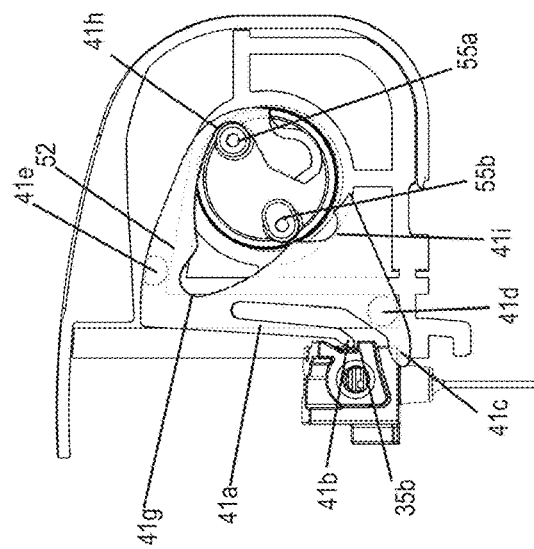
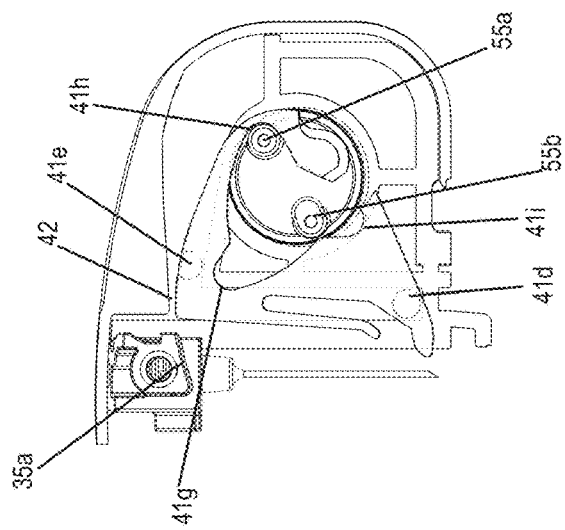
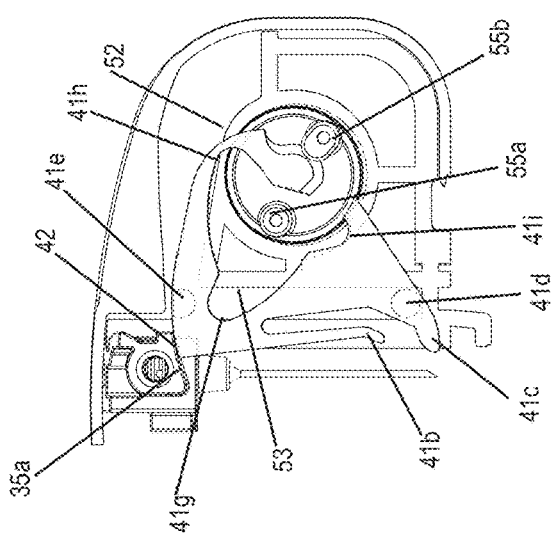

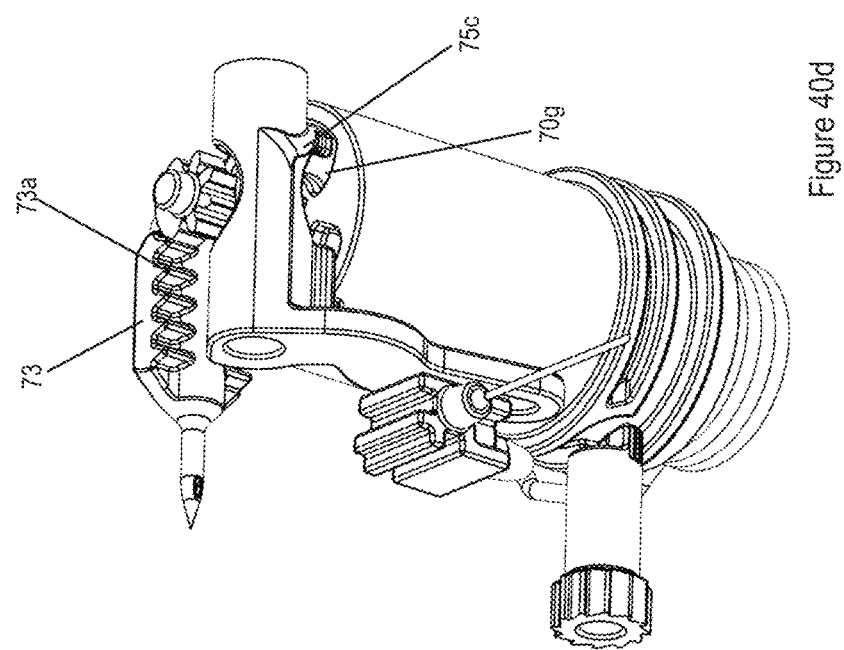

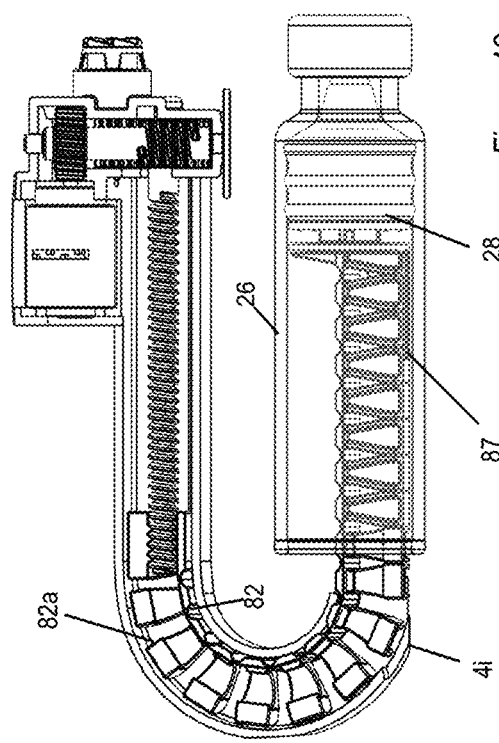
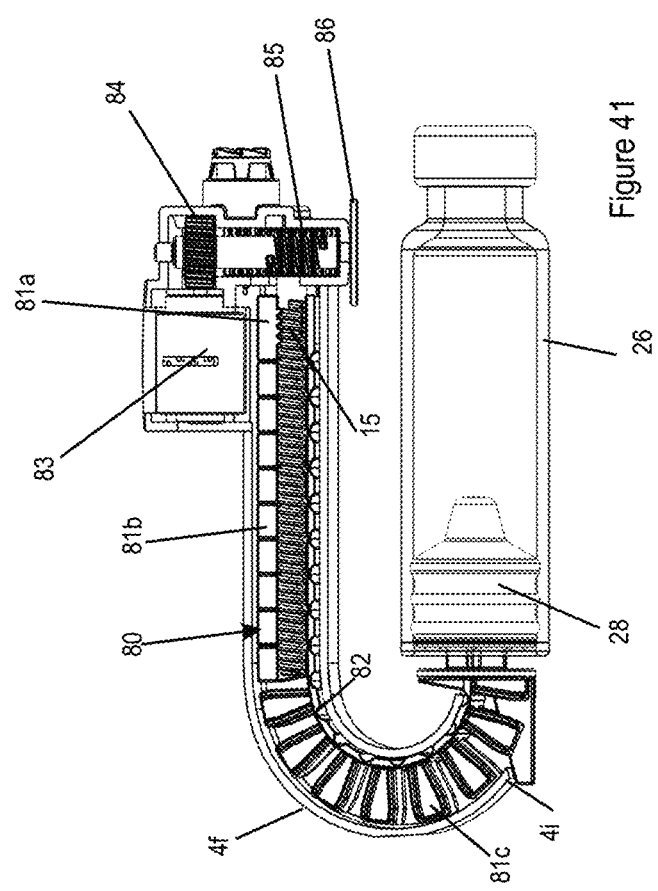

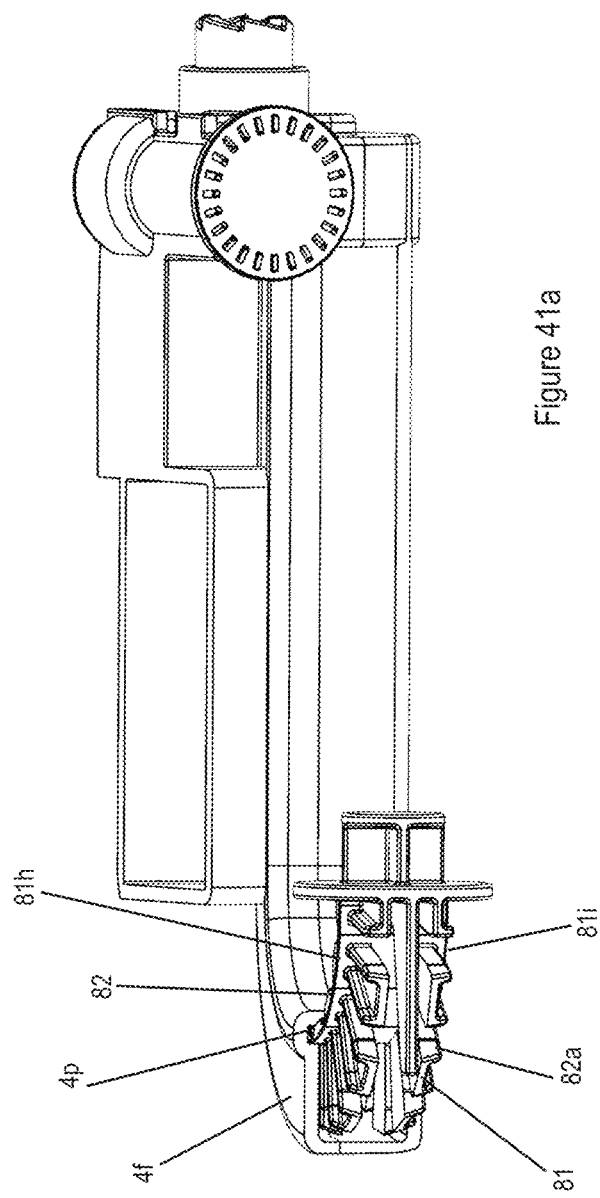

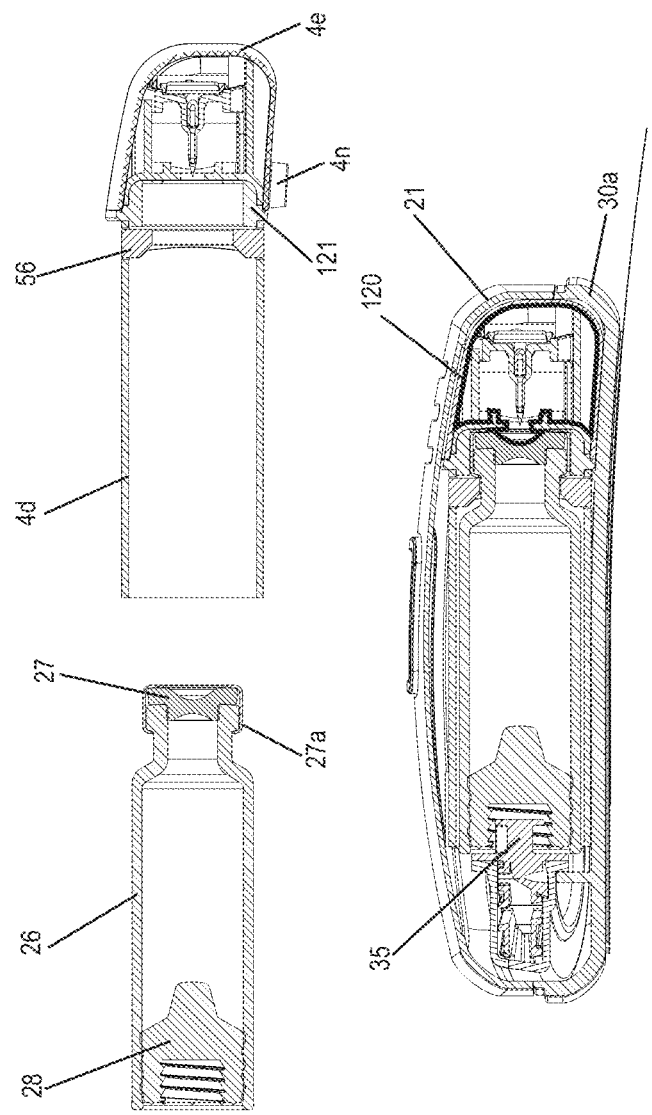

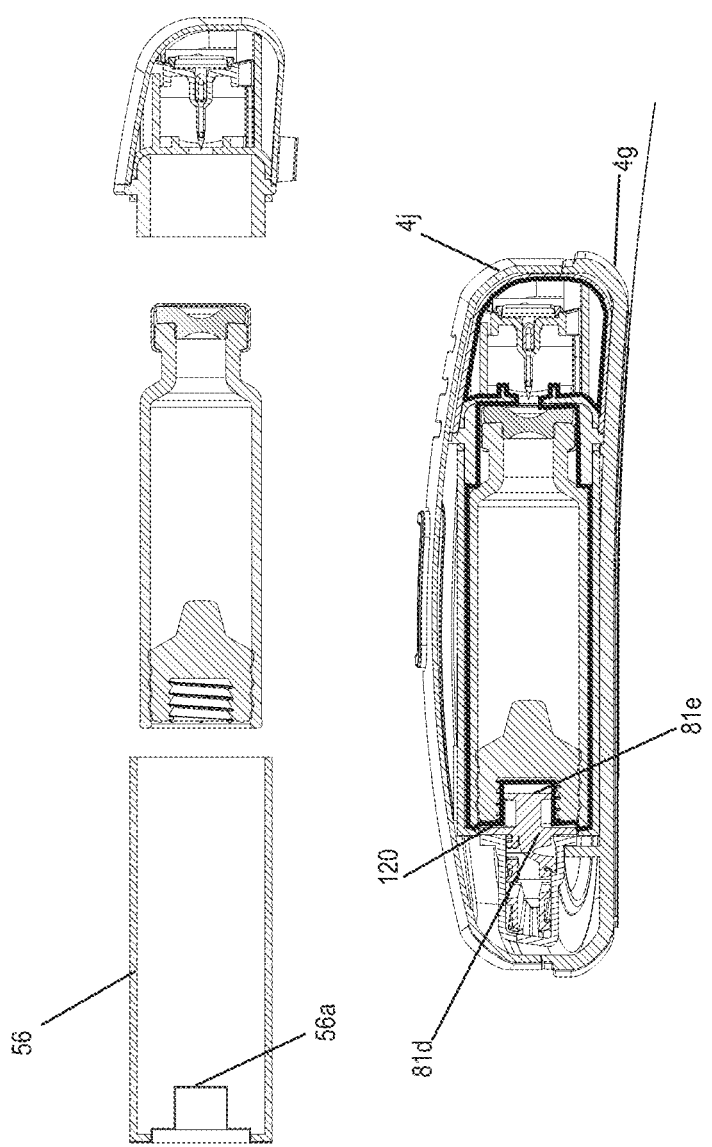

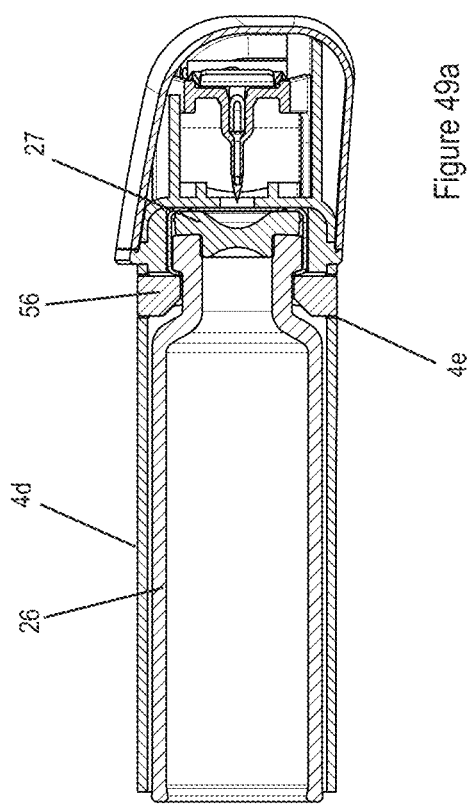

SEGMENTED PISTON ROD FOR A MEDICATION DELIVERY DEVICE

CROSS-REFERENCE TO RELATED APPLICATIONS

This application is a continuation of International Application No. PCT/CH2017/000052 filed May 24, 2017, which claims priority to European Application No. 1 617 5898.2 filed Jun. 23, 2016, the entire contents of all of which are incorporated by reference herein in their entirety.

FIELD OF THE INVENTION

Devices for delivery of medication to the patient which are adhered to the skin of the patient have been developed in the past, either for delivery of multiple adjustable doses superimposed on a basal rate (WO0240083A2), or for multiple fixed doses including a basal rate (WO11046950A1). Those devices have been preliminary developed for the treatment of diabetes. Alternatively, patch type of bolus injectors were developed also for the treatment of other diseases like cardiovascular diseases, auto-immune diseases or cancer for the delivery of a single dose as described in WO10029054 A1. Such a device is adhered to the patients' skin and activated automatically, or by the use of an activation button, or via a remote control system if the device is enabled to connect to other devices, and subsequently the single bolus volume will be injected. The term 'medicament" or "medication" includes any flowable medical formulation suitable for controlled administration through a means such as, for example, a cannula or a hollow needle and comprises a liquid, a solution, a gel or a fine suspension containing one or more medical active ingredients. A medicament can be a composition comprising a single active ingredient or a pre-mixed or co-formulated composition with more than one active ingredient present in a single container. Medication includes drugs such as peptides (e.g., insulin, insulin-containing drugs, GLP-1 containing drugs or derived or analogous preparations), proteins and hormones, active ingredients derived from—or harvested by—biological sources, active ingredients based on hormones or genes, nutritional formulations, enzymes and other substances in both solid (suspended) or liquid form but also polysaccharides, vaccines, DNA, RNA, oligonucleotides, antibodies or parts of antibodies but also appropriate basic, auxiliary and carrier substances.

BACKGROUND

Medical delivery devices in general or patch devices have different functionalities combined in one system. For example the patient first sets a dose which is subsequently delivered by a delivery mechanism. Prior to delivery it is required to insert a needle or cannula in a patient which is either done manually, or using a needle insertion and/or retraction system. After the delivery—especially for reusable devices, the drive mechanism needs to be reset. The different functionalities are required at different times during the injection procedure and therefore coupling systems are needed that couple and decouple the functionalities from another. Such a coupling can be a permanent coupling between two parts which are engaged and biased with respect to each other but transmit substantial forces or torques in one rotation direction only. An example is a one-way ratchet system which transmits rotation from one part to another in one rotation direction only. In the opposite rotation direction the two parts ratchet versus each other producing audible clicks, for example delivery clicks. A disadvantage of such a one way ratchet is that the ratchet system requires a certain torque to ratchet the system, e.g. at the cost of the efficiency of the device. As an alternative, for cases where the ratcheting and efficiency losses are not desired, axial shifts are required to open or close such a ratchet system such that the unidirectional coupling of the ratchet system is closed when the two parts are intended to rotate both in one direction and the coupling is open or decoupled so that the two parts can rotate with respect to each other. For axially shifting the two parts together, a gearing or threading engagement can be used as described in U.S. Pat. No. 9,107,999, where a piston rod is linearly advanced, and the front end of the piston rod is coupled to the stopper or plunger of a reservoir. The piston rod has an internal threading which matches an outside threading of a drive sleeve. Rotation of the drive sleeve linearly advances the piston rod which is prevented from rotation due to a form-fit engagement to the housing. With this arrangement, axial movement without rotational movements are allowed. The stopper or plunger in U.S. Pat. No. 9,107,999 is threadedly engaged with the front end of the piston rod, and since rotation of the piston rod is prevented, the reservoir with the plunger needs to be screwed manually onto the front end of the non-rotating piston rod. An aspect of the present device is therefore to provide a coupling mechanism which couples and decouples, preferably a ratchet system, but which also allows for relative rotation between the two parts in the decoupled state.

Medical delivery devices such as patch pumps, patch injectors or bolus injectors that are adhered to the skin of the patient have a needle insertion mechanism for insertion of a needle or a soft cannula into the skin of the patient for subcutaneous delivery of a medicament. Additionally, such a mechanism can be equipped with a needle retraction feature, to retract the needle, the soft cannula or steel cannula into the device before re being removed from the patient's skin. Such needle insertion mechanism either inserts first a steel needle together with a soft-cannula surrounding the steel needle and the needle is retracted prior to delivery of the medication through the soft cannula such as described in WO0240083 A2. Alternatively, a steel cannula is inserted in the tissue which is also used for subsequent delivery as shown in WO05002649 A1.

The insertion of the needle requires a linear stroke, for example of a holder that is attached to the needle or the cannula. The insertion is preferably done perpendicular to the skin of the patient and consequently the stroke length required for inserting the cannula occupies space in this perpendicular direction and locally increases the dimensions, e.g. thickness of the device as presented in WO13140395 A1. The increased dimensions for the linear stroke of the cannula insertion reduces the usability and wearing comfort of the device for the patient. In order to reduce the space required for the needle insertion mechanism, several solutions have been provided. In WO2011012465 A1, the needle holder is driven by a part that axially slides in a direction perpendicular to the surface of the patient or to the bottom surface of the injection device. The sliding part has a guiding means, for example a groove or notch oriented oblique to the bottom surface of the device and the needle holder is keyed both to the groove of the sliding part and to a linear guide present in the housing or a part attached to the housing. The linear guide is oriented perpendicular to the bottom surface and ensures vertical insertion of the needle. Horizontal movement of the sliding part thus drives the needle holder through the guiding means from a needle retracted to a needle inserted position. A further horizontal movement of the sliding part ensures that a second part of the guiding curve retracts the needle from the inserted to the retracted position. The fact that both insertion and retraction are driven by the sliding part implies that the horizontal movement occupies space which enlarges the lateral dimensions of the device.

Another space saving arrangement for a needle insertion and retraction mechanism is presented in DE102004059491 where a lancet device is presented having a rotating part with a sinusoidal guide curve applied the outside surface of the rotating part. The guide curve drives the needle from the top of the sinus to the bottom as the rotating part rotates over a first angle and therewith inserting the needle into a patient. Rotation of the part over an additional angle drives the needle from the minimum of the sinus back to the maximum and thereby accomplishes retraction of the needle. In WO15032747 A1, a needle insertion and retraction mechanism is presented based on a rotating drum having a sinusoidal shaped guiding curve designed as groove on the outside surface of the drum. It is therefore an aspect of the device presented here to overcome the drawbacks of the prior art insertion and retraction mechanisms.

The medication delivery device or patch device or patch pump delivers medication from a reservoir that is connected via a fluid path to the cannula for subcutaneous delivery to the patient. Medication is preferably delivered by advancement of a stopper or plunger present in the reservoir. The plunger is advanced by a drive mechanism advancing a piston rod. The piston rod can be made as still and linear piston rod, which is described in WO10029054 A1 for a skin attachable patch device, but the linear piston rod enlarges the lateral dimensions of the device leading to discomfort for the patient. Several solutions have been provided for a space efficient design of the piston rod using curved or bendable piston rods. Such curved piston rods are either made from a helical spring as shown in U.S. Pat. No. 6,474,219 or as a segmented piston rod, with separate elements that are connected to each other via a hinge as shown in WO04056411 A3. Both In U.S. Pat. No. 6,474,219 and WO04056411 A3 the piston rod is driven from outside by a nut element which rotates to advance the segments of the piston rod. On the inside of the nut there is a threading engaging an external thread on the outside of the segments of the piston rod. Once the segments are axially aligned and abut each other, an axial force can be transmitted by the stacked segments to the plunger of the reservoir. The last segment abuts the plunger to expel medication from the device and needs to be guided into the reservoir to ensure correct and plane abutment of the plunger and to prevent blockage of the piston rod in the reservoir. Therefore, the nut element driving the segmented piston rod is located close to the opening of the reservoir as in WO07038059 A3 which requires that the drive train is arranged close to the reservoir. As an alternative, the first segment, which is furthest away from the reservoir is driven by a nut element as presented in WO9509021 A1, however this requires a stable configuration of the last segments) entering the cartridge. In WO 0183008 A1 the Innolet device, this is solved by stiffening the hinge between the last two segments or by lengthening the length of the last segment as in WO04056411 A3. The disadvantage of lengthening the non-flexible part of the flexible piston rod is that more space is required to bring the piston rod into the position for expelling medication from the device. A longer, rigid portion of the piston sticks out of the open end of the reservoir before the piston rod can be flexed for connection to the drive mechanism. It is therefore an aspect of the present device to provide an alternative, more space saving configuration of a piston rod that is driven by the first segment and enables a reliable entrance of the last segment into the reservoir.

It is therefore an object of the invention to provide an alternative, more space saving configuration of a piston rod that is driven by the first segment and enables a reliable entrance of the last segment into the reservoir.

SUMMARY OF THE INVENTION

The medication delivery device is shaped such that it can be adhered to the skin of a patient, e.g. it preferably has a planar or slightly curved or anatomically shaped bottom surface with an adhesive layer which provides the attachment to the skin of the patient. A patient removes the device from a packaging and removes a protective layer from the adhesive layer prior to attachment. The medication delivery device preferably has an optical indication means which can indicate to a user that the device is ready for injection, with or without a delay time for equilibrating the device and medication to the ambient temperature if the device is taken out of the cold-chain storage conditions. The device preferably has a separate button for starting the device which can be on a top cover of the device or a switch is present on the bottom surface and skin attachment activates the device. As an alternative, also the release of the protection foil for the adhesive can activate an electrical circuit but the start medication delivery is only enabled after attachment to the skin. The control system of the device is such that the medication cannot be delivered before attachment to the skin. Yet another alternative has the option that a sensor, preferably a capacitive sensor is part of or activates the electrical circuitry or the sensor signal is processing by a processing unit which controls the device. The capacitive sensor can be directly present on the bottom surface of the device, below the adhesive layer, for example the capacitive sensor is printed on or attached to the housing of the device. Alternatively, the capacitive sensor is embedded in the carrier foil or supporting film of the adhesive layer. In yet another alternative, the capacitive sensor is attached or glued onto the carrier film or supporting film of the adhesive layer. In yet another alternative, the capacitive sensor is embedded in the adhesive layer or glue itself.

Alternatively, the sensor is part of the housing or positioned inside the housing. The sensor measures a difference in capacity between a non-skin adhered and skin adhered position for device activation (e.g. power the electrical circuit) and/or start of the medication delivery by the delivery mechanism. In all options presented, at least one time delay preferably exists between the removal of the device from the cold-chain, the activation of the electrical circuit, and the start of the medication delivery. The signals from the switches and/or sensors are sent to the processor and depending on the set-up of the software, different time delays can exist depending on the temperature of the device and/or medication, or time from the activation of a switch or command from a separate device. The processing unit of the device can be programmed such, as to prevent the activation of the activation button before a certain waiting time or temperature has been reached, in yet another alternative, the processing unit of the device can be activated and/or controlled via a remote control system such as a Bluetooth connection or another wireless network connection (WLAN) or via an RFID or NFC chip.

The optical indicator, for example a LED light, can give different color signals and/or different lighting sequences depending on the status of the device, e.g., not ready for delivery, delivery of medication, delivery finished, needle retracted, and ready for removal from the skin. The status signals can also be sent in parallel to an external device like a cellular phone using an internal transmitter/receiver unit. The housing of the medication delivery device is preferably composed of a bottom and a top cover, the bottom at least having the skin adhesive layer and a passage for the needle or cannula. The top cover preferably has at least a viewing window for viewing the reservoir containing the medication.

The device can be subdivided in several modules or sub-units:
- A drive mechanism comprising the control unit: The unit is powered, preferably by a battery and contains the processor for controlling the device. Furthermore the drive mechanism for advancing the piston rod comprises a motor, gearing and coupling mechanism.
- A top cover comprising, preferably, a button and a viewing window.
- A fluid path unit: This unit comprises the mechanical parts for the needle insertion and retraction mechanism, a cannula and a spike which are connected to each other via a tubing. A housing comprising a cartridge holder and a cartridge. The fluid path unit is a sterile part and the marriage of the fluid path unit with the cartridge is done under controlled sterile conditions, as will be described below.
- A bottom surface module comprising the bottom surface, preferably, a capacitive sensor an adhesive layer and a cover or peel foil for the adhesive.

The different sub-units can be assembled to form the device at different locations. For example, the fluid path can be assembled at factory A, sterilized at location B whereas the assembly with the sterile cartridge is done at location C. Finally, the sterile fluid path unit containing the medication can be married with the drive mechanism, top and bottom subunits at location D.

The different sub-units in the device provide different functionalities which are either coupled to each other electronically and/or mechanically to provide a reliable and, from a patients perspective, easy functioning of the device.

After the injection is finished, the patient removes the device from the skin, the housing of the injection device and/or the adhesive layer, for example the carrier film of the adhesive layer, may be provided with grips or additional films or lips intended for easy skin removal.

The injection device, preferably a bolus injector or patch injector comprises a housing having a first compartment with a drive mechanism comprising a motor, a gearing mechanism and a piston rod that advances a plunger in a reservoir or cartridge, and a second compartment with the fluid path which can connect the contents of the reservoir to a needle or a cannula intended for delivery. The latter compartment has a needle insertion and retraction mechanism and this needle insertion and retraction mechanism is either permanently coupled to the drive mechanism or selectively coupled to the drive mechanism during the insertion and retraction procedure. For the permanent coupling the drive mechanism is preferably coupled to the insertion and retraction mechanism using a one way ratchet whereby rotation of the drive mechanism in one rotation direction advances the piston rod. In that rotation direction, the one way ratchet system is designed such that the insertion mechanism is not coupled to the drive mechanism. The one way ratchet system, preferably shaped as asymmetric toothings formed directly or indirectly on parts functionally positioned between the drive mechanism and the insertion mechanism, slide and ratchet over each other without a transformation of a torque required to activate the insertion mechanism. The one-way ratchet can be designed as an axial ratchet or as a radial ratchet in the axial ratchet, the ratcheting element such as the asymmetric teethings, point in a direction along the rotation axis. In a radial ratchet, the ratcheting element such as toothings or flexural arms point in the radial direction. Rotation of the drive mechanism in the opposite direction ensures that the asymmetric toothings are pressed into a form fit arrangement such that rotation of the drive mechanism is transmitted to the insertion mechanism and the insertion mechanism or retraction mechanism is activated. The coupling between the drive mechanism and the insertion mechanism is permanent and preferably biased by an elastic spring means. A rotation of the drive mechanism is transmitted to the needle insertion mechanism in one direction only. In the opposite rotation direction the ratchet mechanism ratchets and produces audible clicks indicating to the patient that the medication is being expelled from the device. After the medication has been expelled, the rotation direction of the drive/gearing mechanism is reversed once again to initiate the needle retraction mechanism of the device. In another aspect of the coupling mechanism, the drive mechanism is selectively coupled to the needle insertion and retraction mechanism during the needle insertion and retraction sequences only, and the drive mechanism is decoupled from the insertion mechanism during dose delivery.

This coupling and decoupling mechanism is embodied in a housing, preferably the first compartment, comprising a first part having a longitudinal axis, which is axially fixed with respect to the housing and rotatable around the longitudinal axis, the first part having a gearing engagement, preferably a threaded engagement, to a second part which is arranged along the longitudinal axis. The gearing engagement between the first part and the second part, preferably the threaded engagement, has a first frictional resistance or friction that needs to be overcome to move the two parts relative to another, by rotation and/or axial translation. The gearing engagement can also be a helical gearing between two toothings with an angle oblique to the rotational axis. The frictional resistance between the two parts depends on the fit between the engaging elements of the two parts, the tolerances, surface topography of the interacting surfaces, type of materials selected and the presence or absence of any lubricating agents such as a silicone oil or Teflon spray. The second part is axially moveable along the longitudinal axis of the first part, preferably the axis of the first part and second part are aligned with respect to each other. Furthermore, the second part is directly or indirectly in a friction fit engagement with respect to the housing, the friction fit engagement having a second frictional resistance. This in contrast to the form fit arrangement as described in the prior art of U.S. Pat. No. 9,107,999 for advancing a piston rod; the friction fit arrangement enables axial shifts, and relative rotation between the first part and the second part whereas a form fit would only allow axial shifts without rotation.

The second frictional resistance is defined by comparable parameters as described above for the first frictional resistance. The coupling and decoupling mechanism is further defined by that the first frictional resistance is below the second frictional resistance, such that a rotation of the first part in a first rotation direction axially moves the second part away from the first part along the longitudinal axis, this being caused by the threaded or gearing engagement between the two parts. During the axial shift, the second part is prevented or at least restricted from rotation due to the friction fit to the housing. Thus during the axial shift the second part either only shifts without rotation or performs a combination of an axial shift and rotational movement. A rotation in a second rotation direction of the first part, which is opposite to the first rotation direction, reduces the axial distance between the first and second part. Once the end of the engaging elements between the first and the second part has been reached, e.g. once the end of the threaded engagement has been reached, the first part and the second part rotate in unison without axial movement, this occurs in one position where the first and second part are moved apart, and cannot be moved further apart due to the end of the threaded or gearing engagement and when the two parts abut each other at the other end of the threaded or gearing engagement. The reduction of the axial distance between the second part and the first part can, preferably result in an axial or radial abutment of the first and second part, or the second and first part can get into a coupling engagement for rotation in unison. Thus rotation in a first rotation direction of the first part axially moves the second part away from the first part until no further axial movement is allowed by the engagement, and the second part co-rotates with the first part and the friction fit engagement does not prevent this rotation, this in contrast to a form fit engagement to the housing. Reversal of the rotation direction implies that the second part axially returns back to the first position until no further axial movement is allowed or the second part abuts the first part and the second part is forced to rotate together with the first part in the second rotation direction.

The coupling mechanism has a threaded or gearing engagement between the first part and the second part and is designed as at least one thread segment present on the first part engaging at least one thread follower present on the second part or as at least one thread segment present on the second part engaging at least one thread follower present on the first part. The thread segments and thread followers each have lengths and once the end faces of the threads or thread segments, preferably radially, abut each other, then a relative rotation and/or axial shift is prevented and the first part and second part rotate in unison. As an alternative, the gearing engagement between the first and second part is a helical gearing, whereby a change of rotation direction of the first part axially shifts the second part to couple or decouple the second part.

The second part is directly or indirectly coupled to the housing via a friction fit engagement, the second part can rotate and/or axially slide with respect to the housing if the second frictional resistance or a threshold frictional resistance has been overcome.

The friction fit engagement can exist directly between the second part and the housing and is, for example, exerted by at least one O-ring, at least one flexural element or a friction coupling. This friction fit engagement can also form a sterile barrier, preferably between a compartment containing the needle insertion mechanism and the drive mechanism. Alternatively, the friction fit engagement of the second part is realized by an indirect engagement to the housing, for example via a third part that is axially fixed with respect to the housing and rotational free arranged along the longitudinal axis, the third part being in a second friction fit engagement with the housing having a third frictional resistance. This third frictional resistance is above the second frictional resistance for a correct functioning of the opening and closure of the coupling. Thus the first part is an engagement with the second part having a first frictional resistance which is below the second frictional resistance between the second part and the third part which is again below the third frictional resistance between the third part and the housing. The cascade of friction fit engagements can be designed such that they all, or at least one of them, form a sterile barrier, preferably between the needle insertion mechanism or a compartment containing a fluid path and the drive mechanism.

In one example, the first, second and third part are designed as concentrically arranged sleeves and the third part surrounds the first and second part, thus the third part has an inner dimension, preferably a circular shape, which fits around the first and second part. The arrangement of the first and second part can be such that the second part surrounds the first part or vice versa the first part surrounds at least partially the second part. The third part and its second friction fit engagement to the housing preferably form a sterile barrier. The sterile barrier can be designed as a form fit engagement or a press-fit engagement such that the third part is allowed to rotate with respect to the housing without any axial movement. The sterile barrier is preferably formed between the first compartment preferably containing the drive mechanism and a second compartment with the needle insertion mechanism. Alternatively, the second friction fit engagement forms a sterile barrier between the ambient surrounding a subassembly of the device containing the insertion mechanism, and the outside. The sterile barrier can be formed by the fit of the two elements directly or via a separate element, for example the housing or a part of the housing is encapsulated with an elastomer covering the border between the third part and the housing. The elastomer, preferably a TPE is preferably injection molded around the housing or a part of the housing using 2-component injection molding techniques. Alternatively an O-ring can be the separate element for providing a sterile barrier.

In another aspect of the coupling mechanism, the second part is preferably arranged along the longitudinal axis of the first part between the first part and the third part. Thus the longitudinal axis of the first, second and third part are preferably identical for all parts. The second part is moveable towards the third part once the first part is rotated in the first rotation direction, and the second part is moveable towards the first part once the first part is rotated in the second rotation direction. The movements are caused by the combined interaction of the cascading frictional resistances and the threaded engagement between the first and second part. The second part and third part form a one way clutch or coupling, preferably a one-way ratchet system which is closed once the second part abuts the third part and the first, second and third part co-rotate in the first rotation direction. Once the first part rotates in the first rotation direction, the second part axially approaches the third part until the one way coupling is closed and the first, second and third part rotate together. If the first part is subsequently rotated in the second rotation direction, the second part moves axially away from the third part towards the first part thereby opening the coupling. Once the second part abuts the first part, the first and second part both rotate in the second rotation direction. In the alternative described above, a permanent one-way clutch or ratchet exists between the second part and the third part, e.g. without the axially moving second part that is driven by the first part. In that example, the one way clutch is permanently closed or biased by a spring means and rotation in the first rotation direction ensures that the first, second and third part rotate in the first rotation direction. Rotation in the second rotation direction ensures that the second and third part ratchet over each other whereby the second part rotates and the third part is in such a frictional resistance or fit with respect to the housing that the parasitic torque of the ratchet system is below the frictional engagement of the third part to the housing. A rotation of the third part by closing of the coupling mechanism is used in the present invention to activate a needle insertion and/or needle retraction mechanism. Rotation of the third part in the first rotation direction ensures, via a coupling, preferably designed as at least one cam interacting with another part, preferably a needle control element, that the needle control element rotates over a first angle together with the first, second and third part. Rotation of the needle control element over the first specific angle ensures that the needle insertion mechanism is activated and a needle cannula holder moves from the needle retracted to the needle inserted position. During a further rotation in the first rotation direction of the third part, which can be directly after the first rotation in the first rotation direction, but alternatively also after the first part has been rotated over a certain number of revolutions in the second rotation direction, the third part is rotated over a second angle in the first rotation direction, and ensures that the needle control element is rotated and/or translated to activate the needle retraction mechanism.

In a further aspect also a method is presented having a certain sequence of rotation and coupling steps. Preferably first, the first part is rotated in the first rotation direction to close the coupling between the second and third part and rotate the needle control element over a first angle to activate the needle insertion mechanism. Subsequently, the first part is rotated in the second rotation direction whereby the coupling is opened and a piston rod is advanced to expel medication from the reservoir. Once the reservoir has been emptied, the rotation direction of the first part is reversed to the first rotation direction again and the coupling between the second and third part is closed again and the needle control element is rotated over a second angle to activate the needle retraction mechanism.

An additional step to the method of coupling a drive mechanism to a needle insertion and retraction mechanism can be added prior to the first closing of the coupling for activating the needle insertion mechanism. The medication delivery device preferably comprises a reservoir with the medication and the medication is delivered by advancing the plug or plunger present in the reservoir. The advancement of the plunger is accomplished by advancing a piston rod by the drive mechanism. If there is an axial gap between the end of the piston rod and the plunger, it is advantageous to first advance the piston rod by rotating the drive mechanism in the second rotation direction before activating the needle insertion mechanism, which requires a rotation of the drive mechanism in the first rotation direction. Thus the additional step comprises rotating the first part in the second rotation direction to activate the drive mechanism for advancing the piston rod towards the plunger present in the reservoir containing the medication, prior to rotating the first part in the first rotation direction to close the one-way clutch between the second part and the third part. The gap between the end of the piston rod and the plunger can be due to the use of a non-completely filled reservoir. The first advancement of the piston rod can be done in the factory during assembly with the reservoir or afterwards by the patient during use.

The first part is either directly coupled or coupleable to the motor of the drive mechanism or the first part is coupled to the motor of the drive mechanism via a gearing arrangement. In the first option, the motor of the drive mechanism drives the first part via a unidirectional ratchet system, e.g. rotation of the motor in one rotation direction results in a rotation of the first part whereas rotation of the motor in the other rotation direction activates the ratchet, or alternatively a ratchet and pal mechanism such that the first part does not rotate but the ratchet mechanism produces audible clicks. The motor of the drive mechanism uses a separate gearing mechanism for activating the drive mechanism for advancing the piston rod. In the second option, both the first part and drive mechanism for advancing the piston rod are permanently coupled to a single gearing mechanism and rotation of the motor in both rotation directions results in a rotation of the first part and/or rotation of the drive mechanism for the advancement and/or retraction of the piston rod. The gearing mechanism in the first and second option for rotation of the first part can be accommodated to include a no-load stroke before the first part is forced to rotate.

The medication delivery device comprising the coupling mechanism described above preferably is a bolus injector, a patch injector or a patch pump.

The coupling and decoupling mechanism of the above describes the coupling between a drive mechanism and a needle insertion and retraction mechanism. The needle insertion and retraction mechanism and a method for coupling the drive mechanism to the needle insertion mechanism is described in the following for 3 embodiments of the medication delivery device.

It is an aspect to present a needle insertion and retraction mechanism for a medication delivery device for delivering a medicament from a reservoir having a septum, the delivery device having a housing with a bottom surface attachable to the skin of a patient. The reservoir preferably being an ampoule or a cartridge that is filled with a medicament. The cartridge preferably being a cylindrically shaped tube closed on one side by a plunger and on the opposite side by a septum suitable for being punctured by a spike, whereas the medication is located between the plunger and the septum. The reservoir has a longitudinal axis which is preferably oriented parallel to the bottom surface of the device (or the skin surface of the patient) for a space saving arrangement in terms of thickness of the device. The medication delivery device having further a spike inserter carrier comprising a spike for insertion through the septum of the reservoir, the spike inserter carrier being moveable parallel to the bottom surface between a first position where the spike does not penetrate the septum to a second position where the spike penetrates the septum. The spike inserter carrier being biased by a biasing means which intends to move the spike inserter carrier from the first position towards the second position. The biasing means can be, for example, a spring means, a compression spring a coil spring, a wave spring, a leaf spring or the like. Further the needle insertion and retraction mechanism comprises a cannula holder for holding a needle or steel cannula, the cannula holder being guided in the housing for a linear movement perpendicular to the bottom surface between a needle retracted position and a needle inserted position. As an alternative, the cannula holder is guided by the housing for an inclined insertion, e.g. at an angle to the normal (e.g., normal axis) of the bottom surface which can further reduce the height of the device. The needle retracted position being furthest away from the patients skin and the needle inserted position is defined by the cannula position for, preferably, subcutaneous delivery. The cannula holder is, for example, injection molded around the cannula and preferably made from a polymeric material. The spike inserter carrier has a drive means, preferably a first guiding means, for driving the cannula holder from the needle retracted to the needle inserted position. The cannula holder preferably has a transformation means which is engaged with the first guiding means, such that the biasing means biases the cannula holder for moving from a needle retracted towards the needle inserted position. Furthermore, a needle control element is part of the insertion and retraction mechanism, whereby the needle control element has an arrester or stop which directly or indirectly abuts the cannula holder, or a part attached to the cannula holder, and which holds the cannula holder in the needle retracted position against the force of the biasing means which biases the spike inserter carrier. The needle control element thereby preventing the movement of the spike inserter carrier from the first position towards the second position since the cannula holder and the spike inserter carrier are engaged with each other via the first guiding means and the transformation means. The arrester of the needle control element therewith also blocks the cannula holder from moving from the needle retracted to the needle inserted position.

A fluid path, preferably shaped as a flexible tubing is positioned preferably between the cannula or cannula holder and the spike of the spike inserter carrier such that a fluid connection exists between the spike and the needle. The spike inserter carrier is laterally guided in the housing by at least one guide slot, preferably a horizontal linear guide, a channel, a groove or protrusion present on the housing or a part of the housing, for example the bottom surface and/or top cover, or the spike inserter carrier is keyed to a subassembly or a housing part, for example to a fluid path unit. The maximum lateral position of the spike inserter carrier sliding through the housing is provided by stops and counterstops present on the carrier and/or the housing. Low friction materials and/or lubricants are selected to reduce the frictional losses between the spike inserter carrier and the housing. The spike and spike inserter carrier are preferably designed as being made in one step from a single material, preferably via an injection molding process. The spike of the spike inserter carrier is designed as a hollow cylinder having a sharp tip or ending. The side opposite to the tip is attached or attachable to the bottom surface of the spike inserter carrier. The tip is designed for penetrating the septum of the reservoir and therefore requires that the material for the spike and/or spike inserter carrier is a stiff material, for example a high modulus polymer such as PEEK, PPSU, POM or a fiber reinforced polymeric material. As an alternative, the spike is made from a metal which is attached to the bottom surface of the spike inserter carrier in a separate production step. The spike has a longitudinal axis which is preferably arranged parallel to the longitudinal axis of the reservoir with the septum. As an alternative, the reservoir is reversed in the device such that the spike of the carrier penetrates the plunger of the reservoir instead of the septum. In either arrangement, the system is designed that after penetration of the septum or plunger, the medication can flow from the reservoir, through the spike via the tubing to the cannula. The spike inserter carrier is guided, preferably by the housing to perform a linear movement which is preferably parallel to the longitudinal axis of the reservoir and preferably the longitudinal axis of both the reservoir and the spike are aligned with respect to each other such that the septum of the reservoir is punctured in the center.

The biasing means for biasing the spike inserter carrier is positioned preferably between the housing or a housing part and the spike inserter carrier such that the carrier intends to move from the position which is furthest away from the septum (or as an alternative from the plunger) towards the septum penetrated position. The biasing means is a spring, a magnetic biasing means, an electromagnetic biasing means, a pyrogenic driven biasing means or a gas driven biasing means. After release of the biasing means, a force is transmitted from the biasing means to the spike inserter carrier which subsequently ensures that the septum or plunger is penetrated. The stop position is either defined by abutment of the base of the spike inserter carrier or base of the spike with the septum, or by a separate stop present on the housing.

The spike inserter carrier comprises the driving means or first guiding means, which is preferably designed as a linear guide for guiding and/or biasing the cannula holder via the transformation means. The transformation means is preferably designed as a protrusion which fits into the linear guide of the driving means. The linear guide is arranged oblique to the bottom surface of the carrier or housing such that a lateral movement of the spike inserter carrier exerts a downward movement for the cannula holder towards the skin of the patient. The inclination angle of the linear guide with respect to the normal of the bottom surface varies between 20° and 80°, preferably between 30° and 70°, more preferably between 40° and 60°. As an alternative, the driving means is shaped as a non-linear curve, for example as an "S" shaped curve to control the insertion speed and/or force of the cannula holder.

Preferably, for moving the cannula holder from the needle retracted to the needle inserted position, it is required to release the biasing means and activate the driving means of the spike inserter carrier. In order to achieve this, the needle control element is rotated over a first angle such that the abutment between the arrester of the control element and the cannula holder is released. This ensures that the spike inserter carrier is allowed to move from the first position to the second position, driven by the force of the biasing means, and thereby the driving means simultaneously moves the cannula holder from the needle retracted to the needle inserted position. The movement of the cannula holder towards the inserted position ends once the cannula holder abuts a second arrester which can be positioned on the housing, a part attached to the housing, the bottom of the housing but also on the needle control element.

The needle control element preferably has a locking mechanism which locks the cannula holder in the needle inserted position once the needle control element has been rotated over the first angle. The locking mechanism prevents that during injection the needle retracts or can be moved by external forces from the needle retracted to the needle inserted position. The locking mechanism is preferably designed as at least one locking arm or latching element present on the needle control element. The part attached or attachable to the locking arm can match a corresponding part, a catch, a cut-out, a flex-arm or latching element present on the cannula holder. The parts are designed such that a movement towards the needle inserted position activates the locking mechanism, for example by arms that flex into a locking position. Preferably, the end of a locking arm ends in a tip that matches a recess present in the cannula holder.

For retraction of the cannula, the cannula holder must move from the inserted back to the retracted position. Preferably the needle control element ensures needle retraction and the release of the locking mechanism described previously. The needle control element is preferably rotated further and/or translated in the same direction whereby the needle control element has a needle retraction means. The needle retraction means is preferably designed as a needle retraction arm, which abuts the cannula holder once the needle control element rotates over a further angle above the first angle while releasing the locking mechanism and driving the cannula holder from the needle inserted position back to the needle retracted position. Alternatively the needle retraction means is not present on the needle control element but designed as a resilient element, for example a spring means present in the linear guide of the housing which is biased or strained by the movement of the cannula holder from the needle retracted to the inserted position. In the latter case, latching elements fixate the needle cannula holder in the inserted position and the needle control element releases this engagement during the further rotation above, or at a greater angle than the first rotation angle.

The needle insertion is preferably activated or powered by the first guiding means or linear guide of the spike inserter carrier which is sloped with respect to the bottom of the device. Once in the inserted position, a second guiding means which is adjacent to the guiding means becomes available for the transformation means of the cannula holder. The lateral movement of the spike inserted carrier is halted such that the second guiding means, which is connected to the first guiding means becomes available for the transformation means. The retraction of the needle is not powered by a further lateral movement of the spike inserter carrier since this would occupy more lateral space and additionally the spike that penetrated the septum prevents any further lateral movement of the carrier. Therefore the retraction of the cannula is powered by a different means which can be a spring means or the needle control element which pushes or draws the cannula holder back into the needle retracted position. The second guiding means preferably is a guide slot which guides the cannula holder preferably vertically back to the starting position. The spike inserter carrier has a second guiding means, preferably adjacent to the first guiding means, preferably designed as a linear guide slot oriented parallel to the normal of the bottom surface, which linearly guides the cannula holder back to the needle retracted position. The housing or a part attached to the housing can also have a linear guide slot preferably oriented parallel to the normal of the bottom surface which guides on its own or in combination with the second guiding means the cannula holder during needle retraction.

The needle control element is preferably keyed to or engaged with the housing to allow for rotations and/or translations of the needle control element with respect to the housing or a housing part, for example a wall arranged perpendicular to the bottom surface of the device. Therefore, the housing or housing part has at least two guiding means, a third and fourth guiding means preferably designed as third and fourth guiding slots which match at least two corresponding keys, preferably protrusions present on the needle control element. Preferably the keys protrude from the surface of the needle control element and the third and fourth guiding means are designed as grooves in the housing. The longitudinal axes of the guiding slots are preferably oriented at an angle with respect to each other. The needle control element is preferably driven by rotating a third part having engagement means, preferably at least one cam or gear-wheel which is in engagement with the needle control element. A rotation of the third part around its central axis results in a rotation and/or translation of the needle control element as the at least two keys pivot and/or move in the at least two guiding means. The rotations and combined translations are controlled by varying the centre of rotation of the needle control element due to the different interactions between the engagement means of the third part and the needle control element. The needle control element itself has a guiding element, preferably a guiding contour or guiding slot, which interacts with the at least one cam or gear wheel of the drive mechanism, preferably with the third part. Thus preferably, the guiding contour is shaped as a non-linearly curved opening penetrating the surface of the needle control element. In a preferred embodiment the two keys protrude from the surface of the needle control element and the guiding contour penetrates the same surface of the needle control element. Preferably the at least one cam or gear wheel of the drive mechanism engage with the guiding contour of the needle control element. The guiding contour is preferably formed as a closed or partially open non-circular loop or curve. The surface of the contour can be smooth but can also comprise a toothing, in the latter case, the interaction between the cams and the contour is a gearing engagement between two engaging toothings.

Each of the at least one cam of the drive mechanism or third part can interact with a different part of the guiding contour of the needle control element depending on the angle of rotation of the drive mechanism or third part. The different cam-guide contour interactions enable a variation of the center of rotation, or to control the force vector acting upon the needle control element such that preferably one key of the needle control element initially rotates in one of the two guiding means followed by a combined rotation and axial translation of both keys in the guiding means. The third part is coupled to or coupleable to the drive mechanism using the coupling mechanism described previously.

In a preferred embodiment the first key only rotates in the third guiding means whereas the second key axially slides in the fourth guiding means. This first rotational step corresponds preferably to the needle insertion step. In a second step, corresponding to the needle retraction, the first key and second key both axially translate through the guiding means and due to the angle between the third and fourth guiding means, the needle control element is forced to rotate and translate further over a further or second angle.

The needle control element is preferably rotated and/or translated by the third part preferably having at least one cam which interacts, preferably with the guiding contour of the needle control element. The drive mechanism for rotating the third part comprises an electromotor, a gearing, preferably including a worm wheel arrangement to reduce the number of revolutions of the treaded rod and increase the torque that can be transmitted. Alternatively, other power packages can be used for the drive mechanism such as gas driven systems, springs, electromagnetic drive trains and the like.

For insertion and retraction of a needle of a medication delivery device having the needle insertion and retraction mechanism described above, a method is presented comprising the steps of:

a) Rotation of the needle control element over the first angle to release the abutment between the arrester and the cannula holder to move the cannula holder from the needle retracted to the needle inserted position, and simultaneously insert the spike into the reservoir, b) Injection of the medicament present in the reservoir via the fluid path using the drive mechanism of the medication delivery device, c) Rotation and/or translation of the needle control element over a further angle to move the needle from the needle inserted position back to the needle retracted position.

The method may also comprise the coupling sequences for coupling the drive mechanism to the needle insertion mechanism; preferably before step (a), the coupling mechanism needs to be closed and the first part rotates in the first rotation direction, thereby moving the second part to the third part, the third part preferably having the cams that interact with the guide contour of the needle control element. The movement of the second part couples the second part to the third part and the one-way ratchet is closed. The third part also rotates the needle control element in the first rotation direction over a first angle to release the arrester of the needle control element from the cannula holder and initiate step a) of the method. Preferably for step b) of the method, the rotation of the first part of the coupling mechanism is reversed to the second rotation direction and consequently the coupling is opened and the third part will not co-rotate with the first part leaving the cannula holder in the needle inserted position. The reversal of the rotation direction rotates a threaded rod which will advance the piston rod for medication delivery. Preferably after emptying the cartridge, step c) of the method is initiated, and the rotation direction of the drive mechanism is reversed to the first rotation direction again. The coupling mechanism between the first, second and third part is closed and the cams of the third part rotate and translate the needle control element such that the locking mechanism for the cannula holder is released and that the needle cannula holder is translated back to the needle retracted position, preferably by the needle retraction arm. In an alternative method, the drive mechanism is activated such that preferably prior to step (a), the piston rod advances without releasing the needle insertion mechanism to reduce an axial distance between the piston rod and the plunger or plug in the reservoir.

A second example for the needle insertion and retraction mechanism is described below. The needle insertion mechanism is suitable for an injection device for delivering a medication from a reservoir having a septum, the needle insertion mechanism being embodied in a housing having a bottom surface that is attachable to the skin of a patient. The mechanism has a steering drum having a rotation axis which can be parallel, perpendicular or inclined to the bottom surface. The steering drum is biased for rotation in one rotation direction by a biasing means, preferably a spring means, a magnetic or electromagnetic biasing means or by a motor. The steering drum has a guiding means, preferably a guiding slot on the walls extending parallel to the rotation axis, furthermore, the steering drum has a first and second arrester located on the walls extending parallel to the rotation axis. Preferably, the first and second arrester are radially pointing in the outward or inward direction and are preferably positioned at different angles and/or axial positions of the walls extending parallel to the rotation axis of the steering drum. The needle insertion mechanism has a cannula holder for holding a needle or cannula, the cannula holder being linearly guided by the housing and moveable from a needle retracted to a needle inserted position in a direction perpendicular or inclined to the bottom surface of the housing. The cannula holder being directly or indirectly coupled to the steering drum and/or guiding means by a transformation means, the transformation means preferably shaped as a linear protrusion present on the cannula holder and matching the guiding means. The guiding means is designed such, or preferably has an inclination angle with respect to the rotation axis of the steering drum, to bias or drive the cannula holder for moving from the needle retracted towards the needle inserted position.

The needle insertion and retraction mechanism has a stop means which abuts the first arrester such that the steering drum is prevented from rotating in the one rotation direction and consequently the needle cannula holder remains in the needle retracted position.

Preferably the needle insertion mechanism whereby the stop means is rotated over a first stop means angle which releases the abutment between the stop means and the first arrester such that the steering drum is rotated in the one rotation direction over a first angle by the biasing means until the second arrester catches the stop means. During rotation of the steering drum over the first angle, the cannula holder moves from the needle retracted to the needle inserted position and is driven by the interaction of the guide means engaging the transformation means.

The guiding means on the steering drum is preferably shaped preferably as a sinusoidal curve on the inside or outside wall that extends parallel to the longitudinal axis, whereby the transformation means follows the first part of the preferably sinusoidal shaped curve from the maximum to the minimum as the steering drum rotates over the first angle. The needle cannula holder moves due to the gearing engagement from the needle retracted to the needle inserted position.

The needle insertion mechanism preferably enables a further rotation of the stop means around its rotation axis, whereby the stop means is rotated further to a second stop means angle which is greater than the first stop means angle and which releases the abutment between the stop means and the second arrester such that the steering drum is rotated over a second angle due to the biasing force of the spring means. During the further rotation of the steering drum, the transformation means of the cannula holder follows the second part of the guiding means, preferably the sinusoidal curve from the minimum to the maximum and the cannula holder moves back from the needle inserted to the needle retracted position. During this movement, the cannula holder is linearly guided by the housing or by a part attached to the housing.

The needle insertion mechanism preferably has a gearing which is attached or attachable or connectable to the steering drum and arranged along the rotation axis of the steering drum, the gearing is preferably designed as a toothing or gear wheel, which engages a spike carrier, preferably having a matching second toothing. The spike carrier is, preferably linearly guided by the housing and moveable from a first spike carrier position to a second spike carrier position such that when the steering drum rotates over the first angle, the spike carrier is moved from the first to the second position. The spike carrier comprises a spike which penetrates the septum of the reservoir when the spike carrier moves from the first spike carrier position to the second spike carrier position. Preferably, the gearing is rotationally and axially fixed with the steering drum.

The gearing of the steering drum preferably comprises an arrester which abuts a second arrester, preferably designed on the housing or spike carrier and limits the rotation of the steering drum when the stop means is rotated over the second stop means angle and limits the rotation of the steering drum for not going beyond the second angle.

The stop means has at least one counter-arrester which can interact with the first arrester and/or second arrester of the steering drum. The counter-arrester is, preferably is a semi-circular arch or rim or half-moon shaped such that a rotation of the stop means over a first stop means angle releases the abutment between the first arrester of the steering drum and the counter-arrester, but the rotation over the first stop means angle ensures that the counter-arrester is within the path of rotation of the second arrester as the steering drum rotates and consequently can abut the second arrester. Thus the arch shaped counter arrester is rotated to release the abutment with the first arrester whereas the arch is within the line of rotation of the second arrester. The stop means with the counter arrester is, preferably attached or attachable to an axis and the axis is coupled or coupleable to a drive mechanism of the injection device. Preferably, the stop means is directly or indirectly coupled to the third part and the sequence of rotations in the first and second rotation direction, as described above for the first example, ensures that the stop means is coupled to the drive mechanism and rotated to release the needle insertion mechanism and the spike insertion mechanism. The cannula holder is moved from the retracted to the needle inserted position prior to delivery of the medication and moved from the needle inserted to the needle retracted position after delivery of the medication. During the movement of the cannula holder to the needle inserted position, the spike simultaneously penetrates the septum of the reservoir and remains inserted in the reservoir during retraction of the needle.

In the third example, the transformation means is a lever arm for guiding the needle cannula holder and the transformation means is engaged with a gearing mechanism present on the rotational axis of the steering drum. Alternatively, the transformation means is activated by a rotation of the steering drum by abutment of a protrusion or rim present on the steering drum with a protrusion or rim present on the lever arm.

The stop means blocks rotation of the steering drum after insertion of the needle. Preferably a first stop is present on the lever arm or lever arm mechanism which abuts with a counter stop on the steering drum such that the rotation of the lever arm is stopped in the needle inserted position. Further rotation of the steering drum after releasing the abutment between the stop means and the first arrester of the steering drum drives the engagement between the first stop on the lever arm and the counter stop on the steering drum, such that the lever arm is rotated back and drives the cannula holder from the needle retracted to the needle inserted position. Preferably, a gearing is attached to, or attachable to the steering drum for driving the spike inserter into the septum of the reservoir.

The drive mechanism comprises a piston rod for delivering the medication form the reservoir. In the examples presented, the piston rod is a segmented piston rod and/or bended or wrapped for a space saving configuration in the device, but also a rigid or straight or non-segmented piston rod configuration can be combined with the needle insertion and retraction mechanism presented.

An aspect of the medication delivery device is a segmented piston rod for delivering a medication from a reservoir having a plunger, the piston rod comprises multiple segments that each are joined together via a hinge located laterally of each segment or between adjacent segments. The piston rod can be bent by rotation of adjacent segments around the hinge or articulated in one direction such that subsequent hinges are opened to form a curved piston rod. Preferably, the segmented piston rod thus can be bent in one direction only. An axial force can be transmitted by the segmented piston rod to the plunger in the reservoir via the subsequent hinges of the segmented piston rod. When the hinges between subsequent segments are closed, the segments form a stacked or linear configuration for entry into the reservoir, the stacked arrangement prevents buckling of one or more segments of the piston rod. With the segmented and curved piston rod arrangement, a space saving arrangement of the piston rod in the device can be accomplished.

The segmented piston rod is preferably driven by a threaded rod that rotates and engages with at least the first segment of the segmented piston rod. The first segment of the segmented piston rod is defined as being furthest away from the last segment of the segmented piston rod, the latter contacts the plunger of the reservoir. The segmented piston rod is secured against rotation with respect to the housing around its longitudinal axis and the at least first segment of the segmented piston rod is equipped with an internal thread matching an external thread of a drive sleeve or threaded rod, wherein rotation of the drive sleeve or threaded rod by the drive mechanism advances the segmented piston rod towards the plunger of the reservoir. The segmented piston rod is preferably guided in the housing or a part connected to the housing such that the segmented piston rod is rotationally secured with respect to the housing. For example, the segments of the segmented piston rod have a non-circular cross section matching a guidance or passage within the housing or a part connected to the housing. Alternatively, each of the segments of the segmented piston rod has a groove, notch or wing matching a complementary protrusion or groove in the housing to prevent rotation of the piston rod.

The piston rod comprises multiple segments that are each joined together via a hinge, preferably a strap hinge located on one side, preferably the lateral side of each segment. The piston rod can be bent in one direction thereby opening subsequent hinges between the segments, while an axial force can be transmitted to the plunger when subsequent hinges are closed and the segments abut each other on the opposite side of the hinge. The last segment of the segmented piston rod abuts the plunger of the reservoir, preferably with a flange or a connector for connecting to the plunger of the reservoir. The last segment has a guiding element which guides the last segment in, or into, the reservoir, whereby the guiding element is designed for abutting the inner lateral wall of the reservoir and guide the last segment such that the normal of the element is parallel to the longitudinal axis of the reservoir. The reservoir preferably has a tubular or cylindrical shape and preferably is made from glass or a polymeric material. The normal of the last segment is defined as perpendicular to the plane that abuts the plunger. When the last segment enters the opening of the reservoir, the opening being defined on the side opposite to the septum, then the last segment can enter under an angle and initiate a so-called piston squeezing and block delivery of medication. Therefore and for correctly connecting to the plunger in the reservoir, the guiding element ensures that the normal of the last segment is parallel, preferably equal to the longitudinal axis of the reservoir. The guiding element can be guided by the housing or a housing part prior to entering the reservoir, e.g. already ensures that the last element correctly enters the opening of the reservoir. The guiding element protrudes from the last element towards the second to last element and is oriented parallel to the normal of the last segment. Preferably, the guiding element is shaped as a fin that is attached to, or attachable to the last element, and one side of the fin is parallel to the longitudinal axis of the reservoir when the last element is completely enclosed by the reservoir. During entry of the last element into the opening of the reservoir, the guiding element functions as a lever arm and thereby orients the flange of the last element parallel to the end surface of the plunger that is not in contact with the medication. Before entry, the fin can already be guided towards correct entry, preferably by the housing or by a housing part. The segmented piston rod for an injection device whereby the guiding element acts as a lever arm on the last segment and ensures that the normal of the last segment is parallel to the longitudinal axis of the reservoir when the last segment abuts the plunger of the reservoir. The fin of the last segment points towards the second to last segment, but is not directly engaged or coupled to the second to last segment, e.g. it does not interfere with the bending or articulation range of the hinge between the two last segments. The hinge between the last two segments ensures that the two segments can articulate around a hinge axis. The guiding element or fin pointing towards the second to last segment is preferably an integral part of the last segment, for example made as a monolithic part during injection molding. The guiding element or fin is preferably located opposite of the hinge and is preferably oriented perpendicular to the hinge axis of the last two segments. Once the segmented piston rod is in a stacked configuration after entry in the reservoir, also the segments not having a guiding element are preferably guided by the inner wall of the reservoir. The segmented piston rod thus can transfer axial loads via the hinges to the last segment abutting the plunger.

Preferably, the medication delivery device is controlled by a control unit having a processor. The control unit controls the several steps during the delivery process, e.g. the rotation direction of the drive mechanism. The device is activated by closing first the electrical circuit of the system which includes the control unit since the device is preferably not powered during shelf-life. The activation of the electrical system can be done by a remote control, a mechanical switch an RFID circuitry or a sensor such as the capacitive sensor. Alternatively the electrical circuitry is automatically switched and ready for delivery once the device is removed from its packaging or cardboard box or when the user removes the liner for the adhesive layer. The control unit gets inputs from sensors such as the capacitive sensor or switches, or temperature sensors to indicate that the device is ready for delivery, e.g. attached to the skin of the patient and can get started by the inputs from the sensors, or by a separate mechanical switch such as a button being present on the device, preferably in or on the top cover. The control unit can receive information from internal sensors such as a temperature sensor, the capacitive sensor, the electrical circuitry, pressure or the encoder of the electromotor in the drive system. The control unit preferably includes a timer or a clock. The processing unit, preferably is equipped with a sending/receiving unit to connect to other external devices such as smart phones or a remote control unit. The connection can be established, preferably, by a Bluetooth or more preferably Low Energy Bluetooth connection protocol. The processor thus can also react to inputs from external sensors or remote control devices or smart phones. The device can be operated without the external control unit as is, thereby only using switches and/or sensors present in the device. The sending and receiving unit and the remote control are complementary features. The data received by the processor are preferably stored in a storage medium, such as date, time, injection time, injection volume, temperature, time between removal from the cold-chain and start of delivery, any errors during delivery such as occlusion, the time lapsed between delivery of the medication and the needle retraction or removal of the device from the skin of the patient, number of revolutions of the drive system, rotation directions and the like. Those data can be sent from the device or storage medium of the processing unit to a cloud server or a smart phone. Thus the communication between the medication delivery device is either one-way whereby the device sends data without receiving signals or a two-way communication whereby the medical device communicates and receives commands or data from the external device or system such as a network. The communication with the external device or system follows a secured and encoded protocol to prevent interference with other external devices, e.g. not the preferred external device which preferably has been connected and allowed to communicate with the medication delivery device. In a preferred example, the device is approached by a device having an Near Field Control (NFC) chip, which can activate the main electrical circuitry and/or start the injection and/or start data transmission or communication. The data received from the device, either directly or indirectly via the cloud server can be used by the patient, a medical practitioner or a health care professional.

The medication delivery device is after production and assembly with the medication reservoir stored under cold conditions since most of the medicaments require cold storage before use to increase the longevity and guarantee the shelf-life time. The storage conditions can be in a freezer, e.g. below 0° C. or in in a refrigerator, which is slightly above 0°, e.g. 5°-8° C. This effects both the viscosity of liquid medications as well as the dimensional tolerances of the diverse components that mechanically interact in the device due to the different thermal expansion coefficients of the materials used. Generally, the viscosity of most medicaments, for example solutions containing large protein molecules retrieved from recombinant DNA techniques, increases as the temperature decreases. To compensate for this, the control unit of the device can adjust the speed of delivery depending on the temperature within the device, thus the rotational speed of the drive mechanism or change the gearing ratio such that cold medication is delivered at a lower speed and/or with a higher force for advancing the piston rod. Alternatively, the medication is heated prior to the start of the injection procedure. This can be accomplished passively by waiting for a certain time after removal from the refrigerator but also actively by a heating source present in, or surrounding the medical device. The medication in the reservoir can be heated by an infra-red source either present on the outside to heat the medication via the viewing window, or it is present on the inside. Heating sources used can be, but are not restricted to an IR source, a heating element surrounding the reservoir or the tubing or a heat exchanger encapsulating the tubing, microwaves, heater bags using exothermic crystallization or oxidation to generate heat. Also the battery itself can be used as a heat source to the medication and/or fluid path. The heat generated can be transferred to the reservoir or to the fluid path, e.g. in the latter case the medication is heated just prior to injection. In another example, the body heat of the patient is used to either heat the reservoir, the fluid path or an intermediate element.

The medication delivery device delivers the medication to the patient under aseptic conditions which means that the sterility of the fluid path unit and the connection to the cartridge during production and shelf-life must be guaranteed.

In a first example, the fluid path unit is produced and assembled, preferably in a clean-room environment, for example GMP EU classification Grade C. The fluid paths are packaged in a peel pouch or a blister, either individually or stacked in a tray or tub. Preferably, fluid path units are assembled in a tray that is put into a tub which is subsequently packaged in at least two-fold peel pouches. The peel pouches can be air tight for subsequent gamma sterilization or the peel pouches are made from gas-permeable membranes such as Tyvek, and subsequently sterilized using Ethylene Oxide or Gas Plasma Sterilization (for example H2O2, or NOx). The packaged tubs are shipped to a fill-finish company that brings the tubs with the fluid paths in an aseptic environment, for example GMP EU classification Grade A, by first removing the first peel pouch of the tub, sterilize the surface for example by using e-beam and bring the tub into the aseptic environment via a double-door system. The same track for entering the aseptic environment is followed for the empty and sterile cartridges that are also arranged in tubs enclosed in a double peel pouch. Also the cartridges are brought into the aseptic environment. The empty cartridges are then aseptically filled and stoppered in the aseptic environment and finally assembled with the fluid path units in an aseptic environment. The sterile fluid paths can now be assembled with the drive mechanism, bottom and cover sub-units outside the aseptic environment.

In a second example, the same path is followed, except for the fact that the sterile fluid path units in the tubs are shipped to the company producing the reservoirs or ampoules. That company enters the tubs into their aseptic environment after removing the first pouch and sterilizing the tub after unwrapping, and inserts the empty cartridges into the fluid path. The fluid paths in the tubs are packaged and sterilized again and shipped to the company doing the aseptic filing in an aseptic environment. After filing, the sterile fluid paths are ready for assembly outside the aseptic environment, for example in the clean room.

In the first two examples, the reservoir and the fluid path unit are both sterilized before entering the aseptic environment and are assembled in the aseptic environment which means that the space between the spike and the septum of the reservoir is also sterile. In the last example, the reservoir and the fluid path unit are both assembled in a different class environments and after assembly of the two, the space between the septum of the reservoir and the spike is sterilized in a separate step. In the third example, the fluid path is preferably assembled in a clean room environment and the reservoirs are filed in an aseptic environment. The two are assembled in a clean room environment which implies that the interspace requires an additional sterilization step, for example using ETO or Gas Plasma sterilization, the housing part is designed such that the intermediate space can be sterilized in a separate and preferably final step, for example using ETO or gas plasma sterilization.

A medical device for injection medication from a reservoir having a septum which is attachable or attached to the skin of a patient which comprises:

A fluid path comprising a spike for insertion through the septum of the reservoir, a cannula holder for holding a cannula or needle for insertion into the patient and a tubing for a fluid connection between the spike and the cannula holder, the fluid path being enclosed in a sterile enclosure during shelf life of the medical device, A fluid path housing enclosing the fluid path and having at least one passage for the needle or cannula, A bottom surface which is either part of the fluid path or a spate part, the bottom surface having an adhesive layer for mounting to the skin of the patient, whereby during injection of medication the cannula or needle and/or the spike communicates with the outside of the sterile enclosure, characterized in that the sterile enclosure at least partially encloses the adhesive layer during shelf-life. Preferably, the adhesive layer is covered by a peel foil during shelf life of the device, and which preferably forms part of the sterile enclosure. The adhesive layer at least partially encloses or surrounds the bottom surface of the medical device. The peel foil of the medical device preferably comprises a main peel foil and a sticker, the sticker connecting to another sterile foil covering the passage to the ambient of fluid path housing.

A method for manufacturing and assembly of a medical device comprising the steps of:

Providing a fluid path comprising a spike for insertion through the septum of the reservoir, a cannula holder for holding a cannula or needle for insertion into the patient and a tubing for a fluid connection between the spike and the cannula holder, the fluid path being enclosed in a sterile enclosure during shelf life of the medical device and whereby the fluid path is enclosed in a fluid path housing with a bottom surface that is attachable to the skin of a patient Providing a drive mechanism which is connectable to a needle insertion and retraction mechanism present in the fluid path housing and which initiates the insertion of the needle into the patient—Providing a cartridge with medication that can be inserted into the fluid path housing Providing a top cover for the medical device that matches the fluid path housing Assembling the fluid path housing comprising the fluid path, the drive mechanism, the cartridge and top cover to form the medical device.

BRIEF DESCRIPTION OF THE DRAWINGS

Legends to the Figures
FIG. 1: Patch device, lateral view,
FIG. 2: Patch device, top view,
FIG. 3: Parts of subassembly for drive mechanism and control unit,
FIG. 4: Parts of subassembly for cover,
FIG. 6: Parts of subassembly of bottom part housing,
FIG. 7: Adhesive layer and capacitive sensor,
FIG. 9: Top view of assembled device without top cover, after medication delivery,
FIG. 13: Coupling mechanism according to a third embodiment, the second part is indirectly coupled to the housing via a third part, the first part at least partially surrounds the second part,
FIG. 26: Detail of needle insertion mechanism, needle retraction arm of the needle control element guides the cannula holder back to the needle retracted position,
FIG. 27: Detail of needle insertion mechanism showing the guidance of the cannula holder through the second guiding means of the spike inserter carrier,
FIG. 28: Detail of needle insertion mechanism, cams of third part interacting with the guiding contour of the needle control element after rotation over the second angle for needle retraction, FIG. 29 a: Detail of the interaction between the two cams of the third part interacting with the guide contour of the needle control element as the third part is rotated to rotate the needle control element over the first angle for needle insertion and over the second angle for needle retraction: Start position,
FIG. 29b: Needle control element rotated to release the cannula holder,
FIG. 29c: Cannula holder moved to the needle inserted position,
FIG. 40d: Detail of the needle insertion mechanism according to the third embodiment, needle inserted position,
FIG. 41: Drive mechanism of the injection device with a segmented piston rod according to a first embodiment, before expelling medication,
FIG. 41a: Drive mechanism of the injection device with a segmented piston rod according to a first embodiment, before expelling medication, details of the guidance for the piston rod,
FIG. 42: Drive mechanism of the injection device with a segmented piston rod according to the first embodiment, piston rod has advanced, reservoir is empty,
FIG. 47: Assembly of the cartridge in the cartridge holder connector at the cartridge holder and sterile barrier at the front of the cartridge,
FIG. 49: Assembly of the cartridge to the needle insertion sub-unit. The cartridge fixator is tubular shaped and has a sterile barrier foil at one end,
FIG. 49a: Assembly of an empty cartridge to the needle insertion sub-unit.

DETAILED DESCRIPTION

Figure 5:
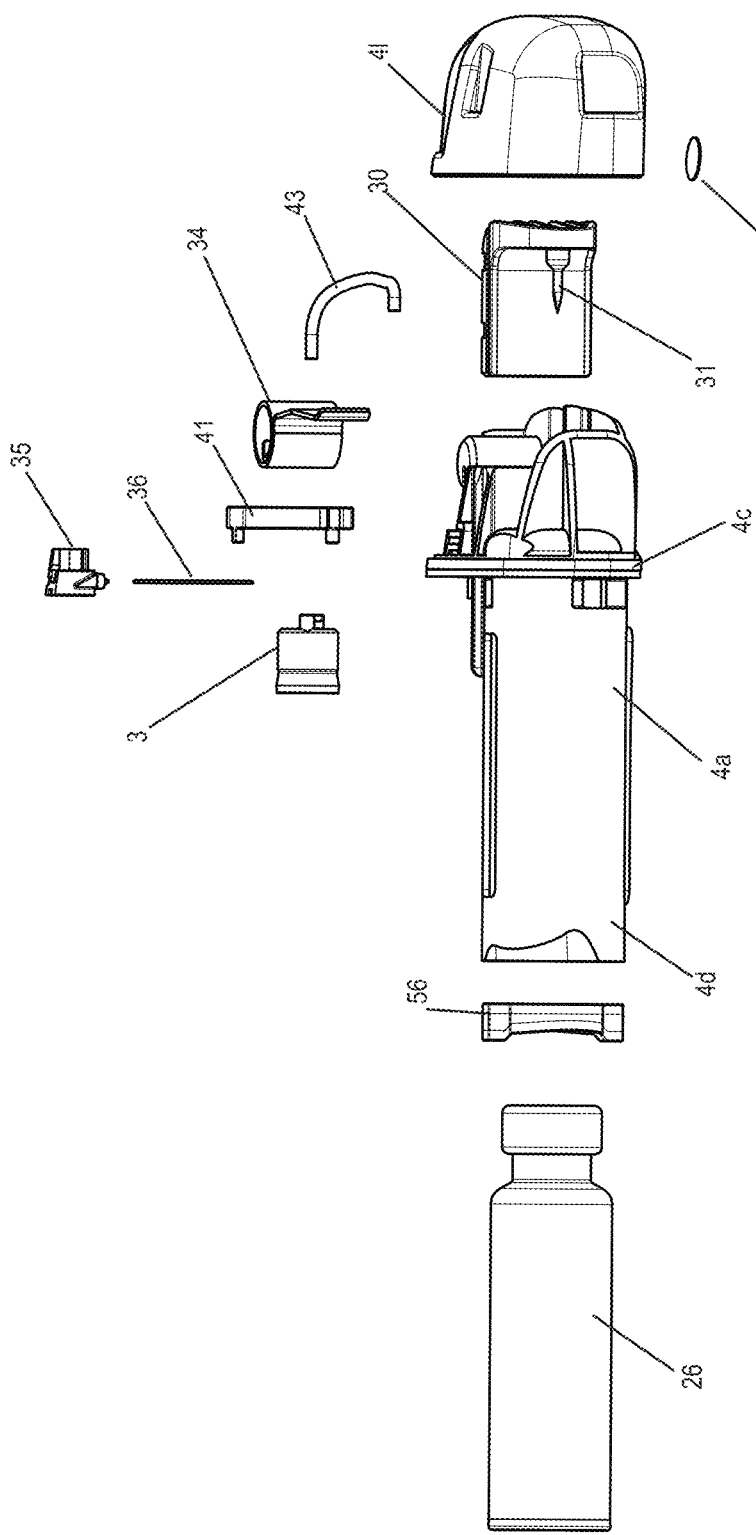
FIG. 5: Parts of subassembly for fluid path unit.

A lateral view and a top view of a patch device comprising the coupling mechanism, the segmented piston rod and fluid path sub-assembly is presented in FIGS. 1 and 2, respectively. The housing (4) comprises a housing cover (4j) with a window (4m) for viewing a cartridge and, preferably, a bottom housing part (4g). The housing furthermore preferably comprises a button (4k) for starting the injection or starting the device and/or an optical indicator (100), preferably a LED light. The subassemblies of the device are presented in FIGS. 3 to 6 showing the separate parts in an exploded view.

FIG. 3 shows the drive and control unit comprising a drive carrier (4h) which holds and guides a segmented piston rod (80). The drive carrier (4h) is closed by a drive cover (4n) and the carrier and cover hold the electromotor (83), a threaded rod (15) and a gearing arrangement including a worm wheel for driving the threaded rod (15). The gearing arrangement comprises an encoder (86) which counts the number of revolutions of the motor and/or threaded rod (15). The gearing arrangement is also connected to a first part (1) which forms together with a second part (2) a coupling mechanism that will be described below. A battery (102) and a control unit (101) are part of the subassembly as well.

In FIG. 4, the cover unit for the patch device is shown comprising a housing cover (4j) and, preferably, a button (4k), the button can also be located on one of the lateral planes of the housing (4). The fluid path unit in FIG. 5 presents a housing (4a) with a cartridge holder (4d) and a vertical wall (4c) which separates the cartridge holder from the needle insertion mechanism, the wall (4c) and a cover (4I) for the insertion mechanism are part of a sterile barrier. The needle insertion mechanism comprises a cannula holder (35) for holding a cannula (36), a spring means (34), a spike inserter carrier (30), a needle control element (41) and a third part. The functioning of the several parts will be described below.

FIG. 6 shows the subassembly of the bottom section of the device with a bottom housing part (4g), a capacitive sensor (103) an adhesive layer (104) which can be covered by an additional sticker for connecting the sterile barriers of the fluid path unit. In some embodiments, there is no separate bottom housing part, but is integrated with the housing (4a) of the fluid path sub-assembly. A detail of the capacitive sensor (103) is presented in FIG. 7, with conductive elements that are embedded or printed onto, or attached to an adhesive layer (104). The sensor and/or adhesive layer have a passage (106) required for insertion of the cannula. The peel-off foil (105) for the adhesive layer (104) prevents unintended adhesion or contamination of the adhesive layer. The peel-off foil (105) has a lid which extends beyond the contour of the adhesive layer which the user can grip. Removing the peel-off from the adhesive layer releases the adhesive layer but the removal can also be combined with other functionalities such as switching or activating the electrical circuitry or removing a sterile barrier of the fluid path sub-unit or opening a passage for the cannula. For example, the peel-off comprises as separate lid that isolates the battery contact, removing the peel-off directly closes the electrical circuitry. In another example, the peel-off comprises a pin that is attached to the peel-off foil and the pin penetrates though a passage the bottom housing part. Removing the peel-off activates a micro-switch that is part of the electrical circuitry.

Figure 8:
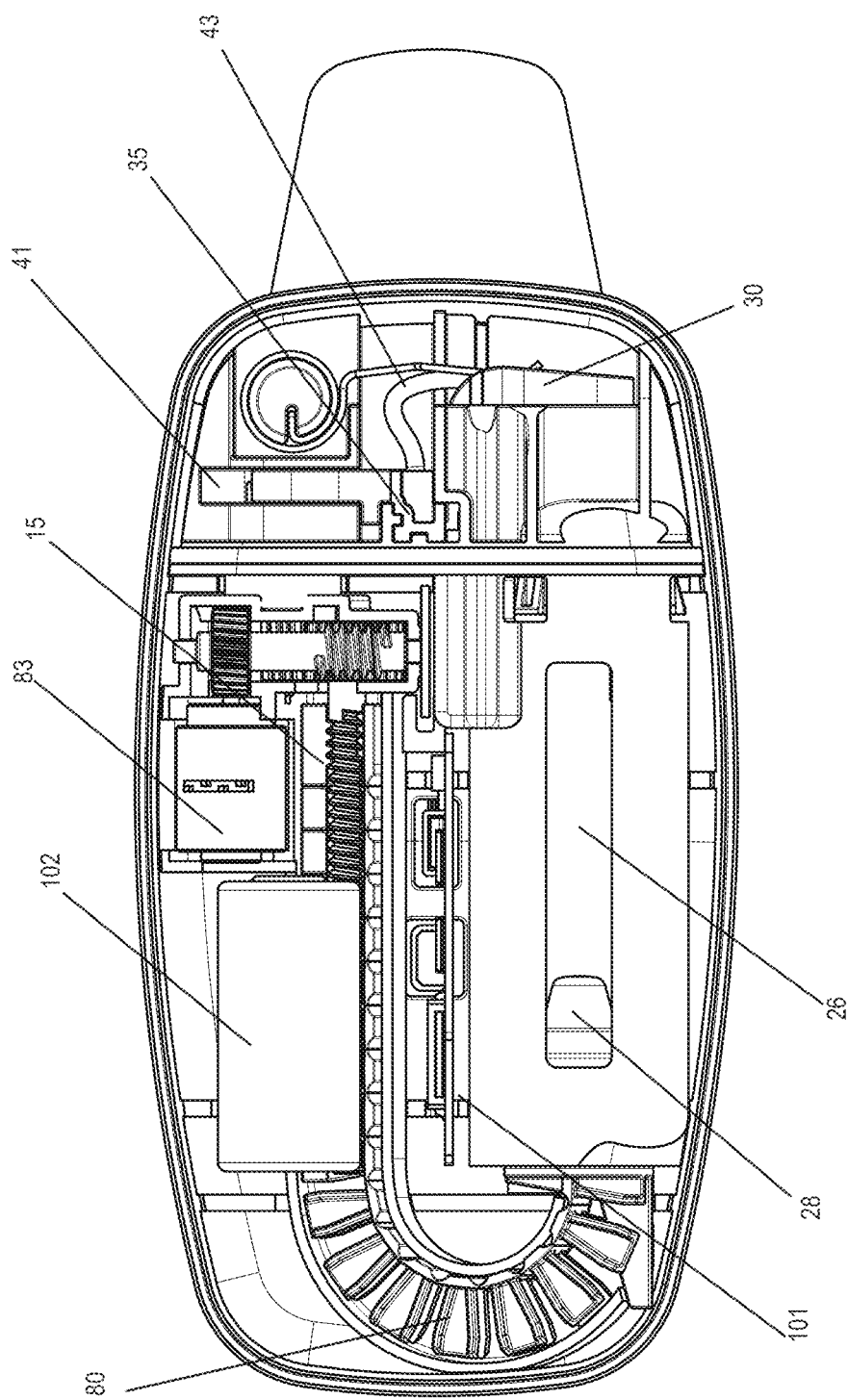
FIG. 8: Top view of assembled device without top cover, before medication delivery.

A top view of the assembled device without the housing cover (4j) is shown in FIG. 8 for a device with a reservoir that is full and the piston rod being in the starting position prior to delivery. Once the medication has been expelled, the piston rod has been advanced by the drive mechanism as shown in FIG. 9.

Figure 10:
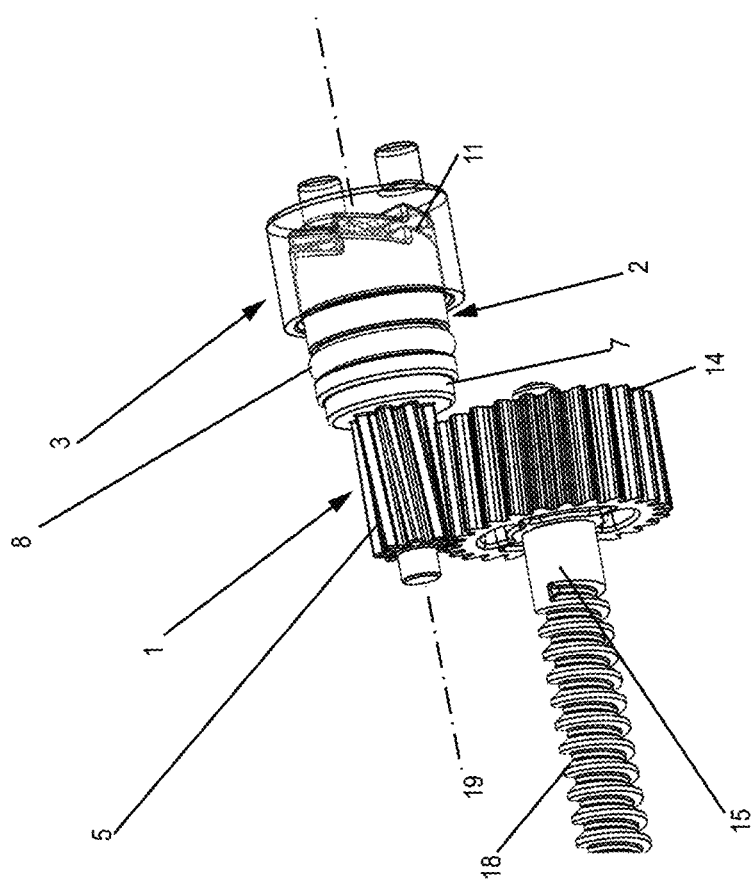
FIG. 10: Coupling mechanism according to a first embodiment of the device whereby the second part directly engages the housing.

In FIG. 10, a first embodiment of the coupling mechanism is presented with a first part or ratchet shaft (1) having a toothing (5) and at least one external thread or gearing (6). A circumferential flange (7) is located between the toothing (5) and threading (6). Adjacent to the toothing (5) the first part (1) has a bearing member (17) which ensures that the first part (1) can rotate, preferably with respect to a housing (4), around its longitudinal axis (19). The toothing (5) of the first part (1) matches a toothing (16) of a gear wheel (14). Preferably, the matching toothings are slightly oblique with respect to the longitudinal axis and form a helical gearing to ensure a smooth drive mechanism and/or ensure that an axial force along the rotation axis is exerted onto the first part to enable an axial shift of the first part, or to secure its position in a bearing or to use the axial shift for coupling, or decoupling to the second part. The gear wheel (14) is directly coupled, e.g. axially and rotationally fixed coupled to a threaded rod (15) having an external threading (18). The threaded rod drives the piston rod which ensures that medication is expelled from the reservoir. The threaded coupling between the gear wheel (14) and the first part (1) is permanent, thus a rotation of the gear wheel will always result in a rotation of the first part (1), but also in a rotation of the threaded rod (15).

A second part, or coupling member (2) concentrically surrounds the threading or gearing (6) of the first part (1). The second part (2) has at least one thread segment or protrusion (10) which engages the threading (6) of the first part (1). The thread segment or protrusion (10) is located on the inside of the second part and points towards the longitudinal axis (19). In the first embodiment, the second part (2) is surrounded by an O-Ring or friction element (8) which preferably provides an axial and/or radial friction force or torque between the second element (2) and the housing (4) or a part attached to the housing. The O-ring is axially secured with respect to the second part in a circumferential notch (9). The dimensional tolerances and/or materials are designed such that the friction between the gearing or threading (6) of the first part (1) which is in engagement with a pin or thread segment (10) of the second part, has a first frictional resistance below the f fictional resistance, or second frictional resistance generated by the O-ring or friction element (8) and the housing (4).

A rotation of the gear wheel (14), preferably by a drive mechanism comprising the motor and a worm wheel, results in a rotation of the first part. Due to the threaded engagement between the first (1) and second (2) part in combination with the higher friction on the outside of the second part, which axially and rotationally temporarily holds or fixates the second part (2) with respect to the housing, this ensures that the second part (2) axially shifts away from the flange (7) of the first part (1) without rotation or at least rotates less, e.g. at a lower angular velocity than the first part. Reversing the rotation direction, for example by reversing the rotation direction of the electromotor, results in a rotation of the first part (1) in the opposite direction. The opposite rotation direction together with the fact that the frictional resistance on the outside of the second part is above the resistance on the inside, e.g., the second part is held on the outside yet still allowing for axial and/or rotational movements, results in a movement of the second part (2) towards the flange (7). The axial movement of the second part (2) with respect to the first part (1) is restricted by the threaded engagement or axial abutment between the two parts. For example, once the thread segment (10) of the second part reaches an end of the threading (6) on the first part, a radial abutment between the end surfaces of the at least one thread segment (10) and the threading (6) forces the second part (2) to co-rotate with the first part (1) at the same angular velocity, thus surpassing the external friction on the outside of the second part (2). Alternatively, there is an axial abutment of the second part (2) with the flange (7) of the first part (1).

Figure 11:
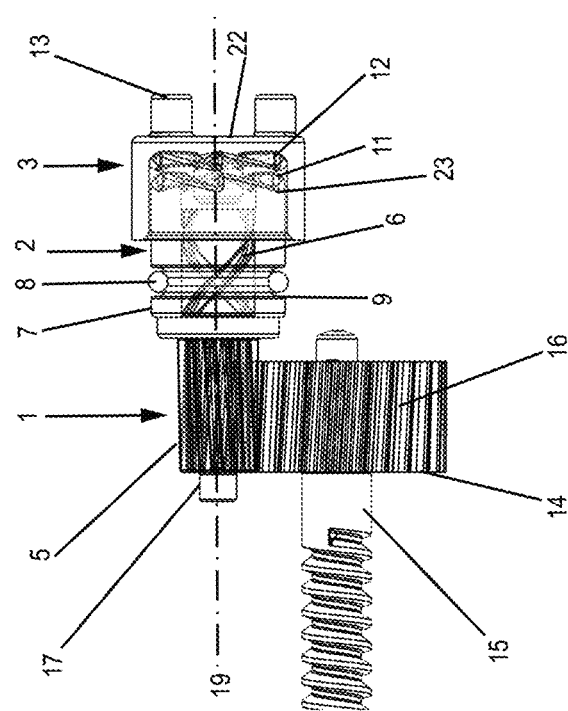
FIG. 11: Coupling mechanism according to a first embodiment.

The second part is concentrically surrounded by a third part (3) and the first, second and third part preferably rotate around the same longitudinal axis (19). The second part (2) is in the present embodiment positioned between the first part (1) and the third part (3). The third part has an end surface (22) with at least one cam or protrusion (13) pointing outwards and a toothing (12), preferably an asymmetric toothing, pointing towards the second part (FIG. 11).

The second part has an end surface (23) with an toothing (11), preferably an asymmetric toothing circumferentially arranged that matches or complements the toothing (12), preferably an asymmetric toothing present on the end surface (22) of the third part (3). Once the toothings of the second and third part (11, 12) are in a form fit after closing the coupling by the axial shift of the second part (2) towards the third part (3), the first part, the second part and the third part co-rotate in one rotation direction at the same angular velocity. Reversing the rotation direction opens, or decouples the coupling (11,12) between the second part and the third part, e.g., the toothings (11,12) move out of engagement, the third part (3) will stop co-rotating with the first (1) and second (2) part. The first rotation direction for closing the coupling is preferably accompanied with a needle insertion and/or needle retraction, the second rotation direction which is opposite to the first rotation direction is linked to or causes delivery of medication.

The coupling of the second part (2) to the third part (3) in a rotationally locked configuration ensures that the cams (13) which are on the end surface (22) of the third part, also rotate a needle control element (41) over a defined angle. Preferably, the angle is defined by the number of revolutions of the electromotor, which via a worm wheel gearing results in rotation in a first rotation direction of the third part (3) and via the cams (13) to a rotation of the needle control element (41). The needle control element has a guiding element or a guiding contour which can interact with the at least one cam (13) of the third part such that a controlled rotation and/or translation occurs once the third part (3) has been rotated over a first angle. Further rotation/and or translation of the needle control element (41) over a further angle being greater than the first angle will activate a needle retraction mechanism.

Figure 12:
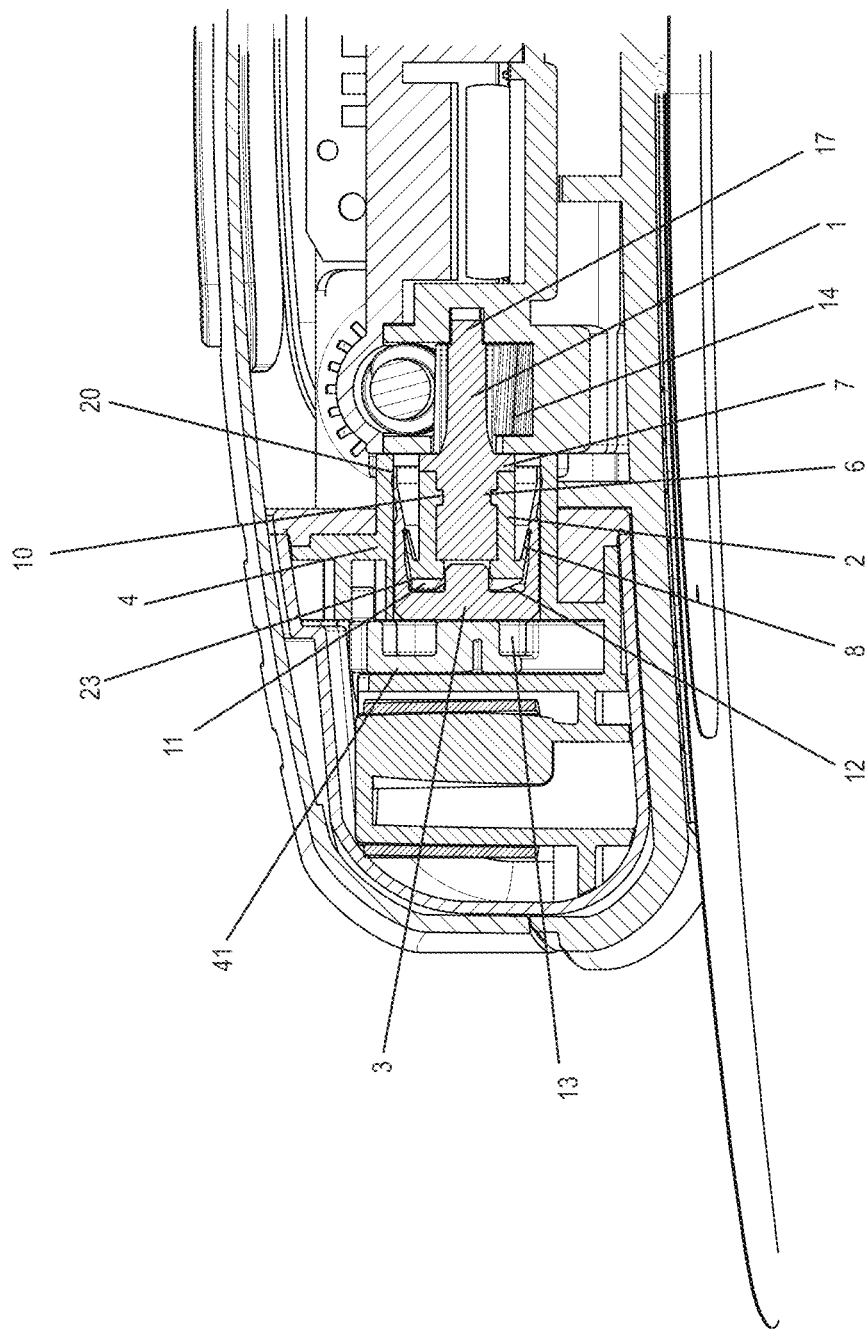
FIG. 12: Coupling mechanism according to a second embodiment, the second part is indirectly coupled to the housing via a third part; the second part surrounds the first part.

A second embodiment of the coupling mechanism is shown in FIG. 12. The coupling mechanism functions comparable to the first embodiment, however the second part (2) is directly coupled to the third part (3) via at least one friction element (8), preferably shaped as at least one elastic wing or wing segment that is biased against the inner wall of the third part (3) which runs parallel to the longitudinal axis (19). The third element (20) is press fitted into the housing (4) resulting in a second friction fit engagement. The rotation of the first part and the accompanying axial shifts and coupling-decoupling sequences of the second and third part are described above.

A third embodiment of the coupling mechanism is presented in FIG. 13. The third part (3) concentrically surrounds the first (1) and second part (2). However, the first part surrounds at least partially the second part (2) and the threading or gearing which is present on the outside of the first part (1) in the first embodiment has shifted to the inside surface. In all embodiments the location of the gearing or threading and the engaging thread segment or pin can also be reversed, e.g. the threading or gearing can also be located on the second part and the engaging pin or thread segment is available on the first part.

Figures 14, 15:
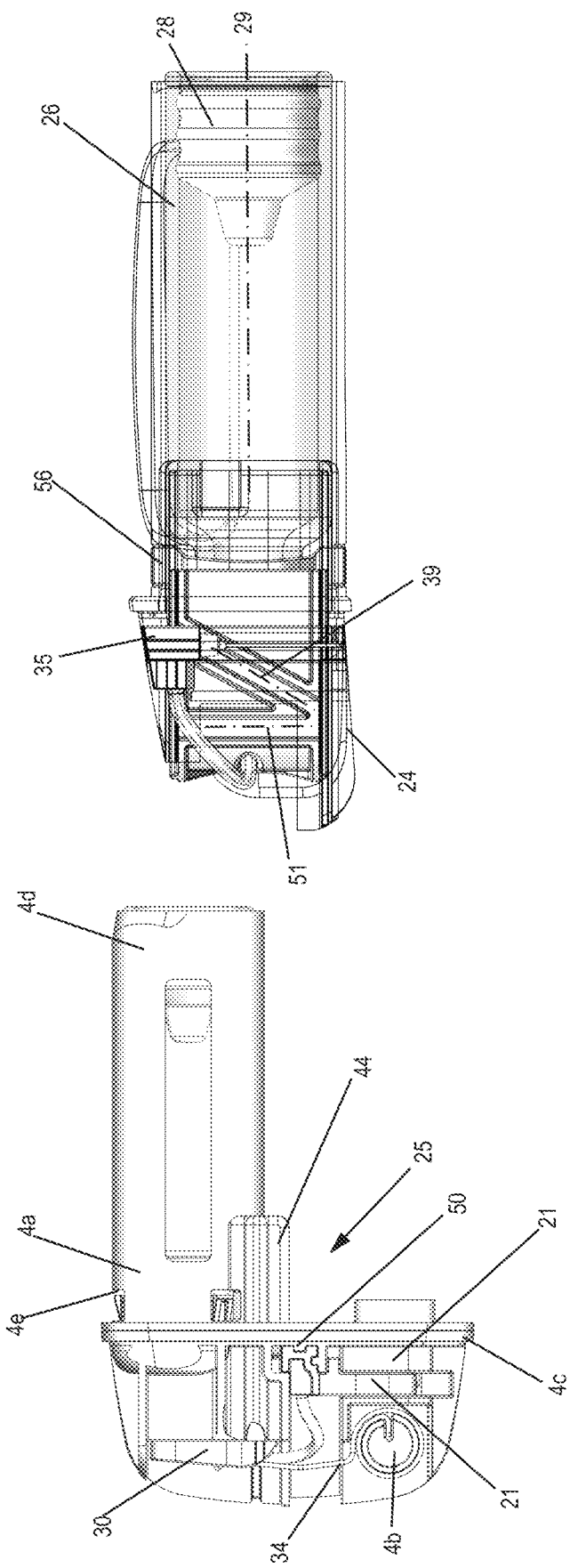
FIG. 14: Fluid path unit, top view.
FIG. 15: Fluid path unit, lateral view showing the first and second guiding means.

In FIG. 14 a fluid path assembly (25) is presented showing the housing (4a) having the cartridge holder (4d), preferably shaped as a cylinder having an open end for receiving the cartridge or reservoir (26). The cartridge holder has a viewing window that can be aligned with the viewing window of the housing. The cartridge holder (4d) is separated from the needle insertion and retraction compartment by a vertical wall (4c) which is optionally surrounded by an elastomeric material to provide a fluid tight and/or sterile barrier between the parts on one side of the vertical wall (4c) and the inside of the insertion mechanism, once the insertion mechanism is encapsulated by a cap or needle housing cover (4I). The housing (4a) comprises a spring holder (4b) for holding a spring, preferably a leaf spring. The housing (4a) has a guide slot (44) for guiding a spike inserter carrier (30), the spike inserter carrier being biased by the end (34a) of the leaf spring (34).

FIG. 15, presents a lateral view of the fluid path assembly showing the cartridge or reservoir (26) having a longitudinal axis (29) that is oriented parallel to the bottom surface (24) of the fluid path assembly (25) or the injection device. The reservoir (26) has a plunger (28) on one end and a septum (27) on the opposite end which is crimped onto the reservoir. The reservoir or cartridge is fixated around the tapered neck of the cartridge using a cartridge fixator (56) which is a flexible or semi-flexible element for holding the neck of the cartridge, for example directly onto the shoulder of the cartridge. Alternatively, the cartridge fixator engages the metal crimp of the cartridge. In another alternative, the cartridge is glued or welded to the cartridge holder. In yet another alternative, the edge of the opening of the cartridge which is opposite to the septum, is in a snap-fit connection to the housing.

The cartridge fixator (56) is connected to the housing (4a) by a snap-fit connection using holes (4e) in the cartridge holder (4d) and at least one matching protrusion on the cartridge fixator (56). Preferably, the cartridge (26) is inserted in the cartridge holder opening with the septum (27) pointing towards the needle insertion unit, as presented in FIG. 15. Alternatively, the insertion is reversed and the plunger (28) points towards the insertion unit. Furthermore a cannula holder (35) is shown in a needle retracted position (37) whereby the cannula holder is furthest away from the bottom surface (24). In side view, the first guiding means (39) and the second guiding means (51) are indicated, which both are shaped as linear guiding slots on a lateral wall surface of the spike inserter carrier (30).

Figure 16:
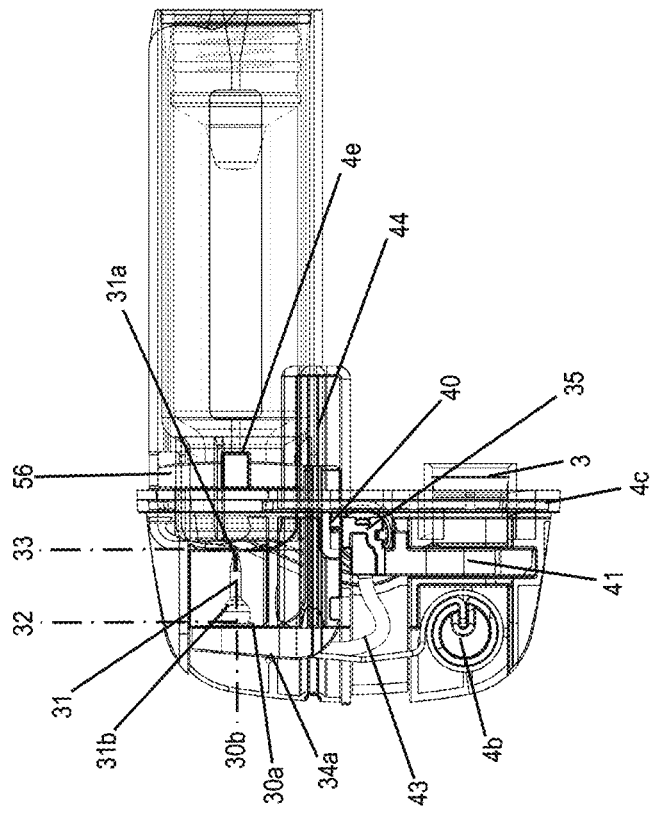
FIG. 16: Fluid path unit, top view showing the spike inserter carrier in the non-inserted position.

A top view (FIG. 16) of the fluid path unit (25) presents the spike inserter carrier (30) as an V shaped part with one leg being guided in the guide slot (44) of the housing and the other leg carrying a spike (31). The spike being attached to a base surface (30a) of the spike inserter carrier (30) and in the current example, the spike (31) and spike inserter carrier (30) are injection molded as one unit. The spike (31) has a longitudinal axis (30b) which is aligned with the septum (27) or longitudinal axis (29) of the cartridge (26). The spike inserter carrier can shift from a first position (32) to a second position (33) and is guided through the guide slot (44) of the housing, the second position is where the tip (31a) of the spike penetrates the septum (not shown here). The movement from the first (32) to the second position (33) is biased by the spring (34) and a release of the spring energy moves the spike inserter parallel to the bottom surface (24). The tip of the spring (34a) abuts the base surface (30a) of the spike inserter carrier for transferring the spring energy. As a result, the spike penetrates the septum of the reservoir, preferably the longitudinal axes of the spike and the reservoir are aligned with each other for a central puncture of the septum. A tubing (43) connects the spike (31) to the cannula holder (35) to create a fluid path between a cannula (36) and the contents of the reservoir (26) once the spike (31) has been inserted.

Figure 17:
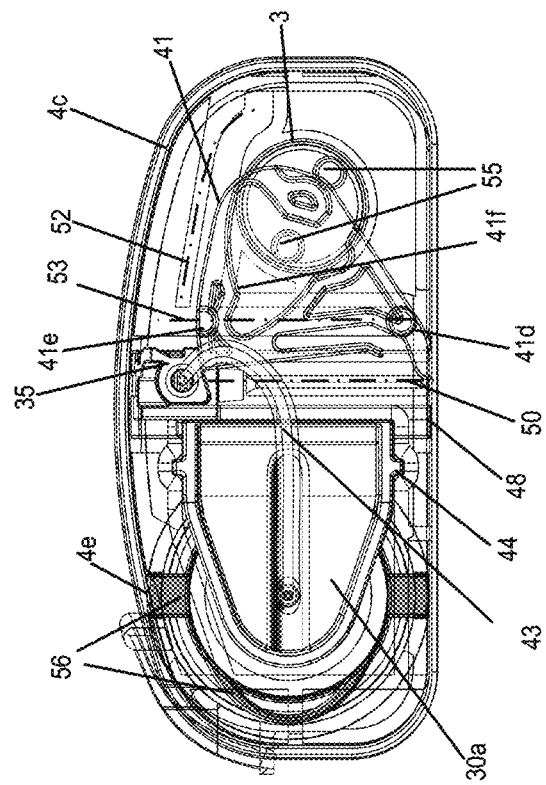
FIG. 17: Fluid path unit, lateral view showing the tubing, cannula holder and the third and fourth guiding means on the housing for guiding the needle control element.

Another lateral view (FIG. 17) of the fluid path unit (25) shows an example of the cartridge fixation (56) being formed as an ellipsoidal shaped ring, preferably made from an elastic material, which is connected to the openings (56) of the cartridge holder housing (4d) via connectors that are attached to the ellipse part parallel to the long axis of the ellipse. The ellipse elements parallel to the long axis fit around the neck of the cartridge (26) and fit behind a metal crimp holding the septum. The cartridge fixation ensures that the cartridge (26) remains axially and radially fixated in the cartridge holder. Also the axial forces which are acting upon the cartridge due to the penetration of the septum by the spike are counteracted by the cartridge fixation ring (56). Other alternatives include a crimp designed to fit into the cartridge holder (4d) and which can have a locking element, preferably a flexural element or snappers that directly fit into matching counter-elements to fixate the cartridge in the cartridge holder. Such a crimp can be made from a metal having, for example, flexural or spike elements pointing outwards that plastically deform the inside wall of the cartridge holder and/or the element itself during axial and/or rotational movement during cartridge insertion. Alternatively, the crimp is made from a plastic material with snappers that fit into holes present in the wall of the cartridge holder (4d). Or the plastic or metal crimp has an outside threading matching a threading on the inside of the cartridge holder such that the cartridge can be screwed into the holder.

The lateral view shows the tubing (43) connecting the end of the spike with the cannula holder (35), the tubing is partially keyed to the base surface (30a) of the spike inserter carrier. The lateral view shows guiding means which are part of the vertical wall (4c) which provide a motion-link for several parts that are engaged with the side wall (4c). The guiding means are highlighted in FIG. 17 with dot-dash lines and are shaped as at least one groove, edge or rim that is formed during the manufacturing process of the fluid path housing assembly (25), preferably during injection molding. A linear guide (50) is engaged with the cannula holder to linearly guide the cannula holder from the needle retracted to the needle inserted position. Preferably, the linear guide (50) is part of the housing. The linear guide may be oriented perpendicular to the bottom surface or is inclined to the bottom surface, thus enabling also a non-perpendicular insertion of the cannula into the patient's skin. The wall section (4c) of the housing comprises further a third guiding means (52) and fourth guiding means (53) which are shaped as at least one groove, rim or edge to guide the needle control element (41). The needle control element has at least two keys (41d, 41e) which each engage the third and fourth guiding means of the housing (52, 53), respectively. The needle control element (41) is driven by the third part (3) having at least one cam, in this example two cams (55). Depending on the interaction of the cams (55) with a guiding contour or motion-link on the needle control element, the needle control element (41) rotates and/or translates due to the engagement between the keys of the needle control element and the third and fourth guiding means (52, 53) of the wall of the housing (4c).

Figure 18:
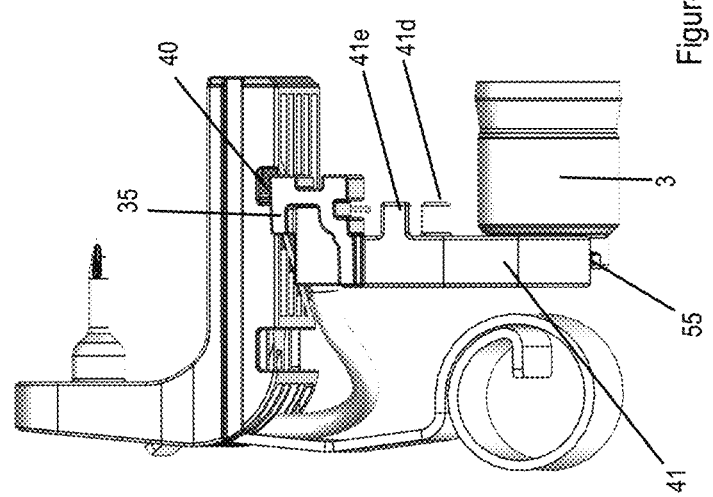
FIG. 18: Detail of the needle insertion mechanism, needle retracted position.

FIG. 18 shows a detail of the needle insertion mechanism in the needle retracted state prior to insertion of the spike into the reservoir. The third part (3) is shown with the two cams (55) whereby one cam interacts with the guiding contour of the needle control element (41). The two keys (41d, 41e) of the needle control element are visualized in FIG. 18 without the matching third and fourth guiding means of the wall surface (4c).

Figure 19:
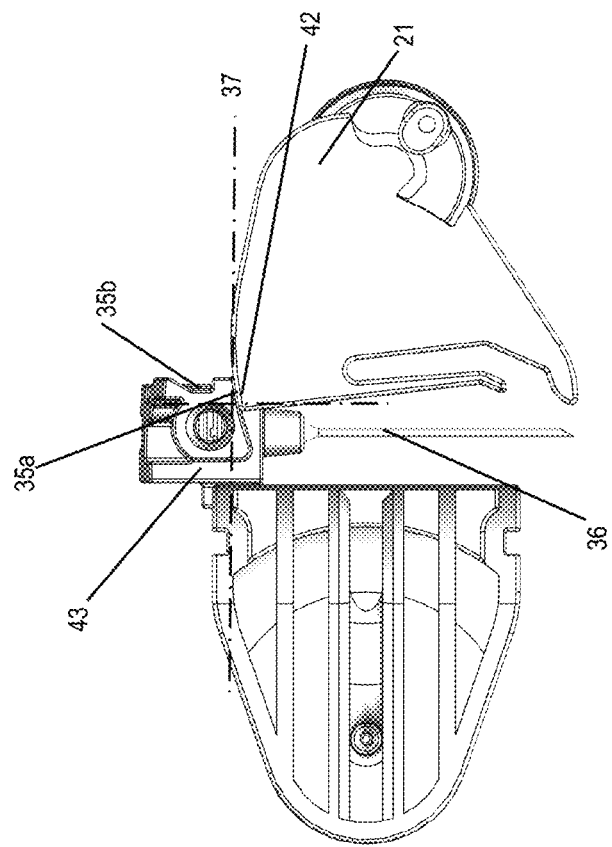
FIG. 19: Detail of the needle insertion mechanism, needle control element prevents movement of the cannula holder and the spike inserter carrier.
Figure 21:
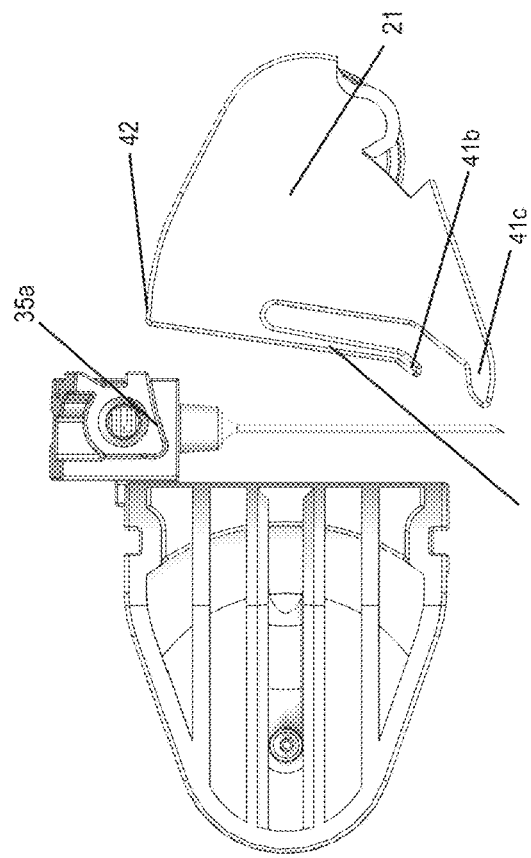
FIG. 21: Detail of the needle insertion mechanism, needle control element rotated over the first angle to release the cannula holder and spike inserter carrier.
Figure 20:
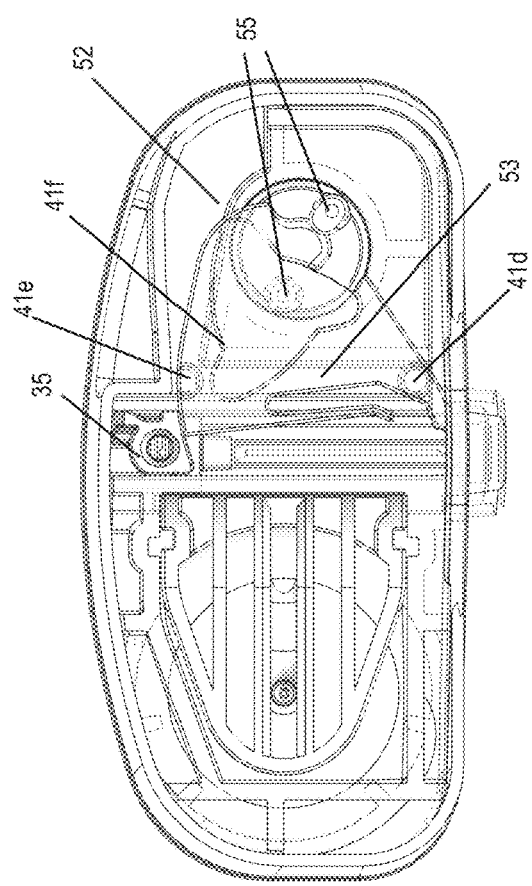
FIG. 20: Detail of the needle insertion mechanism, needle control element prevents movement of the cannula holder and the spike inserter carrier, guide contour and cams of the third part are shown.
Figure 22:
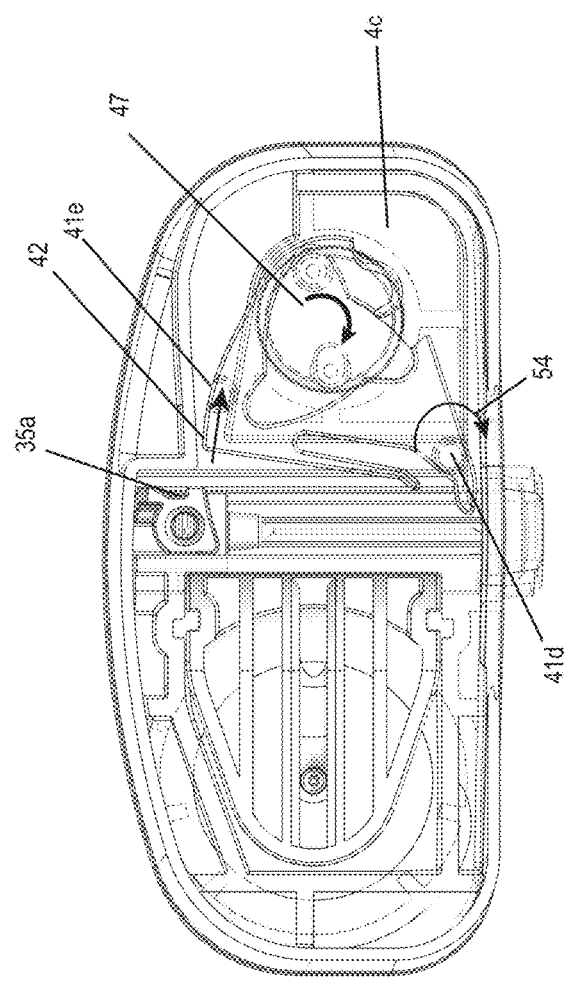
FIG. 22: Detail of the needle insertion mechanism, showing the pivoting of the first key in the third guiding means and the axial movement of the second key in the fourth guiding means.

In FIG. 19, the arrester (42) abuts an abutment surface (35a) of the cannula holder (35) such that the cannula holder (35) remains in the needle retracted position (37). The same position of the elements is presented in FIG. 20, but the position of the guiding contour (41f) and the position of the two cams (55) of the third part are visualized in a see-through view. The functioning of the needle insertion mechanism and the coupling of the drive mechanism to the needle control element is described as follows. The third part (3) is coupled to the first part (1) which is rotated in the first rotation direction and the coupling ensures that the two cams (55) of the third part rotate in the first rotation direction such that the needle control element (41) is rotated around the first key (41d) of the needle control element and rotates in the fourth guiding means (53) without axial movement. The second key (41e) of the needle control element (41) axially translates in the lateral direction within the third guiding means (52) without rotation. As a result, the needle control element is rotated around the first key (41d) from the starting position over an angle, preferably the first angle which ensures that the abutment between the arrester (42) and the contact surface (35a) of the cannula holder is released (FIG. 21). Details of movement of the second key (41e) within the third guiding means (52) and the pivoting (54) of the needle control element (41) around the first key (41d) of the needle control element are shown in the see-through view of FIG. 22. In the shown example, the needle control element (41) is rotated over a first angle between 5° and 40°, preferably between 8° and 30°, more preferably between 10° and 20°, most preferably to an angle of 15°.

Figure 23:
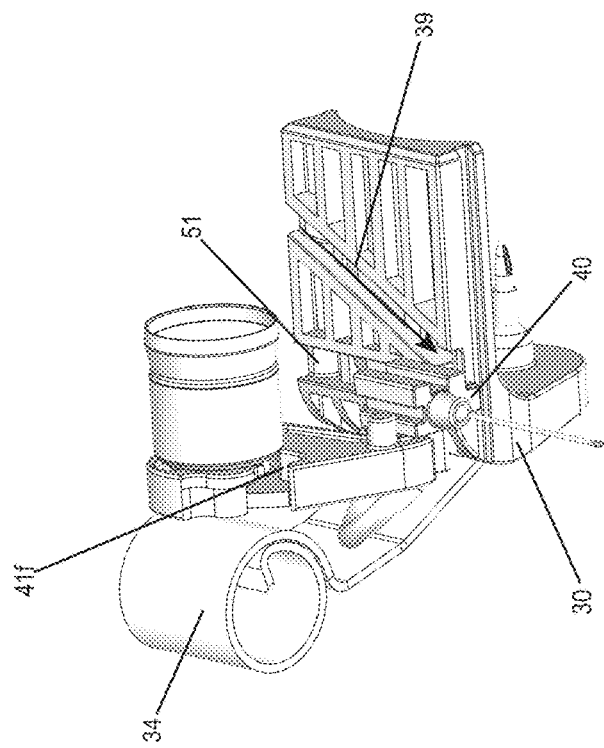
FIG. 23: Detail of needle insertion mechanism showing the position of the needle cannula holder after being driven by the first guiding means to the needle inserted position.
Figure 24:
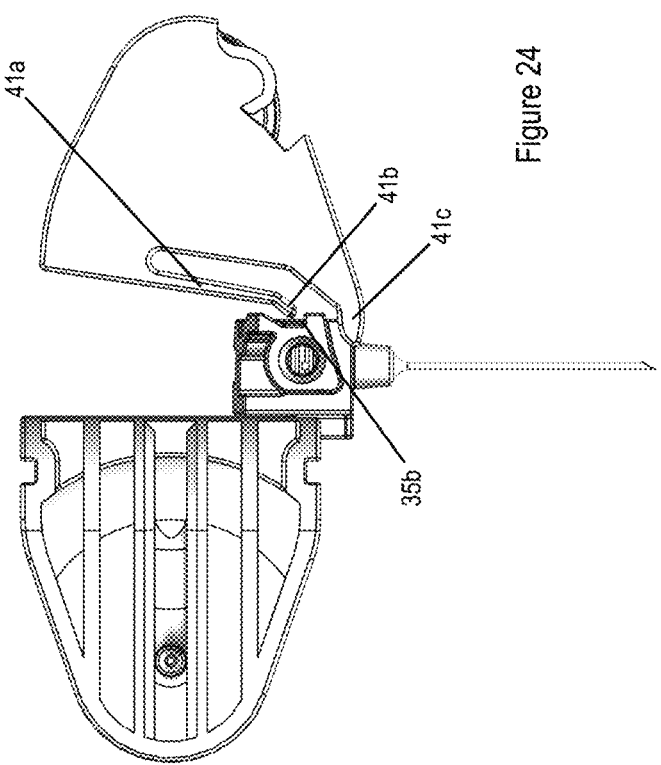
FIG. 24: Detail of needle insertion mechanism showing the cannula holder in the needle inserted position and the locking mechanism.

The release of the abutment between the needle cannula holder (35) and the needle control element (41) releases the spring forces of the spring (34) and advances the spike inserter carrier (30). The advancement of the carrier drives the cannula holder (35) via the transformation means (40) and the first engagement means (39) from the needle retracted position to the needle inserted position (38), as schematically presented in FIGS. 23 to 25. In this example, the transformation means (40) is shaped as a protrusion with a cross section having at least one face parallel to the angulated guiding means, for example a triangular shape. Other shapes of the cross section such as circular or elliptical can also be envisaged.

Figure 25:
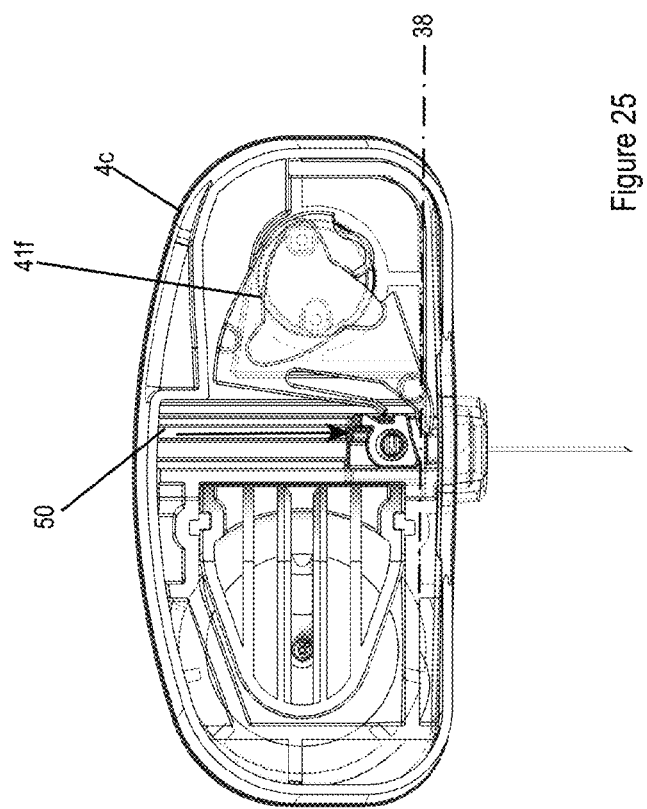
FIG. 25: Detail of the needle insertion mechanism showing the movement of the cannula holder through the guiding means of the housing.

As the cannula holder (35) moves into the needle inserted position (38), the locking arm (41*a*) of the needle control element flexes into the catch (35*b*) of the cannula holder (35) such that the end (41*b*) of the locking arm prevents a reversed motion of the cannula holder (35) towards the needle retracted position. In FIG. 25, a transparent view is shown including the wall (4*c*) of the housing and including the linear guide (50) which guides the cannula holder vertically as the cannula holder is driven to the needle inserted position.

Once the cannula holder (35) is in the inserted position, the rotation direction of the first part (1) is reversed to the second rotation direction, the coupling is opened and the needle control element (41) is not rotated. The rotation of the drive mechanism in the second rotation direction advances the piston rod for medication delivery. After medication delivery, the rotation direction of the drive mechanism and, therewith the first element (1), is reversed once again to the first rotation direction and the coupling between the second and third part (11, 12) is closed. The third part (3) is rotated and the cams (55) engage with the guiding contour (411) or motion-link of the needle control element (41), and the needle control element (41) is rotated further, starting the release of the insertion mechanism. The rotation of the third part (3) drives the needle control element such that the first key (41*d*) axially shifts upwards in the fourth guiding means (53) whereas the second key (41*e*) axially shifts sideways in the third guiding means (52). The resulting movement is a combined rotation and translation of the needle control element (41) which ensures that the needle retraction arm (41*c*) of the needle control element (41) abuts the abutment surface (35*a*) of the cannula holder (35) and pushes the cannula holder (35) back to the needle retracted position (37) (FIG. 26). The cannula holder is guided in the linear guide (50) of the housing but is also guided in the spike inserter carrier (30) through the second guiding means (51) as is shown in FIG. 27 and in a semi-transparent view in FIG. 28, where the movement of the keys (41*d*, 41*e*) in the guiding means (52, 53) of the housing is illustrated.

The needle control element (41) is fixated after this second rotation by latching or locking means present in the third or fourth guiding means of the housing which interact and lock one or both of the keys (41*d*, 41*e*) of the needle control element. For example, a flexural arm present in the third guiding means (52) flexes as the second key (41*e*) moves axially in the third guiding means and irreversibly locks the second key. In another alternative, a catch is present in the fourth guiding means and the first key (41*d*) moves into the catch as the first key moves upwards in the fourth guiding means (53).

The interaction between the two cams of the third part and the guiding contour of the needle control element which form together with the keys of the needle control element a motion-link system is described in more detail in FIGS. 29*a* to 29*g*.

Figure 29E:
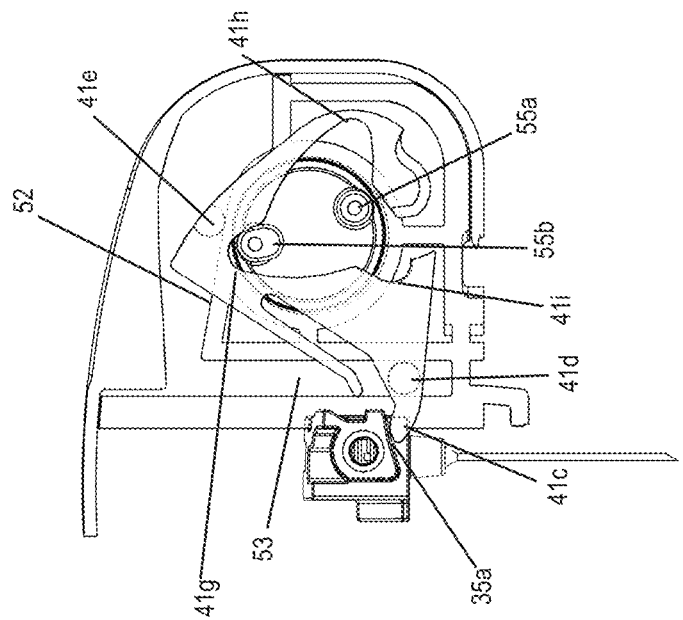
FIG. 29e: Needle control element rotates and translates to move the cannula holder towards the needle retracted position.
Figure 29D:
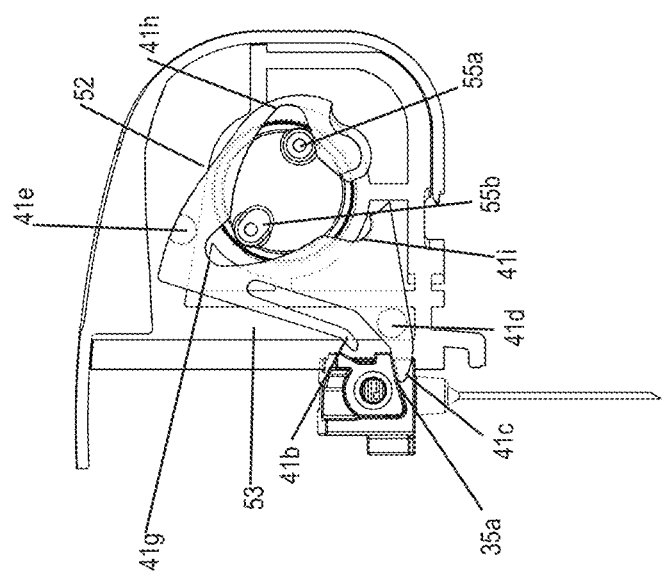
FIG. 29d: Needle control element rotated over further angle, needle retraction arm abuts the cannula holder.
Figure 29G:
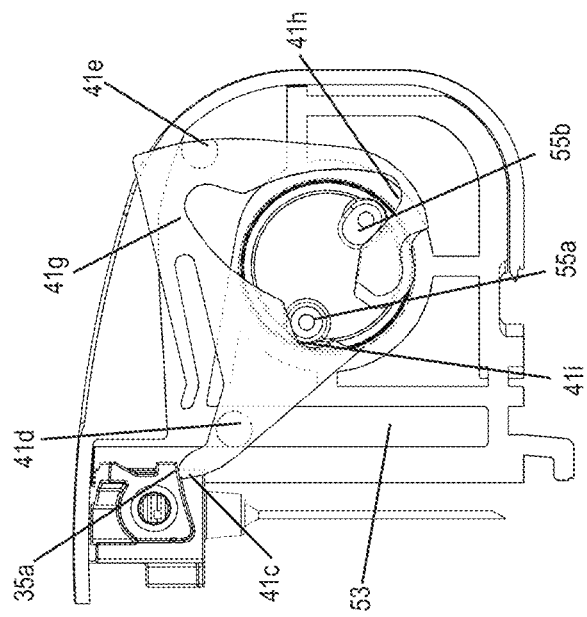
FIG. 29g: Cannula holder back in the needle retracted position.
Figure 29F:
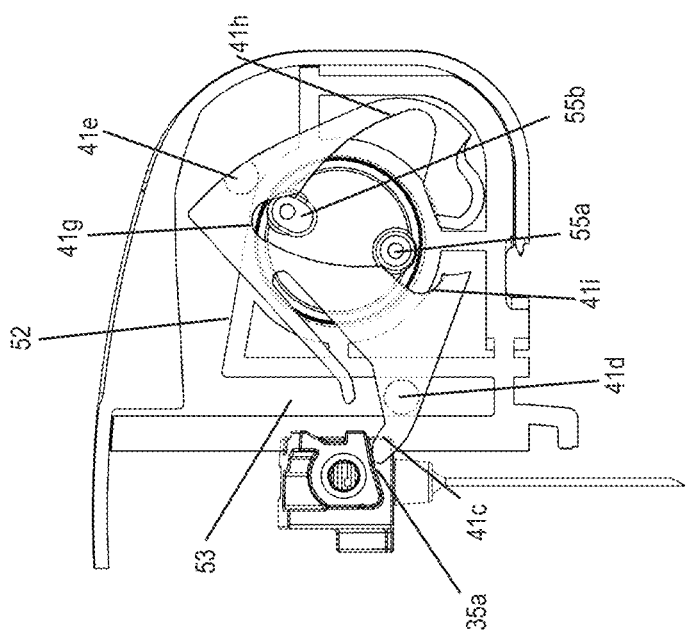
FIG. 29f: Cannula holder moves towards needle retracted position.

In this example the two cams (55) of the third part are not identical, cam (55*a*) is a circular protrusion whereas the cam (55*b*) is rounded but more elongated. The two cams protrude from the third part and each can a have a different length for interacting with different parts of the guiding contour (41*f*) of the needle control element (41). The guiding contour is shaped as a recess in the needle control element and comprises three pockets (41*g*, 41*h* and 41*i*) that can interact with the two cams of the third part as the third part is rotated. The three pockets are in this example positioned as a triangle with respect to each other but other configurations can be envisaged. The needle control element (41) is guided in the housing by the two keys (41*d*, 41*e*) of the needle control element that interact with the two guiding means (52, 53) of the housing, respectively. In FIG. 29*a*, which represents the starting position before the needle is inserted, the two cams (55*a* and 55*b*) do not interact with the guiding contour of the needle control element and the arrester (42) holds the cannula holder in the needle retracted position. For needle insertion, the third part is rotated over an angle such that first cam (55*a*) engages the second pocket (41*h*) of the needle control element which starts to rotate around the first key (41*d*), and the second key (41*e*) axially shifts in the third guiding means (52), see FIG. 29*b*. Once the needle control element has been rotated over an angle, the abutment between the arrester (42) and the cannula holder is released such that the needle can move from the needle retracted to the needle inserted position (FIG. 29*c*). The rotation direction of the drive mechanism is now reversed to open the coupling such that the third part does not rotated while the threaded rod is rotated to expel medication from the device. After emptying the reservoir, the rotation direction is reversed and the third part is coupled such that it can rotate over a further angle. The further rotation of the third part ensures that the first cam (55*a*) of the third part (3) moves in the second pocket (41*h*) such that the needle control element is rotated over a further angle and pivots around the first key (41*d*), FIG. 29*d*. The needle retraction arm (41*c*) abuts the abutment surface (35*a*) of the cannula holder (35) and axially starts moving the cannula holder towards the needle retracted position. Further rotation of the third part (3) releases the first cam (55*a*) of the third part from the second pocket (41*h*) of the needle control element whereas the second cam (55*b*) contacts the first pocket (41*g*), FIG. 29*e*. The needle control element rotates and translates as both the first key and second key (41*d*, 41*e*) of the needle control element axially shift in the corresponding fourth and third guiding means (53, 52). Further rotation of the third part (FIG. 29*f*) ensures that the second cam (55*b*) remains in contact with the first pocket (41*g*) whereas the first cam (55*a*) abuts the third pocket (41*i*). Further rotation of the third part ensures that the second cam (55*b*) abuts the second pocket whereas the first cam (55*a*) contacts the third pocket (41*i*) such that the needle control element is rotated and translated so far as to bring the cannula holder back into the needle retracted position (FIG. 29*g*).

Figure 30:
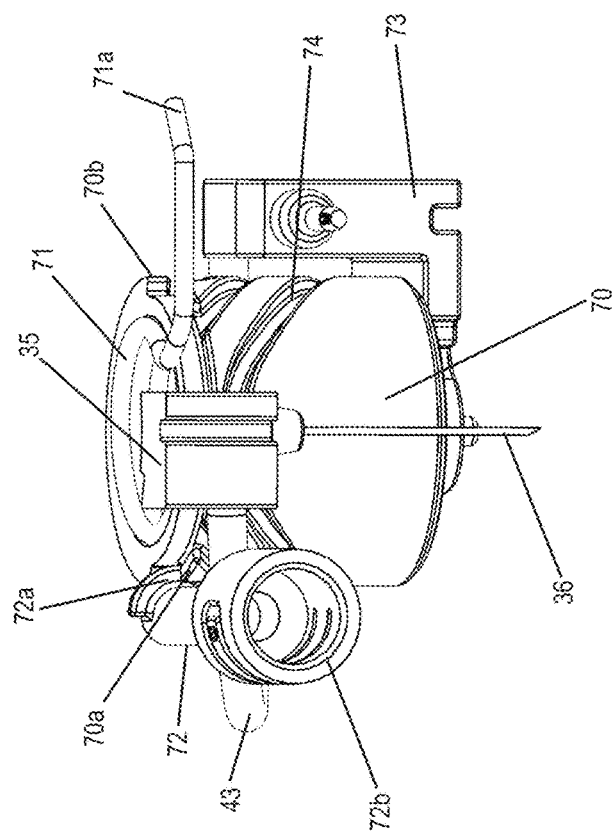
FIG. 30: Detail of the needle insertion mechanism according to a second embodiment, needle retracted position. Stop means in abutment with the first arrester.

In FIG. 30, a needle insertion mechanism according to a second embodiment is shown with the cannula holder (35) in the needle retracted position. A steering drum (70) is positioned with its longitudinal axis preferably perpendicular to the bottom surface of the device and can rotate with respect to the housing. The steering drum (70) has two arresters, a first steering drum arrester (70*a*) and a second steering drum arrester (70*b*) that are attached or attachable to the outside surface of the steering drum (70). A biasing means (71), preferably a spring means or a torsional spring is functionally positioned between the housing and the steering drum (70). Preferably, the spring is pre-stressed and the end of the spring (71*a*) preferably abuts the housing or housing part whereas the other end of the spring (not shown) is attached to the steering drum (70). The steering drum has a guiding means (74), preferably shaped as a recession on the outside surface, preferably with a sinusoidal shape which catches a transformation means or pin present on the cannula holder (35). The cannula holder (35) is linearly guided with respect to the housing and can be guided perpendicular to the bottom surface, or as an alternative, under an inclination angle such that the cannula (36) is inserted under an angle. The steering drum (70) is biased by the spring (71) to rotate in one rotation direction and rotation of the steering drum (70) is prevented by a stop means (72) with a counter arrester (72*a*) which abuts the first arrester (70*a*) of the steering drum (70). The stop means (72) has a longitudinal rotation axis (72*c*) and a coupling member (72*b*). The coupling member (72*b*) is preferably equipped with a ratcheting element or flexural element which can, for example, interact with the third part (3) of the coupling mechanism, such that the drive mechanism can be coupled to the stop means (72).

Figure 31:
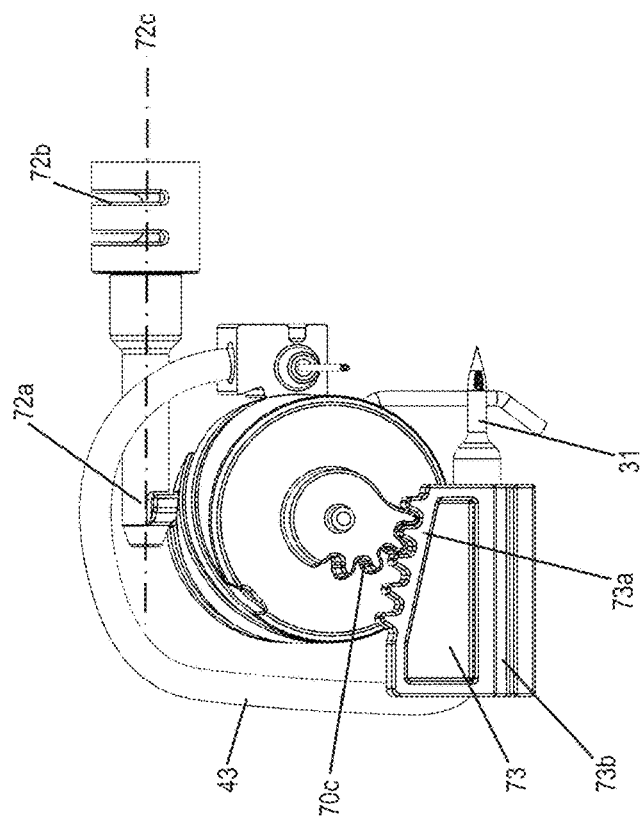
FIG. 31: Detail of the needle insertion mechanism according to the second embodiment, needle retracted position showing the gearing on the steering drum for driving the spike carrier.

A view from the bottom of the device of a detail of the needle insertion mechanism according to the second embodiment is shown in FIG. 31. The steering drum (70) has a gearing (70*c*) which is attached or attachable to the bottom surface and/or longitudinal axis of the steering drum (70). The gearing is preferably composed as a toothing which matches a corresponding toothing (73*a*) on a spike carrier (73) which carries the spike (31) that can be inserted in a reservoir, preferably having a septum. The spike carrier (73) has a guiding means or guiding slot (73*b*) which is preferably engaged with the housing and guides the spike carrier (73) as the carrier is driven towards the reservoir.

Figure 33:
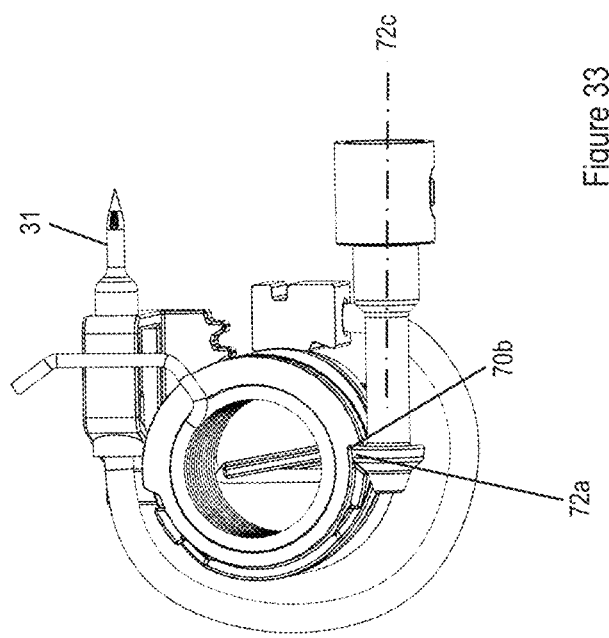
FIG. 33: Detail of the needle insertion mechanism according to the second embodiment, needle inserted position after the steering drum rotated over a first angle, spike carrier in inserted position.
Figure 32:
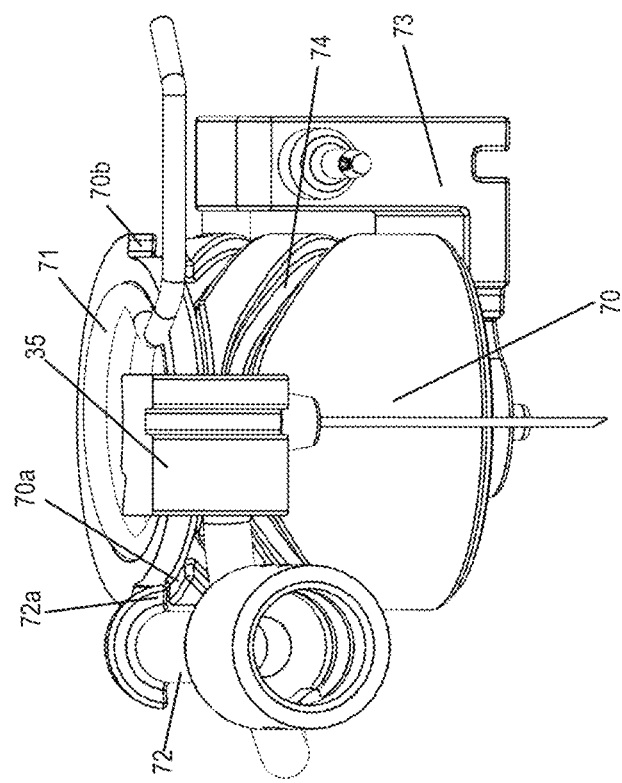
FIG. 32: Detail of the needle insertion mechanism according to the second embodiment, needle retracted position showing the rotation of the stop means over the first stop means angle to release the first arrester.
Figure 34:
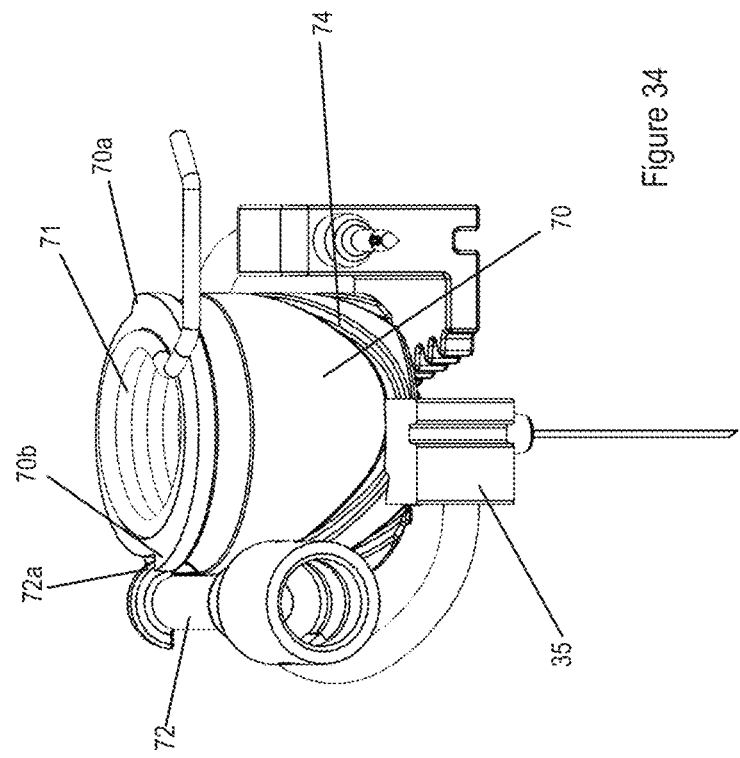
FIG. 34: Detail of the needle insertion mechanism according to the second embodiment, needle inserted position.

In FIG. 32, the stop means (72) is rotated around the rotational axis (72*c*), for example by the third part (3), such that the counter arrester (72*a*) is moved out of abutment with the first arrester (70*a*) of the steering drum (70), such that the spring (71) rotates the steering drum over a first angle until the stop means (72) catches the second arrester (70*b*), see also FIG. 33. The counter arrester is preferably shaped as a semi-circular arch or rim and rotation of the stop means over the first angle releases the contact between the counter arrester and the first arrester (70*a*), but brings the semi-circular arch or rim within the line or rotation of the second arrester (70*b*). As the steering drum rotates, the guiding means (74) on the steering drum (70) drives the cannula holder (35) to the needle inserted position (FIGS. 33 and 34). The guiding means (74) preferably has a sinus shape and during the rotation of the steering drum (70), the transformation means of the cannula holder (35) is driven by the guiding means (74) as the guiding means rotates and the transformation means goes from the maximum of the sinus shaped curve to the minimum. The cannula holder (35) is linearly guided by the housing as it moves to the needle inserted position.

Figure 35:
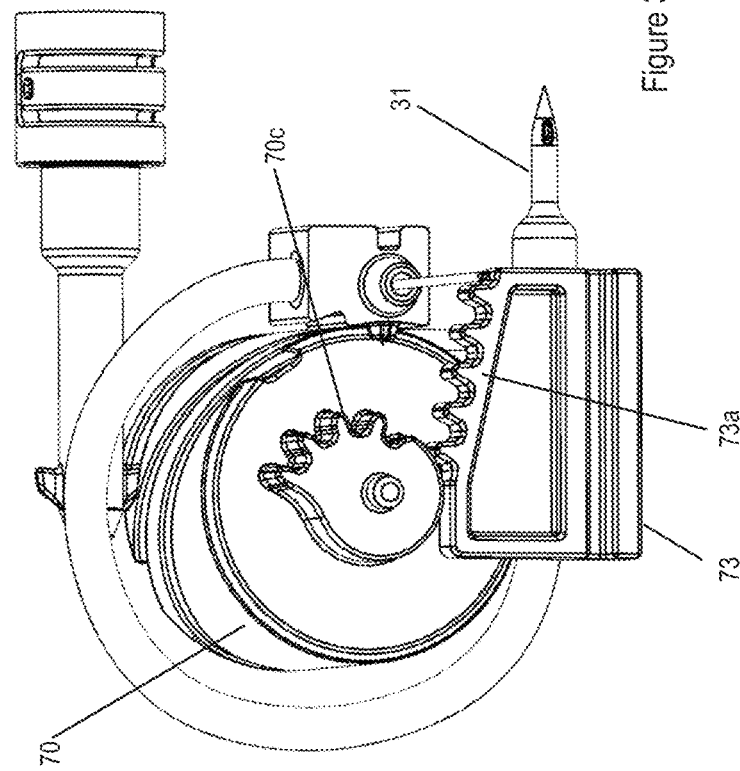
FIG. 35: Detail of the needle insertion mechanism according to the second embodiment, needle inserted position showing the gearing for driving the spike carrier into the inserted position.

During rotation of the steering drum (70), the gearing (70*c*) drives the spike carrier (73) towards the reservoir, as presented in FIG. 35. The spike carrier is guided by the housing, preferably in a direction perpendicular to the movement of the cannula holder.

Figure 37:
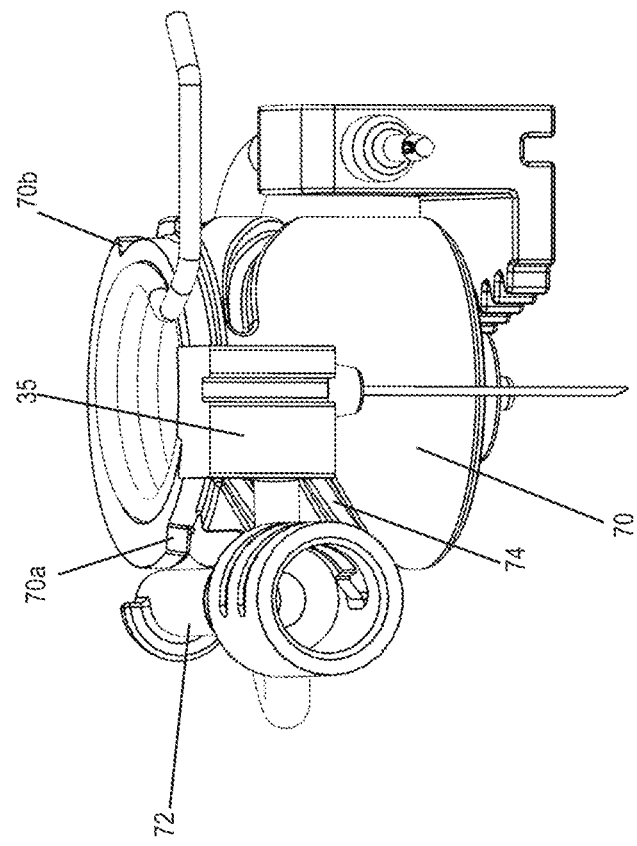
FIG. 37: Detail of the needle insertion mechanism according to the second embodiment, steering drum has rotated over a further angle to retract the cannula holder.
Figure 36:
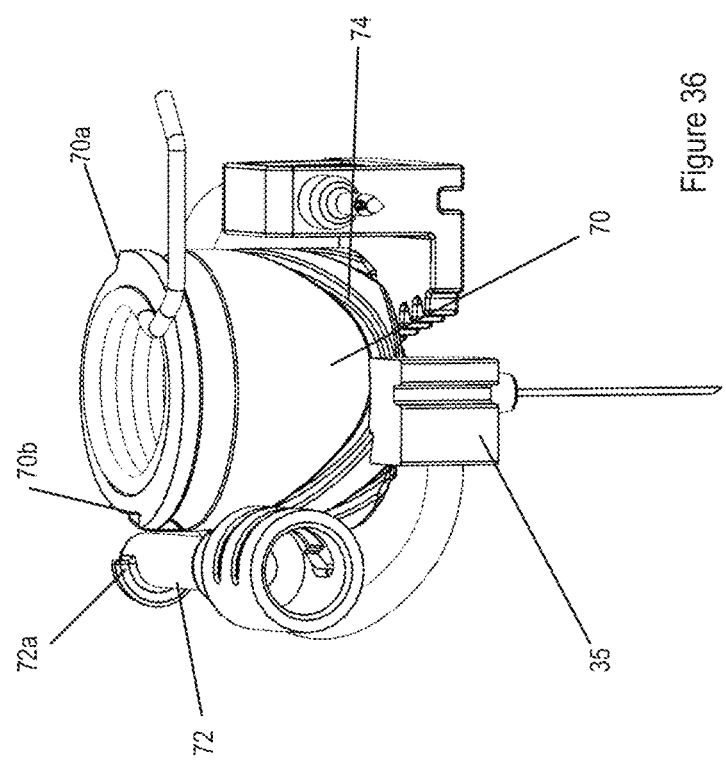
FIG. 36: Detail of the needle insertion mechanism according to the second embodiment, stop means rotated over a further angle to release the engagement with the second arrester.

The release of the second arrester (70*b*) with the counter arrester (72*a*) of the stop means (72) is shown in FIG. 36. The stop means (72) is rotated further in the same direction as the first rotation for releasing the first arrester, the stop means (72) is rotated over an angle that is greater in magnitude as the first rotation angle. The zero angle position is hereby defined by the starting position of the stop means (72) when the counter arrester (72*a*) abuts the first arrester (70*a*) of the steering drum (70). The release of the second arrester (70*b*) ensures that the spring or biasing means (71) can rotate the steering drum (71) further in the same rotation direction as the first rotation. The further rotation of the steering drum (70) ensures that the guiding means (74) drives the cannula holder (35) back to the needle retracted position as the guiding means goes from the minimum to the maximum of the sinus curve (FIG. 37). The cannula holder is guided by the housing during the axial shift. The spike inserter is not moved during the further rotation after releasing the second arrester since there are no engaging teeth between the gearing and the inserter (FIG. 35).

Figure 38:
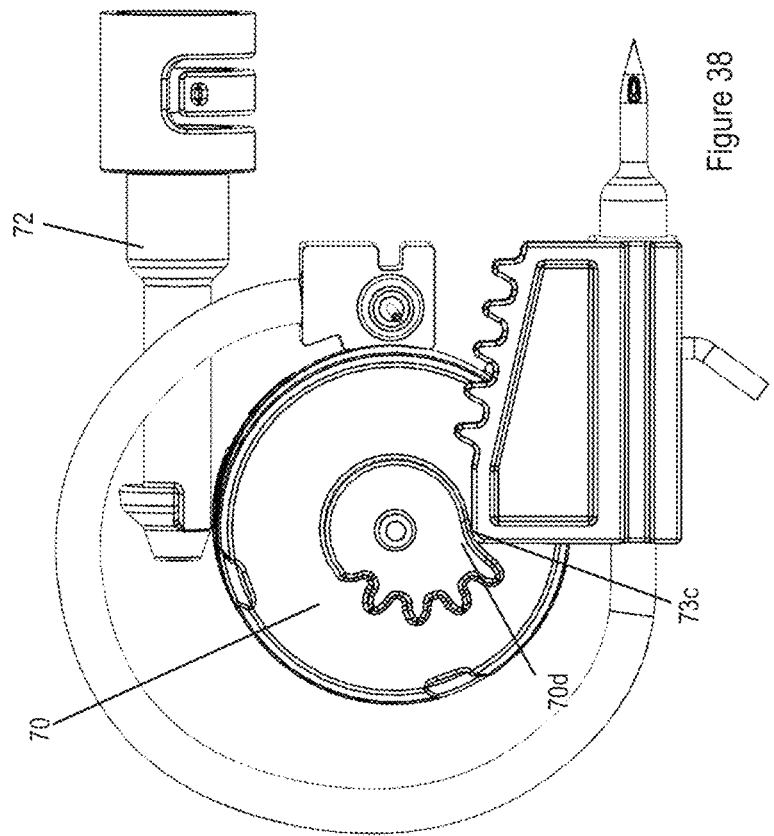
FIG. 38: Detail of the needle insertion mechanism according to the second embodiment, showing the stops between the gearing and the spike carrier.

The rotation of the steering drum (70) after releasing the second arrester (70*b*) is halted when a gearing stop (70*d*), which is part of the gearing (70*c*), abuts a stop on the housing, or preferably a stop (73*c*) on the spike carrier, FIG. 38.

Figure 39:
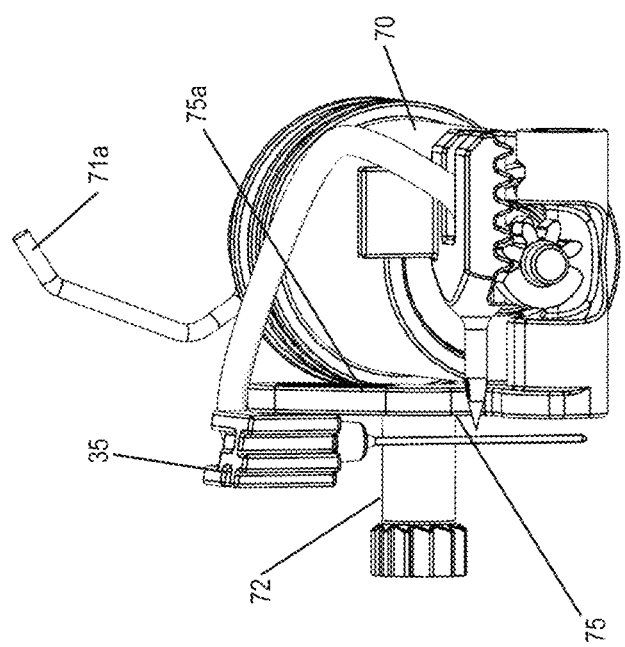
FIG. 39: Detail of the needle insertion mechanism according to the third embodiment, needle retracted position.
Figure 40:
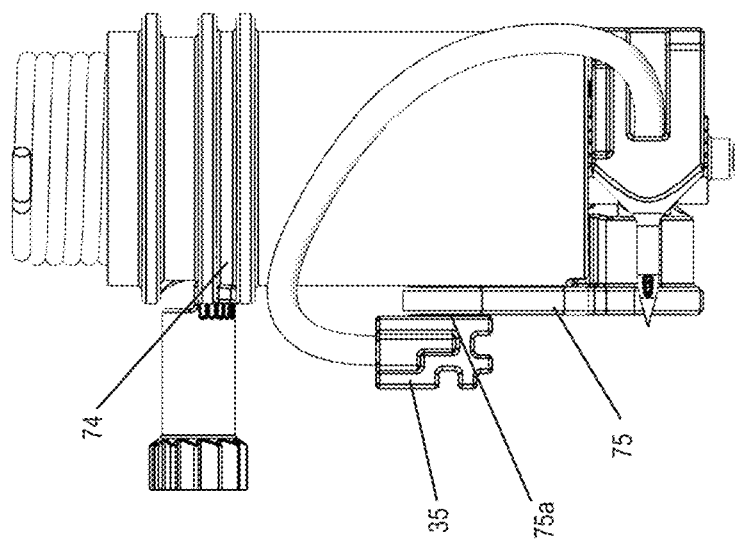
FIG. 40: Detail of the needle insertion mechanism according to the third embodiment, needle retracted position.
Figure 40C:
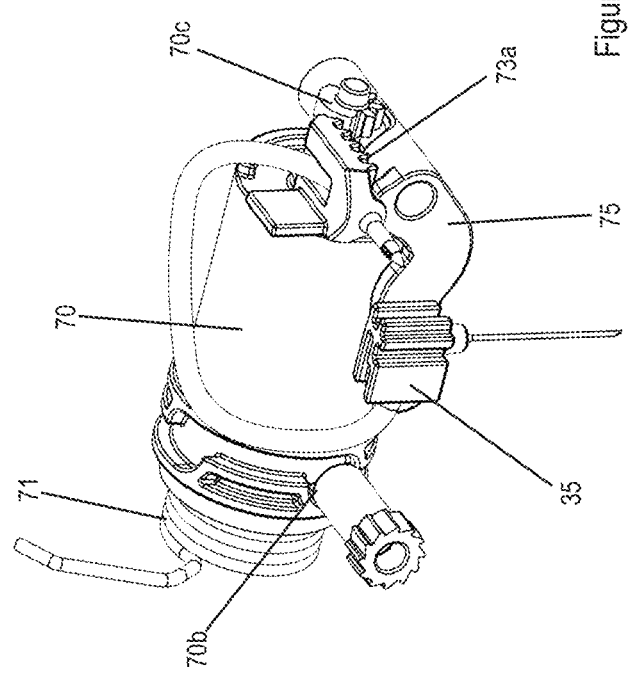
FIG. 40c: Detail of the needle insertion mechanism according to the third embodiment, needle inserted position.
Figure 40B:
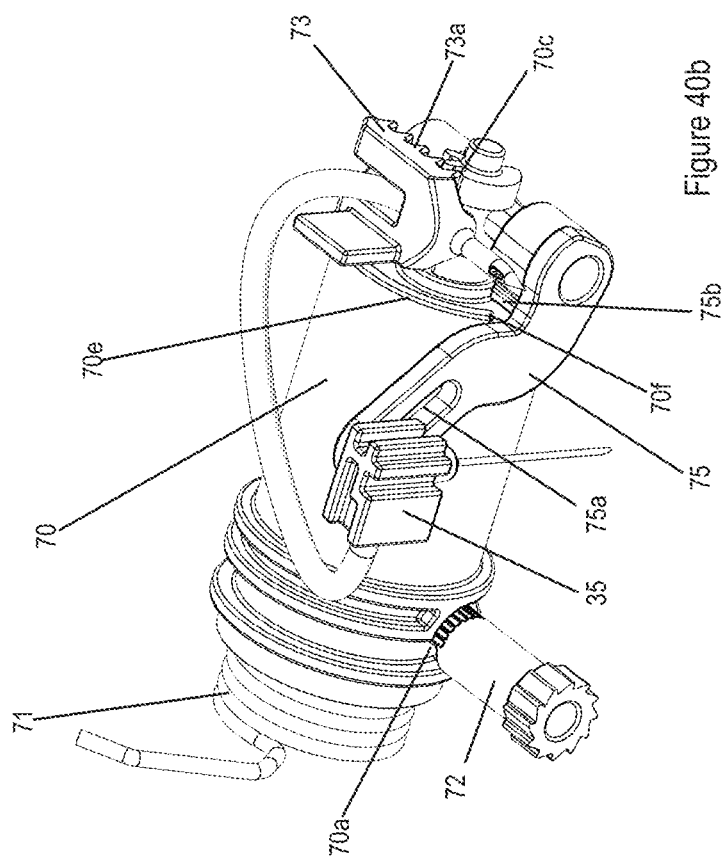
FIG. 40b: Detail of the needle insertion mechanism according to the third embodiment, needle retracted position.

A needle insertion mechanism according to a third embodiment is presented in FIGS. 39 and 40. The rotational axis of the steering drum (70) is preferably oriented parallel to the bottom surface of the device. The stop means (72) has a toothing on one end which can be coupled to another part, preferably the third part (3). The steering drum (70) is biased by a spring and rotation of the stop means (72) releases the steering drum (70) to rotate over an angle until the stop means catches or abuts the second arrester. A gearing is connected to the longitudinal axis which inserts a spike carrier via the gearing mechanism as the steering drum rotates over the first angle. The gearing has a toothing and the toothing advances the spike as the steering drum rotates. Rotation of the steering drum furthermore rotates a lever arm (75), to drive the cannula holder towards the patients skin via a guide opening (75*a*) in the lever arm (75) that is adapted to be connected or connectable to the cannula holder (35). Further rotation of the stop means ensures that the steering drum is also rotated further and the lever arm moves the cannula holder back towards the needle retracted position. The torsional spring (71) biases the steering drum (70) which is held in its position by the stop means (72) abutting the first arrester (70*a*) of the steering drum (70), see FIG. 40*b*. Gearing (70*c*) is attached to the end of the steering drum, the gearing having a toothing which matches corresponding toothing (73*a*) of the spike carrier (73). The spike carrier (73) has a wing which ensures that the carrier can be guided by the housing for a linear movement. The steering drum (70) has a circumferential rim (70*e*) located at the end of the steering drum (70). The lever arm (75) has the guide slot (75*a*) for guiding the cannula holder (35) from the needle retracted to the needle inserted position by rotation of the lever arm. Rotation of the stop means (72), releases the abutment with the first arrester (70*a*) and the steering drum (70) starts rotating until the stop means (72) abuts the second arrester (70*b*, FIG. 40*c*). Rotation of the steering drum ensures that the end (70*f*) of the rim (70*e*) abuts a steering element (75*b*) which is part of the lever arm (75) and ensures that the lever arm starts rotating. Rotation of the lever arm drives the cannula holder (35) from the needle retracted to the needle inserted position (FIG. 40*c*). During the rotation of the steering drum (70) the gearing (70*c*) ensures that the spike (73) is moved and inserted in the reservoir. The rotation of the lever arm 75 is halted by a second steering element or second stop (75*c*, FIG. 40*d*), which is part of the lever arm mechanism and the second steering element (75*c*) is moved in a recess (70*g*) of the steering drum. As the steering drum is rotated, an abutment between the second steering element (75*c*) and the wall surface of the recess (70*g*) stops the rotation of the lever arm. Once the stop means (72) is rotated over an additional angle, the abutment with the second arrester (70*b*) is released and the steering drum (70) rotates further, whereby the abutment between the second steering element (75*c*) and the recess (70*g*) of the steering drum ensures that the lever arm rotates back and consequently the cannula holder moves back to the needle retracted position.

A first embodiment of the drive mechanism of the medication delivery device is shown in FIG. 41. A segmented piston rod (80) is embodied in a guidance for the piston rod (4f) which is a housing part, which guides the elements from the drive mechanism along a 180° U-turn or curve into the opening of the reservoir (26). This arrangement ensures that the longitudinal axes of the motor for the drive mechanism and the longitudinal axis of the reservoir are oriented parallel to each other to reduce the length of the device. The segmented piston rod (80) is composed of multiple segments (81) which are connected to each other laterally via a hinge (82), preferably via a strap hinge. When subsequent hinges are articulating, the piston rod can curve or bend and when all hinges are closed all segments abut each other on the side opposed to the hinges (82a) to form a stacked configuration. In the latter case, the piston rod behaves like a rod, quasi like a non-segmented piston rod for efficient load transfer. The segmented piston rod preferably has a drive segment (81a), which is typically the first segment. The drive segment (81a) preferably has an internal thread segment that matches the outside threading of the threaded rod (15). The threaded rod (15) is rotated by an electromotor (83) which drives the threaded rod via a gearing (84) in combination with a worm wheel (85). The number of rotations is measured by an encoder (86) which is either part of the electromotor or as a separate optical system using, for example, a LEO light source, an external disc shaped chopper in combination with an optical sensor or magnetically controlled sensor (not shown). Rotation of the threaded rod (15) advances the drive segment (81pa) of the piston rod as the piston rod is prevented from rotation by the housing part (4f). Subsequent segments are advanced via the hinges.

Advancement of the drive segment (81a) advances transfer segments (81b) which are adjacent to the drive segment and which are U-shaped to enclose the threaded rod (15). The transfer segments (81b) are connected to delivery segments (81c) which are intended for making the U-turn and for partially entering the reservoir. The last segment (81d) of the piston rod (81) has a flange (81e) or connector for connecting to the plunger (28) of the reservoir.

The guidance (4f) of the segmented piston rod (82) in the housing is illustrated in FIG. 41a. The guidance (4f) guides the segmented piston rod such that the piston rod is bent in one direction and guided towards the entrance of the reservoir. For guiding the piston rod, each segment has two wings (81h, 81i) which extend from each segment (81) and fit into a guide slot (4p) of the guidance (4f) for the piston rod. The guide slot (4p) in combination with the wings (81h, 81i) ensure that the piston rod cannot rotate and that the piston rod is bent during advancement of the segments.

Advancement of the piston rod advances the plunger in the reservoir until the reservoir has been emptied as presented in FIG. 42. The number of revolutions for emptying the reservoir are typically recorded by the sensor system having an encoder and the data are transmitted to the processor of the device. The processing unit can use the data for the control of the coupling mechanism described above. The last segment (81d) of the segmented piston rod has a guiding means (87), preferably shaped as a fin which points into the direction of the next-to-last segment. The guiding means can pass through notches of the segments adjacent to the last segment (81d), preferably through a notch or groove suitable for receiving the guiding means when the segmented piston rod transfers from the curved to the linear configuration. The guiding means (87) does not interfere or engage with the segments adjacent to the last segment, e.g. the groove or notch does not interfere with the fin shaped guiding means. The guiding means is preferably also guided by the housing part (4f) prior to entering the reservoir, for example by a cut-out (4i) of the housing or housing part (4f).

Figure 46:
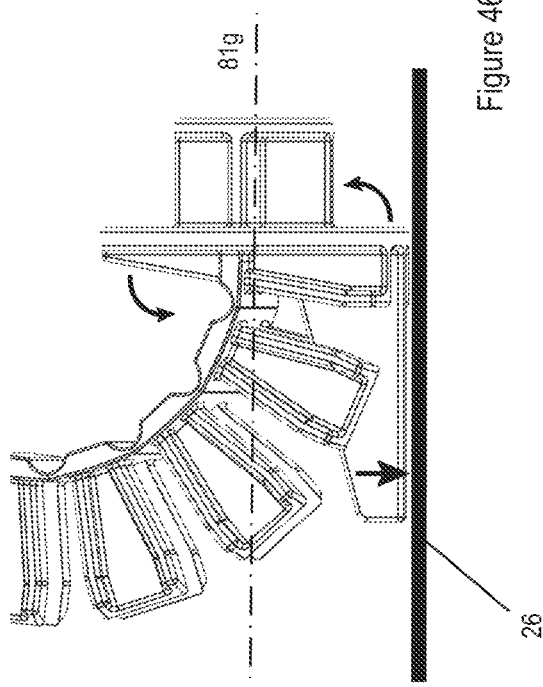
FIG. 46: Schematic drawing showing the force vectors that intend to tilt the last segment and how this is counteracted by the guiding element.

The guiding means has an edge (87a) which is directed parallel to the normal (81g) (e.g., normal axis) of the last segment (81 d). When entering the cartridge, the edge (87a) interferes with the wall of the reservoir (26) and/or cut-out (4i) of the housing, and thereby guiding the last segment (81d) such that the flange (81e) is prevented from off-axis entrance into the reservoir, thereby enabling an efficient loading of, or coupling to the plunger and preventing blockage or buckling of the segmented piston rod (80) in the reservoir. The correct guidance of the last element (81d) is transmitted to the adjacent elements due to the hinged connection which is stiff enough to withstand any warpage between the elements. The guiding means (87) or fin partially functions as a lever arm and thereby arranging a parallel orientation of the normal of the last segment (81g) and the longitudinal axis of the reservoir. The guiding means or fin also prevents fitting of the last segment once connected to the plunger, the tilting forces are compensated for by the interaction between the fin and the inner wall of the reservoir (FIG. 46). The fin is positioned opposite to the hinge axis of the strap hinge and the plane of the fin is oriented perpendicular to the hinge axis with the edge (87a) facing the inner wall of the reservoir.

Figure 44:
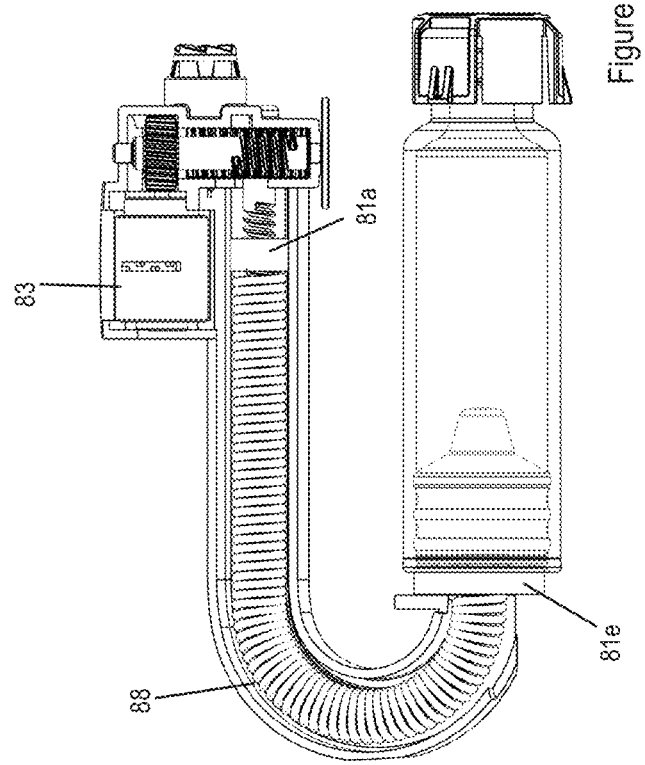
FIG. 44: Drive mechanism of the injection device according to a second embodiment with a spring-type piston rod.
Figure 43:
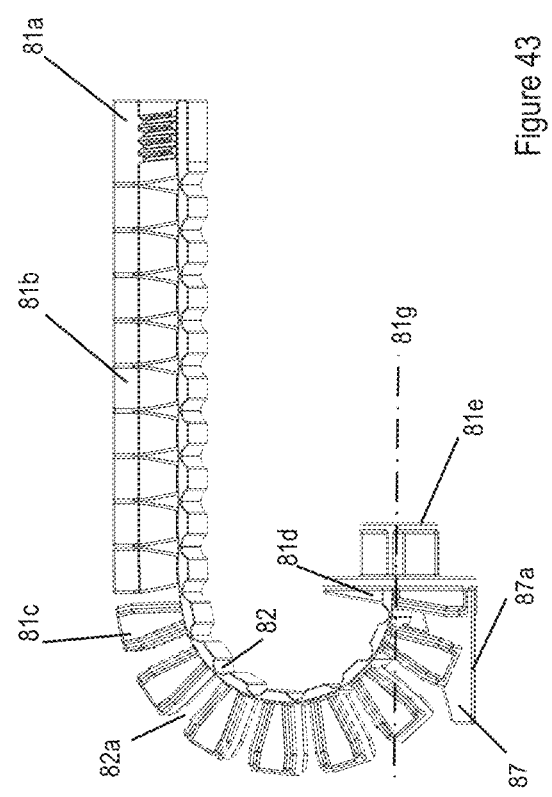
FIG. 43: Segmented piston rod according to the first embodiment.

A second embodiment of the drive mechanism is presented in FIG. 44, using a spring or coil (88) instead of the segmented piston rod. The spring (88) preferably is a close wound-up helical coil and the windings of the spring can bend versus adjacent windings such that the spring can form the U-turn before entering the reservoir. A flange (81e) is attached or attachable to one end of the spring for abutting the plunger of the reservoir. On the other end of the spring, a nut element (81a) is attached to the spring having an internal threading matching an external thread of the threaded rod. Rotation of the threaded rod advances the spring-type piston rod, alike the first embodiment.

Figure 45:
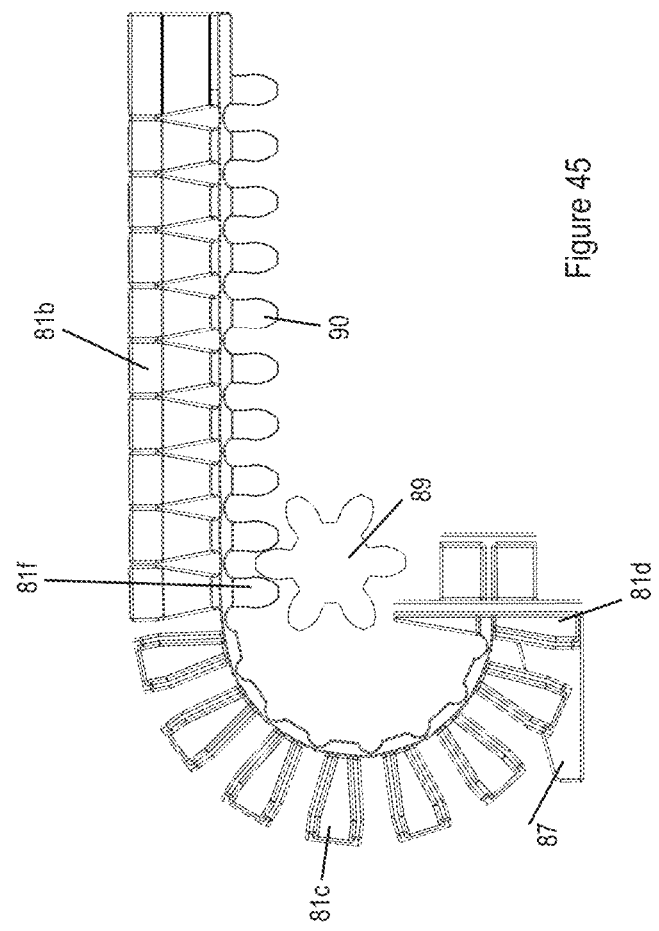
FIG. 45: Drive mechanism of the injection device according to a third embodiment, drive mechanism operates a gear wheel for advancing the piston rod.

A third embodiment of the drive mechanism is shown in FIG. 45, the transfer segments (81b) are equipped with a teething forming a toothed rack that matches a gear wheel (89) and rotation of the gear wheel advances the segmented piston rod.

In FIG. 46, a schematic representation is shown of the forces acting upon the last segment when medication is expelled. The last segment intends to tilt and the guiding element counteract the tilting moment to prevent incorrect abutment of the plunger.

The assembly of the subunits to form an assembled device having a sterile environment for the needle insertion unit, and which can connect to a sterile cartridge will be discussed in the following. In FIG. 47, a filled cartridge (26) is assembled with the cartridge holder (4d) of the subunit comprising the needle insertion and retraction mechanism. The subunit is preferably sterilized, for example using ETO and brought into an aseptic environment, for example in a fill-finish unit. The cartridge (26) is filled with the medication at the fill-finish line in an aseptic environment and closed with a plunger (28). The cartridge is closed with a septum (27) which is connected to the neck of the cartridge using a crimp (27a). The full cartridge is inserted, preferably in the aseptic environment into the opening of the cartridge holder (4a). The cartridge is fixated in the holder with the cartridge fixator (56), which fixates, for example around the neck of the cartridge, the cartridge in the holder to reduce or eliminate axial movements of the cartridge (26) in the holder (4a). In this example, the cartridge is fixated using an ellipsoidal shaped ring that can flex around the crimp of the cartridge. The long axis of the ellipse fits between the neck of the cartridge and the crimp. The cartridge fixator (56) also ensures that the end of the crimp (27a) and/or septum (27) remains in a preferably fluid- and air-tight contact with a sealing element (121) which is part of the cartridge holder. The sealing element preferably is made from an elastic material and after insertion there is a sealing between the end of the cartridge, e.g. the crimp and/or septum, and the sealing element (121) which ensures that there is a sterile barrier between the cartridge and the cartridge holder. Since the parts of the needle insertion and retraction unit which are within the needle housing cover (4l) were already sterile, the sterility remains guaranteed while the assembly of the cartridge holder and cartridge is outside the sterile environment. Additionally, the passage (4n) for the needle needs to be sealed by a sterile barrier and the connection to the coupling mechanism requires a sterile sealing as described above. The sterile barrier element forms a sterile enclosure (120) which encloses the fluid path unit and which is indicated as a thick line in FIG. 47. The device can now be assembled with the bottom housing part (4g) and the housing cover (4j), which can be done outside the sterile environment.

Figure 48:
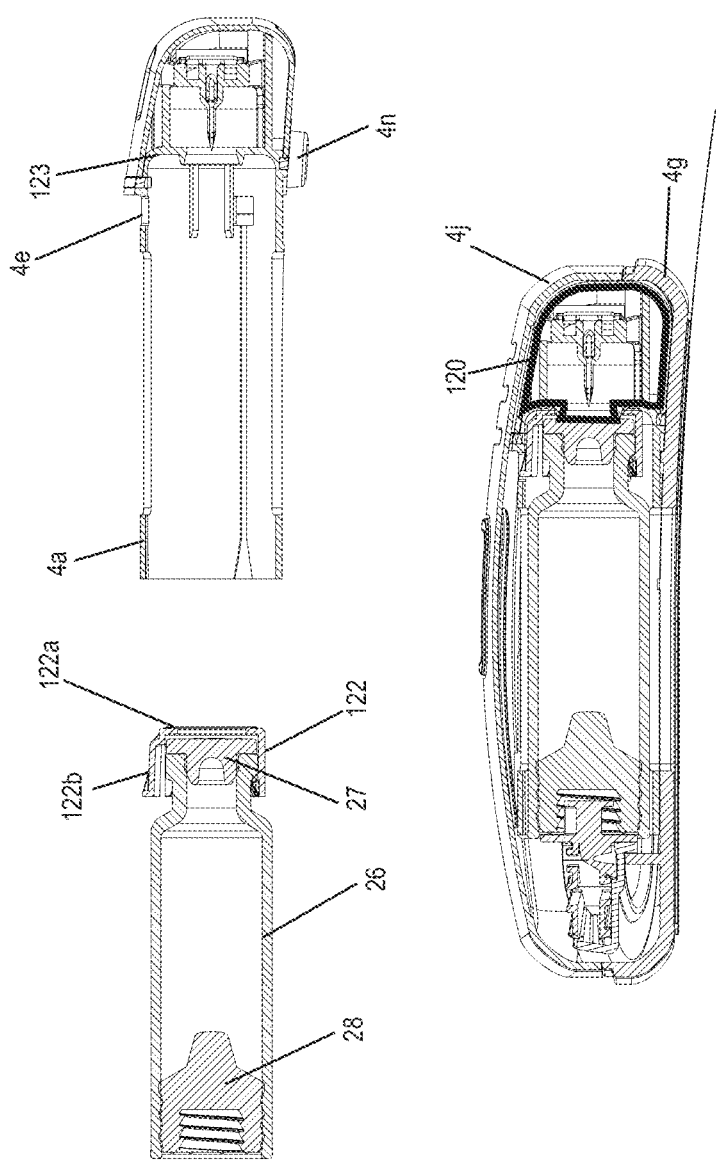
FIG. 48: Assembly of the cartridge in the cartridge holder, connector and crimp integrated in one part with the sterile barrier at the front of the cartridge.

An alternative for the sterile barrier between the cartridge (26) and the housing of the fluid path is shown in FIG. 48. In this example, there are several functionalities combined in the sealing element (122). The sealing element (122) has a sealing surface (122a) which, once in abutment with a counter surface of the fluid path unit, ensures a sterile barrier. The crimp combines the features of providing a stable and sterile connection between the glass barrel of the cartridge (26) and the septum (27), a mechanical connection to the cartridge holder using connector (122b) which can snap fit into passage (4e) of the holder, and finally a sterile barrier between the cartridge and the cartridge holder using sealing surface (122a) and counter surface (123) of the cartridge holder. The sterile barrier or sterile enclosure is indicated with (120). The assembly of the device with the bottom surface (4g) and housing cover (4j) is described above.

Another alternative for the cartridge fixation and sterile barrier configuration is presented in FIG. 49. The cartridge fixator (56) is tubular shaped and at least partially encloses the cartridge (26). The cartridge fixator is attachable to the needle insertion unit via a snap fit connection using flexural element or a screw type of connection. The connection between the cartridge fixator (56) and the needle insertion unit is such that is forms a tight and sterile barrier. The tubular shaped fixator (56) is open on one end to receive the cartridge end with the plunger. A sterile barrier (56a) is located on the opposite end of the fixator (56), preferably shaped to receive connector (81e) of the last segment (81d) of the segmented piston rod (80). After aseptic assembly of the cartridge (26) with the fixator (56), the whole cartridge is enclosed in a sterile environment or sterile enclosure (120) during shelf life. Once the bolus is injected from the device, the advancement of the piston rod punctures the sterile barrier (56a) for advancing the plunger (28). The sterile barrier (56a) is preferably made from a material that combines a sterility barrier but enables the connector (81e) of the last segment to penetrate the barrier, e.g. it is made from a paper (cellulose) type of material or Tyvek. The connector (81e) can be equipped with a puncturing device such as a sharp tip or fin which is an integral part of the last segment.

In FIG. 49a, an example is presented for an assembly of an empty cartridge (26) that is inserted into the cartridge holder (4d) with the needle insertion and retraction mechanism. Both the cartridge and the needle insertion subunit comprising the cartridge holder (4d) are brought into an aseptic environment, assembled and packaged again, preferably in a sterile tub. The packaged subunits comprising the empty cartridge are subsequently brought to a fill-finish line where the subunits are removed from the packaging the subunits are filled and stoppered with a plunger in an aseptic environment.

The subunit comprising the needle insertion and retraction mechanism is assembled such that the medication in the cartridge remains in a sterile environment from the assembly throughout shelf-life and subcutaneous delivery. The subunit has at least three passages to the ambient, the passage for the coupling device, for example the third part (3), the connection to the reservoir (26) as described above and the passage (4n) for the needle. The latter is described in the following paragraphs.

Figure 51:
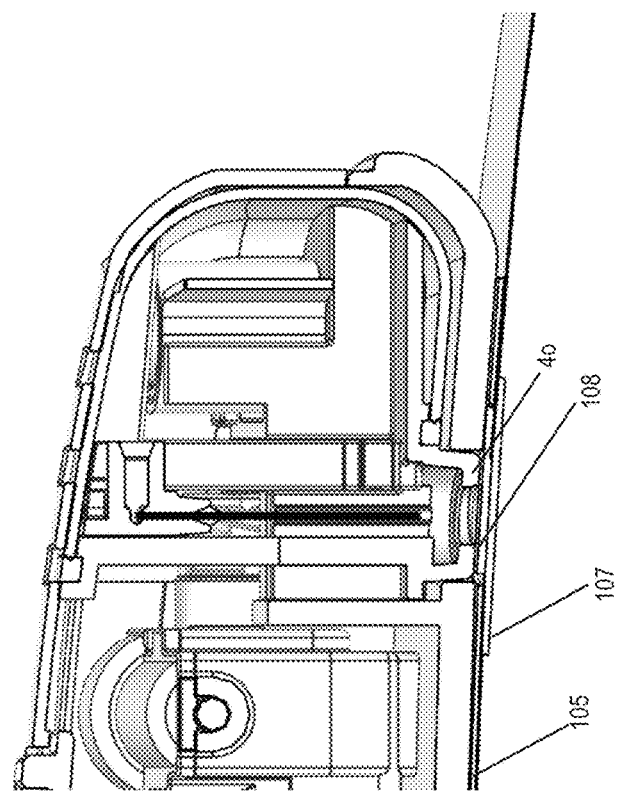
FIG. 51: Assembly of the needle insertion unit with the bottom and top cover part: Sterile closure of the needle passage using a separate sticker to release the sterile barrier.
Figure 50:
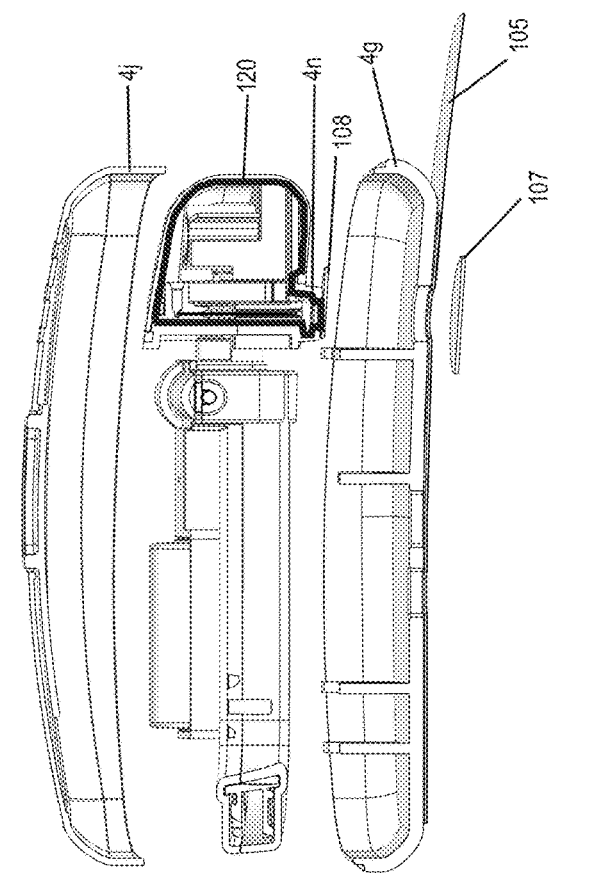
FIG. 50: Assembly of the needle insertion unit with the bottom and top cover part: Sterile closure of the needle passage using a separate sticker to release the sterile barrier.

In FIGS. 50 and 51, the passage (4n) for the needle is closed by a peel foil (108) which is attached to the end surface (4o) of the passage. The peel foil (108) can be made from a gas permeable material like Tyvek to enable gas-plasma or ethylene oxide sterilization of the compartment inside the housing cover (4j) comprising the needle insertion unit. Alternatively, the foil is made from a barrier film such as PET or PE/PA multilayer foil if other sterilization techniques such as gamma or e-beam are used. After assembly of the cartridge, a sterile enclosure (120) surrounds the needle insertion mechanism as is schematically indicated with a thick line. The needle insertion subunit preferably already comprises the peel foil (108) which is attached to the end surface (4o) using welding, ultrasonic welding or gluing techniques. The subunit is assembled with the top cover (4j) and bottom surface (4g) and an additional sticker or adhesive foil (107) is attached or attachable to the peel foil of the adhesive layer (105). The sticker (107) makes the connection between the peel foil (105) of the adhesive layer and the peel foil (108) of the insertion unit, e.g. it adheres both to both foils. The assembly of the stacked peel foils is presented in FIG. 51, the user removes the peel foil (105) of the adhesive layer (104) and, via the sticker (107), releases the bonding between the end surface of the passage (4o) and the sterile peel foil (108). Another example for the closure of the passage (4n) is presented in FIG. 52. The needle insertion sub-unit is closed by the peel foil (108) forming a sterile barrier alike the previous example. However the bottom surface (4g) comprises a peel foil (105) for the adhesive layer (104) which closes the passage (106) of the bottom surface. In the assembled device, the peel foil (105) of the bottom surface directly contacts and adheres to the sterile peel foil (108) of the needle insertion sub-assembly. The adhesive contact can be, preferably, due to a separate adhesive layer either present on the surface of one of the two peel foils (105, 108).

Figure 53:
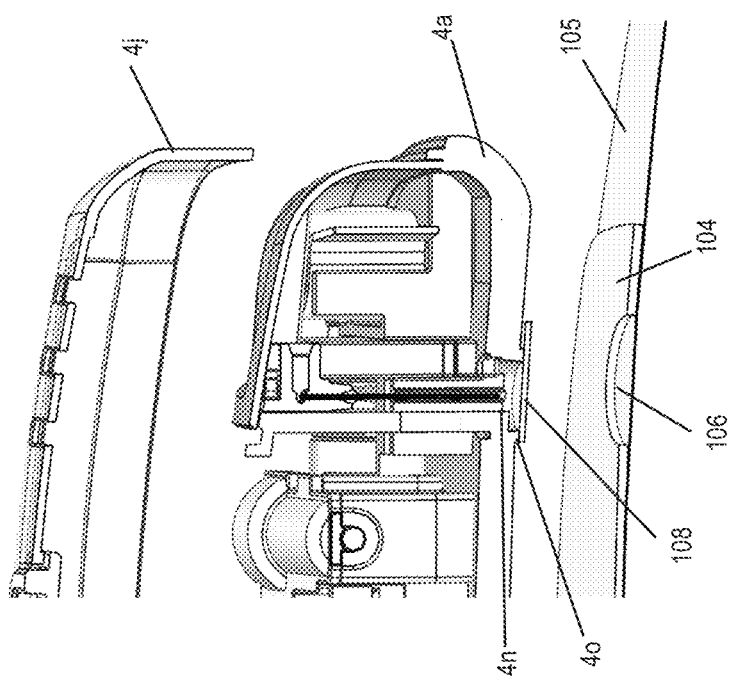
FIG. 53: Assembly of the needle insertion unit with the top cover part: The bottom surface of the device is integrated with the needle insertion sub-unit; sterile barrier is released together with the peel foil of the adhesive layer.
Figure 52:
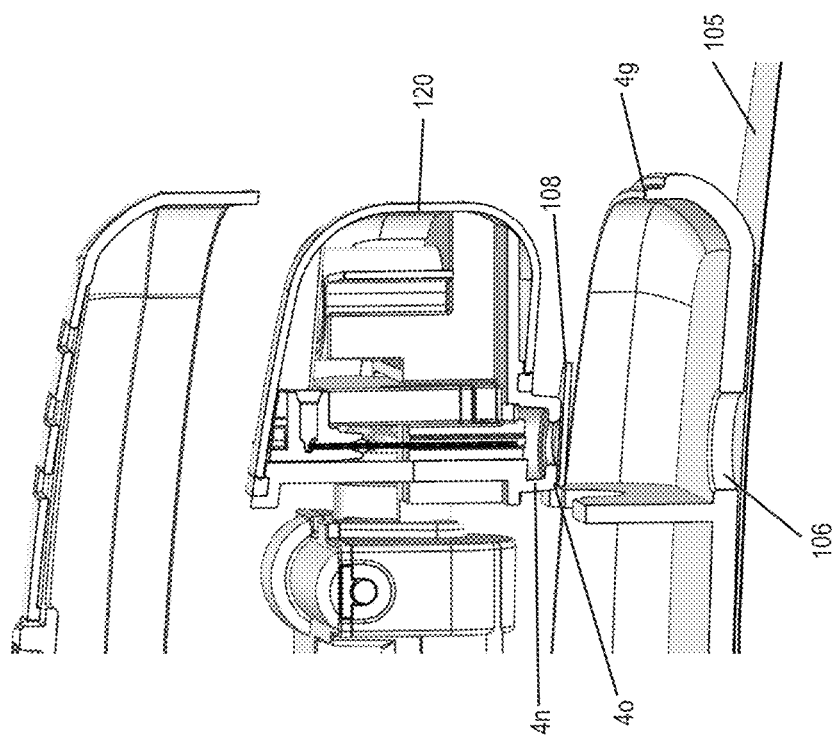
FIG. 52: Assembly of the needle insertion unit with the bottom and top cover part: Sterile closure of the needle passage using a sterile barrier that is released together with the peel foil of the adhesive layer.
Figure 55:
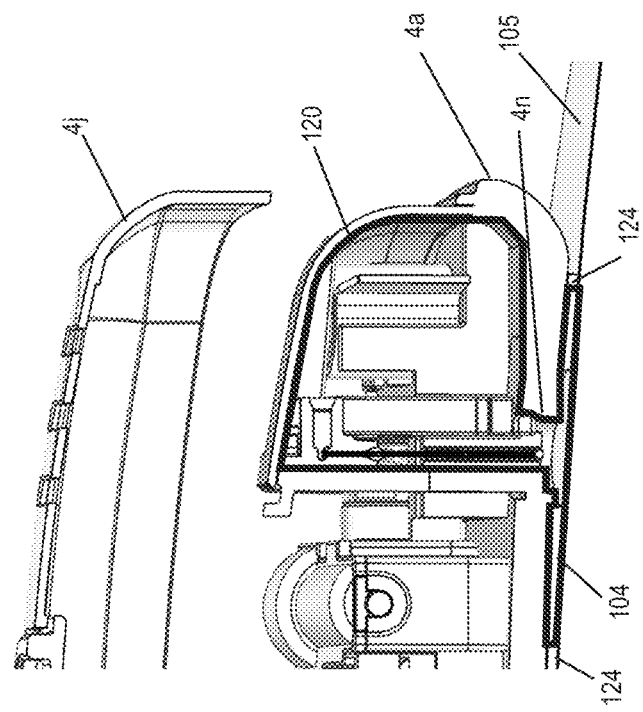
FIG. 55: Assembly of the needle insertion unit with the top cover part: The bottom surface of the device is integrated with the needle insertion sub-unit; Peel foil of the adhesive layer forms the sterile barrier.
Figure 54:
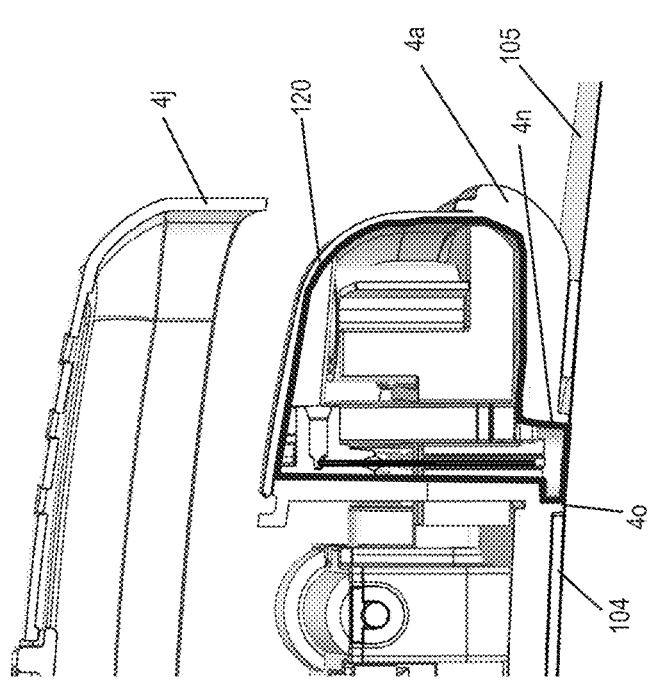
FIG. 54: Assembly of the needle insertion unit with the top cover part: The bottom surface of the device is integrated with the needle insertion sub-unit; Peel foil of the adhesive layer forms the sterile barrier.

In the examples of FIGS. 50 to 52, the bottom surface (4g) is a separate housing part. In FIGS. 53 to 55, examples are presented where the bottom surface is not a separate housing part but is integrated with the needle insertion and retraction sub-assembly.

In FIG. 53, the passage (4n) of the needle insertion compartment is closed with the peel foil (108) as described above. The bottom surface of the device is integrated with the needle insertion sub-assembly and the adhesive layer (104) and top cover (4j) are attached to the sub-assembly. In this example, there is a direct contact envisaged between the foils (105) and (108) alike the example of FIG. 52, but as an alternative also a sticker (107) can be used to contact the peel foil (105) of the adhesive layer to the sterile foil (10), alike the example described in FIG. 50.

In yet another example, no separate foil (108) closes the passage (4n) of the needle insertion compartment, see FIG. 54. The sterile barrier from the inside of the compartment to the ambient is governed by the peel foil (105) for the adhesive layer (104). This implies that the adhesive layer including the peel foil (10) are already attached to the bottom surface of the needle insertion sub assembly when the cartridge (26) is inserted or that the compartment itself is sterilized in a final sterilization step. The peel foil (105) is attached or attachable to the end surface (4o) of the passage (4n) for the needle as shown in FIG. 54 or the peel foil is not connected to the end surface (4n) as presented in FIG. 55. In the latter case, sterile barriers are required at the rim of the adhesive layer or which are integrated within the surface of the adhesive layer, which is indicated with (124) in FIG. 55. The sterile enclosure of the example presented in FIG. 55 encloses the fluid path which is in the housing of the needle insertion subassembly, encloses the passage for the needle (4n) and the adhesive layer (104). The sterile enclosure is schematically indicated as the thickened line (120) in FIG. 55.

The adhesive layer (104) ensures that the device can be attached to the skin of the patient after removing the peel foil (105). For removing the device after the injection, the adhesive layer may have a lid, or a part attached to the adhesive layer that can easily be held or grabbed by the patient to remove the device from the skin, the lid preferably having an area with non-skin adhering properties.

| [174] Part annotation |
| --- |
| (1) Ratchet shaft, first part |
| (2) Coupling member, second part |
| (3) Cam shaft, third part |
| (4) Housing |
| (4a) Housing fluid path unit |
| (4b) Spring holder |
| (4c) Vertical wall housing |
| (4d) Cartridge holder |
| (4e) Passage for cartridge fixator |
| (4f) Guidance for piston rod |
| (4g) Bottom housing part |
| (4h) Drive carrier part |
| (4i) Cut-out housing part |
| (4j) Housing cover |
| (4k) Button |
| (4l) Needle housing cover |
| (4m) Window |
| (4n) Passage for needle |
| (4o) End Surface passage |
| (4p) Guide slot |
| (5) Toothing |
| (6) Gearing, threading, guide slot |
| (7) Flange |
| (8) O-ring, friction element |
| (9) Notch |
| (10) Pin, protrusion, thread segment |
| (11) Asymmetric toothing, second part |
| (12) Asymmetric toothing, third part |
| (13) Cam, coupling member third part |
| (14) Gear wheel |
| (15) Threaded rod |
| (16) Toothing gear wheel |
| (17) Bearing member |
| (18) Thread on threaded rod |
| (19) Rotational axis |
| (20) Sealing element, second friction fit |
| (21) Needle control element |
| (22) End surface third part |
| (23) End surface second part |
| (24) Bottom surface |
| (25) Fluid path unit |
| (26) Reservoir |
| (27) Septum |
| (27a) Crimp |
| (28) Plunger, plug, stopper |
| (29) Longitudinal axis reservoir |
| (30) Spike inserter carrier |
| (30a) Base surface spike inserter carrier |
| (30b) Longitudinal axis |
| (31) Spike |
| (31a) Tip |
| (31b) Base spike |
| (32) First position spike inserter carrier |
| (33) Second position spike inserter carrier |
| (34) Biasing means, spring |
| (34a) End of spring, lever arm |
| (35) Cannula holder |
| (35a) Abutment surface |
| (35b) Catch for locking mechanism |
| (36) Cannula, needle |
| (37) Needle retracted position |
| (38) Needle inserted position |
| (39) First guiding means of spike inserter carrier |
| (40) Transformation means on cannula holder |
| (41) Needle control element |
| (41a) Locking arm |
| (41b) End locking arm |
| (41c) Needle retraction arm |
| (41d) First key needle control element |
| (41e) Second key needle control element |
| (41f) Guiding contour needle control element |
| (42) Arrester |
| (43) Tubing |
| (44) Guide slot on housing for spike inserter carrier |
| (45) Inclination angle first guiding means |
| (46) Inclination angle second guiding means |
| (47) First angle of rotation needle control element |
| (48) Second arrester |
| (49) Second angle of rotation needle control element |
| (50) Linear guide housing |
| (51) Second guiding means spike inserter carrier |
| (52) Third guiding means on housing |
| (53) Fourth guiding means on housing |
| (54) Rotation around first key |
| (55) Cams of third part |
| (55a) First cam |
| (55b) Second cam |
| (56) Cartridge fixator |
| (56a) Sterile barrier cartridge fixator |
| (70) Steering drum |
| (70a) First arrester steering drum |
| (70b) Second arrester steering drum |
| (70c) Gearing |
| (70d) Gearing stop |
| (70e) Rim on steering drum |
| (70f) End of rim |
| (70g) Recess |
| (71) Biasing means, torsional spring |
| (71a) End of spring |
| (72) Stop means |
| (72a) Counter arrester |
| (72b) Coupling member |
| (72c) Rotation axis |
| (73) Spike carrier |
| (73a) Toothing |
| (73b) Guiding slot |
| (73c) Stop |
| (74) Guiding means steering drum |
| (75) Transformation means, lever arm |
| (75a) Guide slot lever arm |
| (75b) Steering element |
| (75c) Second steering element, second stop |
| (80) Segmented piston rod |
| (81) Segment |
| (81a) Drive segment, first segment |

-continued

| [174] Part annotation |
| --- |
| (81b) Transfer segment |
| (81c) Delivery segment |
| (81d) Last segment |
| (81e) Flange, connector to plunger |
| (81f) Teeth |
| (81g) Normal last segment |
| (81h) Wing |
| (81i) Wing |
| (82) Hinge |
| (82a) Opposite side hinge |
| (83) Motor |
| (84) Gearing |
| (85) Worm wheel |
| (86) Encoder |
| (87) Guiding element, fin |
| (87a) Edge guiding element |
| (88) Spring type piston rod |
| (89) Gear wheel |
| (90) Toothing |
| (100) Optical indicator, LED |
| (101) Control unit |
| (102) Battery |
| (103) Capacitive sensor |
| (104) Adhesive layer |
| (105) Peel foil adhesive layer |
| (106) Passage |
| (107) Sticker-connector |
| (108) Peel foil, sterile barrier |
| (120) Sterile barrier, Sterile enclosure |
| (121) Sealing element |
| (122) Crimp with sealing element |
| (122a) Sealing surface |
| (122b) Connector |

What is claimed is:

1. A segmented piston rod for an injection device for delivering a medication from a reservoir comprising a stopper, the segmented piston rod comprising:
   a plurality of segments joined together via a hinge located on one side of each of the plurality of segments such that the segmented piston rod can be bent in one direction in a curved configuration by articulating subsequent hinges while an axial force can be transmitted by the segmented piston rod to the stopper when the subsequent hinges are closed in a linear configuration and the segments abut each other on an opposite side of the hinge from the one side,
   the segmented piston rod being secured against rotation about its own longitudinal axis with respect to a housing, the segmented piston rod comprising a last segment which abuts the stopper in the reservoir, a second to last segment, and a first segment which is opposite to the last segment,
   wherein at least the first segment of the segmented piston rod comprises an internal thread extending along the longitudinal axis, the internal thread being coupled with and complementary to an external thread of a threaded rod, and wherein rotation of the threaded rod by a drive mechanism advances the segmented piston rod towards the stopper of the reservoir,
   wherein the last segment comprises a guiding element protruding therefrom towards the second to last segment and shaped as a fin, the guiding element comprising an edge which is oriented parallel to a normal axis of the last segment,
   wherein the guiding element is attached to or attachable to the last segment, wherein the guiding element guides the last segment of the segmented piston rod in the reservoir, whereby the guiding element is configured for abutting a wall of the reservoir and guiding the last segment such that the normal axis of the last segment is parallel to a longitudinal axis of the reservoir, and
   wherein the second to last segment comprises a notch such that the guiding element of the last segment passes through the notch when the segmented piston rod transfers from the curved configuration to the linear configuration.

2. The segmented piston rod for an injection device according to claim 1, wherein the hinge is a strap hinge.

3. The segmented piston rod for an injection device according to claim 1, wherein the guiding element is located opposite to an axis of the hinge and has a plane that is oriented perpendicular to the axis of the hinge.

4. The segmented piston rod for an injection device according to claim 1, wherein the edge of the guiding element abuts the wall of the reservoir as the last segment enters the reservoir.

5. The segmented piston rod for an injection device according to claim 4, wherein the guiding element acts as a lever arm on the last segment and ensures that the normal axis of the last segment is parallel to the longitudinal axis of the reservoir when the last segment abuts the stopper of the reservoir.

6. A segmented piston rod for an injection device for delivering a medication from a reservoir comprising a stopper, the segmented piston rod comprising:
   a plurality of segments joined together via a hinge located on one side of each of the plurality of segments such that the segmented piston rod can be bent in one direction in a curved configuration by articulating subsequent hinges while an axial force can be transmitted by the segmented piston rod to the stopper when the subsequent hinges are closed in a linear configuration and the segments abut each other on an opposite side of the hinge from the one side,
   the segmented piston rod comprising a last segment which abuts the stopper in the reservoir, a second to last segment, and a first segment which is opposite to the last segment,
   wherein at least the first segment of the segmented piston rod comprises an internal thread extending along a longitudinal axis of the segmented piston rod, the internal thread being coupled with and complementary to an external thread of a threaded rod,
   wherein the segmented piston rod is secured against rotation along its own longitudinal axis with respect to the threaded rod,
   wherein rotation of the threaded rod advances the segmented piston rod towards the stopper of the reservoir,
   wherein the last segment comprises a guiding element protruding therefrom towards the second to last segment and shaped as a fin, the guiding element comprising an edge which is oriented parallel to a normal axis of the last segment,
   wherein the guiding element is attached to or attachable to the last segment, wherein the guiding element guides the last segment of the segmented piston rod in the reservoir, whereby the guiding element is configured for abutting a wall of the reservoir and guiding the last segment such that the normal axis of the last segment is parallel to a longitudinal axis of the reservoir, and
   wherein the second to last segment comprises a notch such that the guiding element of the last segment passes through the notch when the segmented piston rod transfers from the curved configuration to the linear configuration.

7. The segmented piston rod for an injection device according to claim 6, wherein the hinge is a strap hinge.

8. The segmented piston rod for an injection device according to claim 6, wherein the guiding element is located opposite to an axis of the hinge and has a plane that is oriented perpendicular to the axis of the hinge.

9. The segmented piston rod for an injection device according to claim 6, wherein the edge of the guiding element abuts the wall of the reservoir as the last segment enters the reservoir.

10. The segmented piston rod for an injection device according to claim 9, wherein the guiding element acts as a lever arm on the last segment and ensures that the normal axis of the last segment is parallel to the longitudinal axis of the reservoir when the last segment abuts the stopper of the reservoir.

11. A segmented piston rod for an injection device for delivering a medication from a reservoir comprising a stopper, the segmented piston rod comprising:

a plurality of segments joined together via a hinge located on one side of each of the plurality of segments such that the segmented piston rod can be bent in one direction in a curved configuration by articulating subsequent hinges while an axial force can be transmitted by the segmented piston rod to the stopper when the subsequent hinges are closed in a linear configuration and the segments abut each other on an opposite side of the hinge from the one side, the segmented piston rod being secured against rotation about its own longitudinal axis with respect to a housing, the segmented piston rod comprising a last segment which abuts the stopper in the reservoir, a second to last segment, and a first segment which is opposite to the last segment, wherein at least the first segment of the segmented piston rod comprises an internal thread extending along the longitudinal axis, the internal thread being coupled with and complementary to an external thread of a threaded rod, and wherein rotation of the threaded rod by a drive mechanism advances the segmented piston rod towards the stopper of the reservoir, wherein the last segment comprises a guiding element protruding therefrom towards the second to last segment and shaped as a fin, the guiding element comprising an edge which is oriented parallel to a normal axis of the last segment, wherein the second to last segment comprises a notch such that the guiding element of the last segment passes through the notch when the segmented piston rod transfers from the curved configuration to the linear configuration, and wherein the edge of the guiding element abuts the wall of the reservoir as the last segment enters the reservoir.

12. The segmented piston rod for an injection device according to claim 11, wherein the hinge is a strap hinge.

13. The segmented piston rod for an injection device according to claim 11, wherein the guiding element is located opposite to an axis of the hinge and has a plane that is oriented perpendicular to the axis of the hinge.

14. The segmented piston rod for an injection device according to claim 11, wherein the guiding element acts as a lever arm on the last segment and ensures that the normal axis of the last segment is parallel to the longitudinal axis of the reservoir when the last segment abuts the stopper of the reservoir.

* * * * *